United States Patent
Lim et al.

(10) Patent No.: US 10,734,131 B2
(45) Date of Patent: Aug. 4, 2020

(54) ORGANIC TRANSISTOR AND GAS SENSOR

(71) Applicant: LG CHEM, LTD., Seoul (KR)

(72) Inventors: Bogyu Lim, Daejeon (KR);
Yong-Young Noh, Seoul (KR); Jaechol Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 29 days.

(21) Appl. No.: 16/077,146

(22) PCT Filed: Jun. 1, 2017

(86) PCT No.: PCT/KR2017/005745
§ 371 (c)(1),
(2) Date: Aug. 10, 2018

(87) PCT Pub. No.: WO2017/213379
PCT Pub. Date: Dec. 14, 2017

(65) Prior Publication Data
US 2019/0027701 A1    Jan. 24, 2019

(30) Foreign Application Priority Data

Jun. 8, 2016  (KR) .................. 10-2016-0071224

(51) Int. Cl.
*H01B 1/12*      (2006.01)
*H01L 51/00*     (2006.01)
(Continued)

(52) U.S. Cl.
CPC ............. *H01B 1/12* (2013.01); *C07D 417/14* (2013.01); *C07D 487/02* (2013.01);
(Continued)

(58) Field of Classification Search
CPC .......... H01B 1/12; H01B 1/124; H01B 1/125; H01B 1/127; H01B 1/128; H01B 1/20; H01L 51/0032; H01L 51/0034; H01L 51/0035; H01L 51/0036; H01L 51/0039; H01L 51/0043; H01L 51/0045; H01L 51/0048; H01L 51/0052; H01L 51/0055; H01L 51/0058; H01L 51/0071;
(Continued)

(56) References Cited

U.S. PATENT DOCUMENTS 6,953,947 B2   10/2005  Son et al.
8,222,633 B2   7/2012   Choi et al.
(Continued)

FOREIGN PATENT DOCUMENTS

GB         2376565       12/2002
KR    1020060042013 A    5/2006
(Continued)

OTHER PUBLICATIONS

Extended European Search Report corresponding to European Patent Application No. 17810502.9 dated Nov. 21, 2018. (7 pages).
(Continued)

*Primary Examiner* — Matthew R Diaz
(74) *Attorney, Agent, or Firm* — Myers Bigel, P.A.

(57) ABSTRACT

The present specification relates to an organic transistor including an organic semiconductor layer including a compound, and a gas sensor to which the organic transistor is applied.

20 Claims, 21 Drawing Sheets

(51) Int. Cl.
| | |
|---|---|
| *H01L 51/05* | (2006.01) |
| *G01N 27/414* | (2006.01) |
| *G01N 33/00* | (2006.01) |
| *C07D 417/14* | (2006.01) |
| *C07D 487/02* | (2006.01) |
| *C07D 495/02* | (2006.01) |
| *C07D 487/04* | (2006.01) |
| *C07F 7/08* | (2006.01) |

(52) U.S. Cl.
CPC ......... *C07D 487/04* (2013.01); *C07D 495/02* (2013.01); *C07F 7/0816* (2013.01); *G01N 27/4141* (2013.01); *G01N 33/0042* (2013.01); *H01L 51/0036* (2013.01); *H01L 51/0072* (2013.01); *H01L 51/0094* (2013.01); *H01L 51/05* (2013.01)

(58) Field of Classification Search
CPC ............ H01L 51/0072; H01L 51/0073; H01L 51/0074; H01L 51/0094; G01N 27/4141; G01N 27/4143; G01N 33/0036; G01N 33/0042; G01N 33/0047; G01N 33/0052; G01N 33/0054; C07D 417/14; C07D 487/02; C07D 487/04; C07D 495/02; C07D 495/04; C07D 497/22; C07F 7/08; C07F 7/0812; C07F 7/0816
See application file for complete search history.

(56) References Cited

U.S. PATENT DOCUMENTS

| | | | |
|---|---|---|---|
| 8,946,376 B2 * | 2/2015 | Wurthner | C07D 487/04 257/40 |
| 9,293,718 B2 * | 3/2016 | Hayoz | C09K 11/06 |
| 2016/0293342 A1 * | 10/2016 | Yumoto | H01G 9/2031 |
| 2016/0372680 A1 * | 12/2016 | Lim | C07D 417/14 |
| 2017/0025613 A1 * | 1/2017 | Kanesaka | C08G 61/126 |
| 2018/0057515 A1 | 3/2018 | Lim et al. | |

FOREIGN PATENT DOCUMENTS

| | | | | |
|---|---|---|---|---|
| KR | 1020080075663 A | | 8/2008 | |
| KR | 1020140136892 A | | 12/2014 | |
| KR | 1020150001792 A | | 1/2015 | |
| KR | 1020150105247 A | | 9/2015 | |
| KR | 20150121661 A | * | 10/2015 | |
| KR | 1020150121661 A | | 10/2015 | |
| KR | 20160048137 A | * | 5/2016 | ........... H01G 9/2031 |
| KR | 1020160048137 A | | 5/2016 | |
| KR | 1020160048173 | | 5/2016 | |
| WO | WO-2015163206 A1 | * | 10/2015 | |
| WO | 2016171465 A1 | | 10/2016 | |

OTHER PUBLICATIONS

International Search Report of the International Searching Authority with English translation corresponding to International Patent Application No. PCT/KR2017/005745, dated Sep. 11, 2017. (5 pages).

* cited by examiner

[Figure 1]
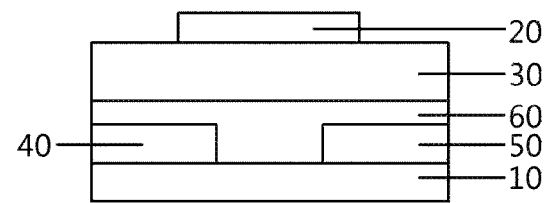
[Figure 2]
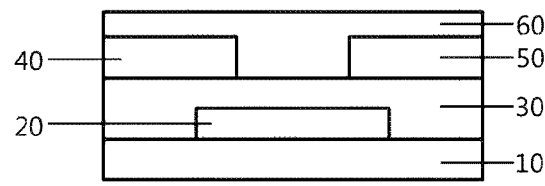
[Figure 3]
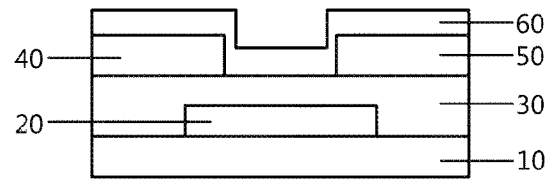
[Figure 4]
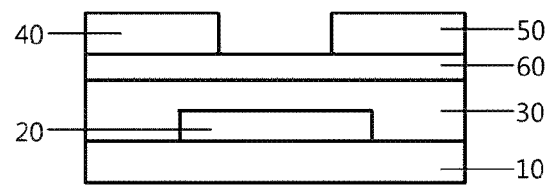

[Figure 5]
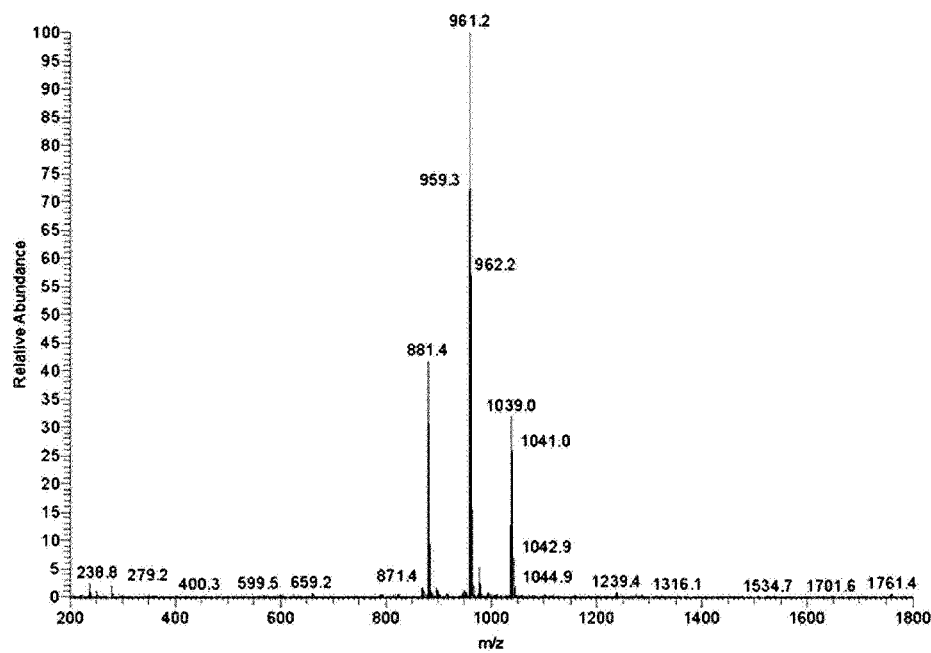
[Figure 6]
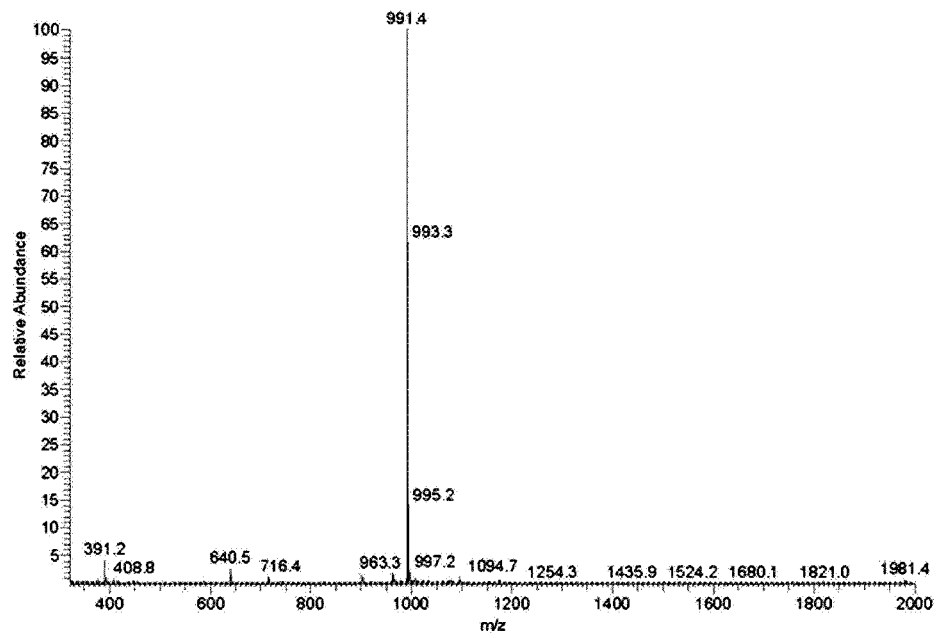

[Figure 7]
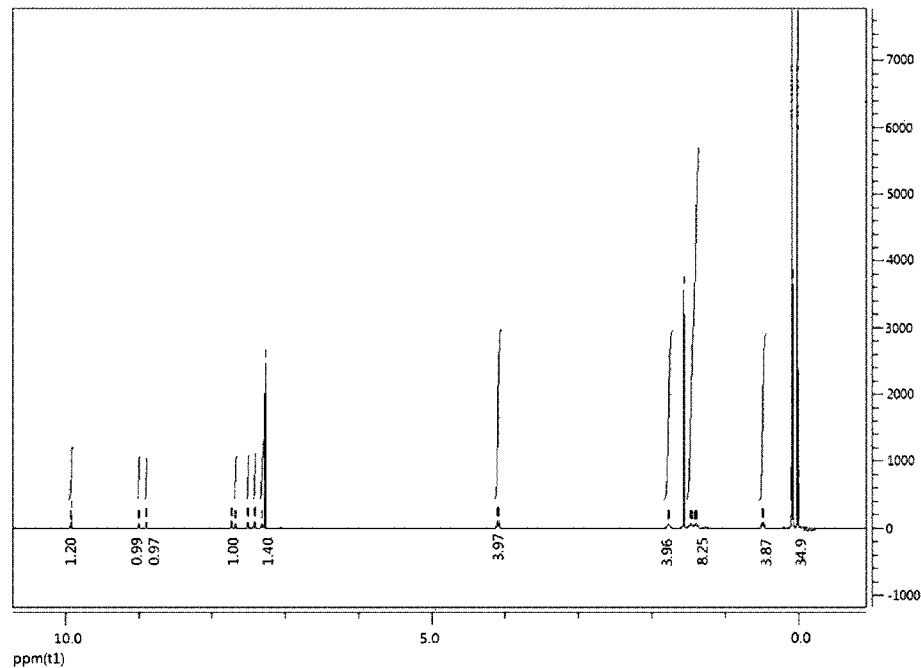
[Figure 8]
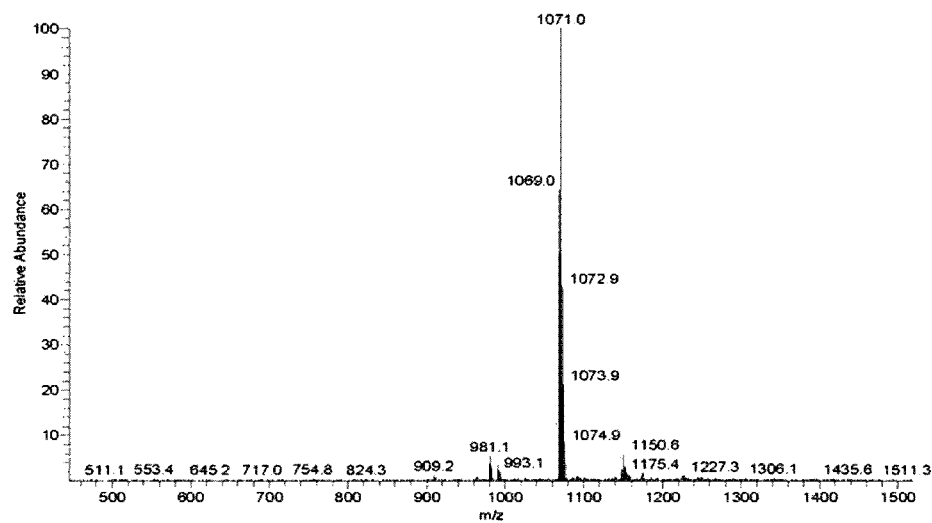

[Figure 9]
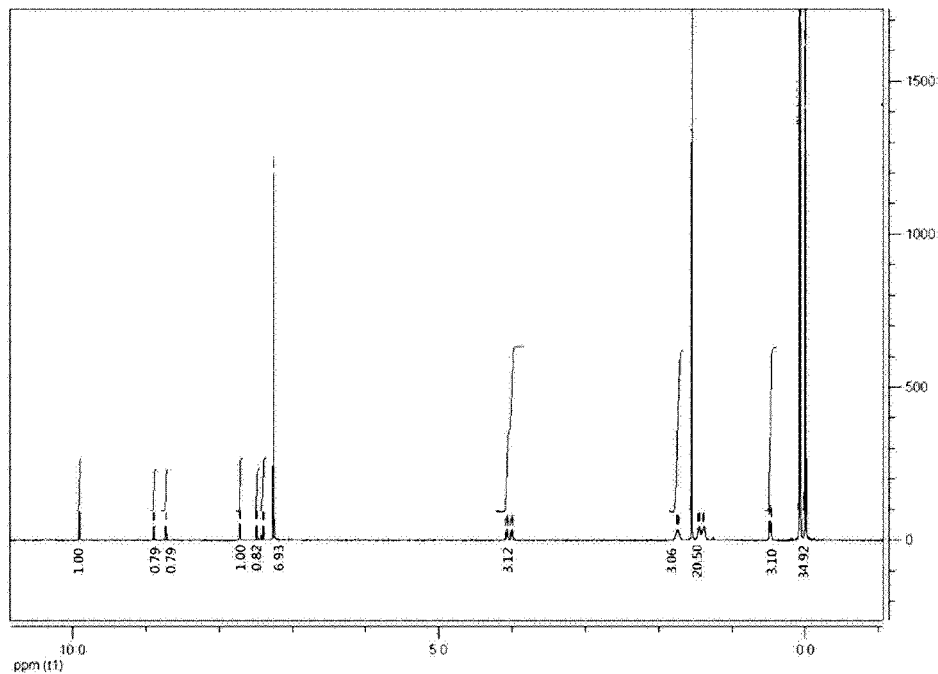
[Figure 10]
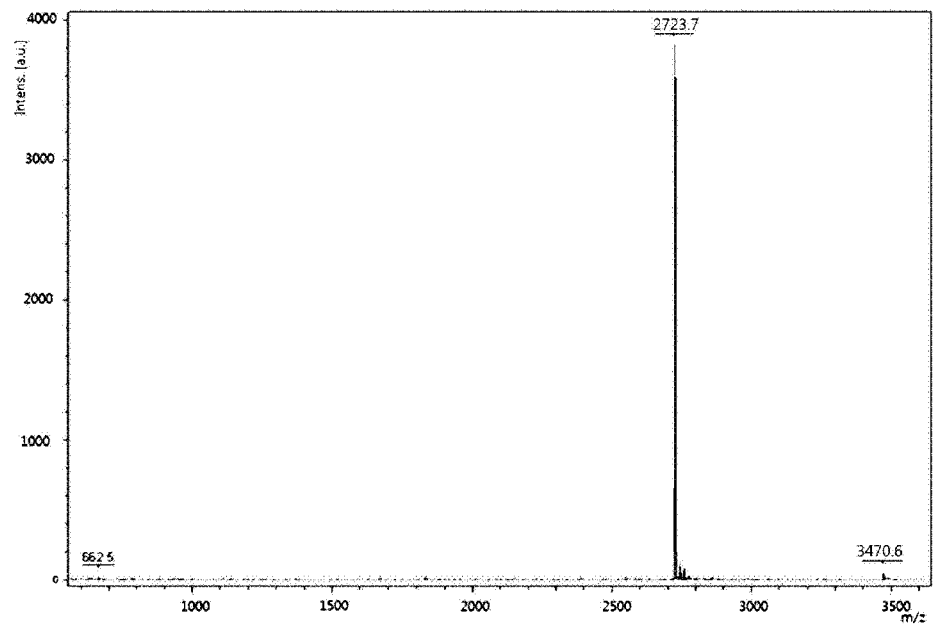

[Figure 11]
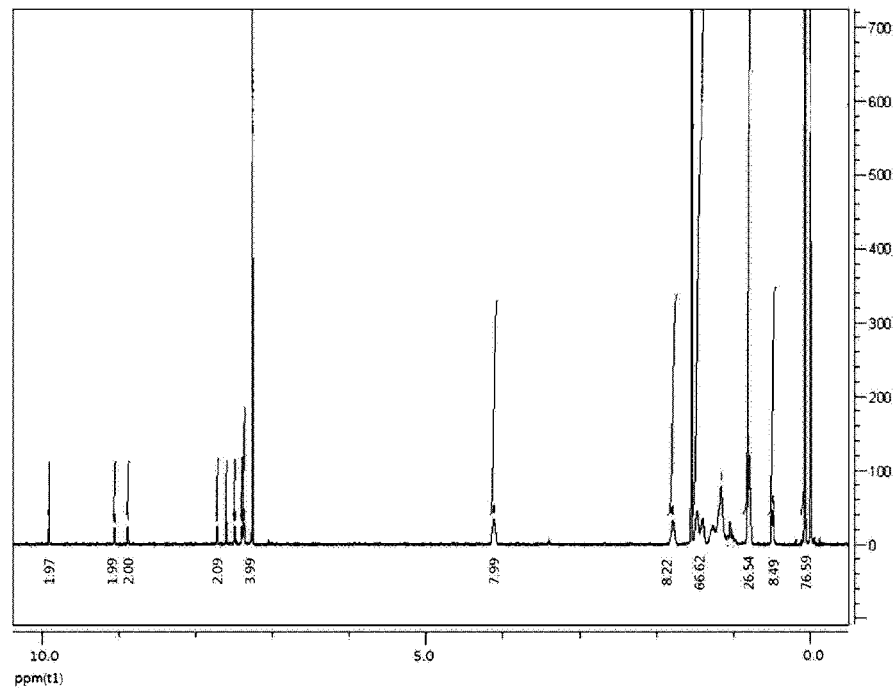
[Figure 12]
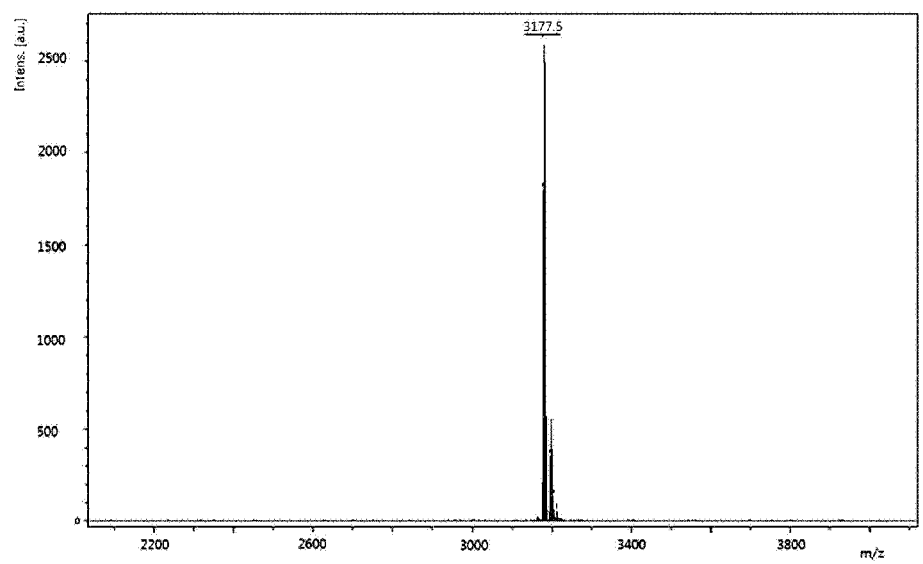

[Figure 13]
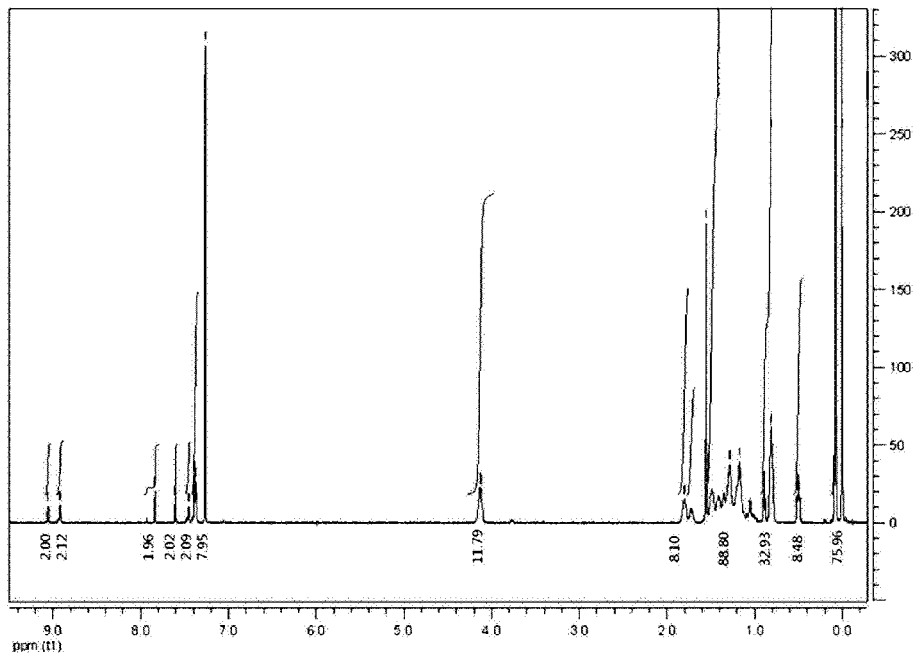
[Figure 14]
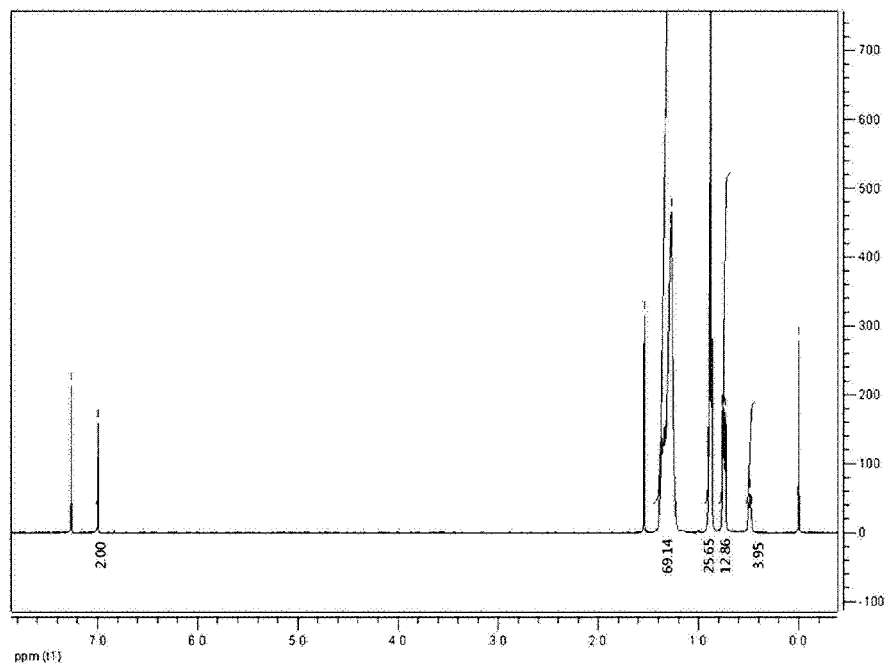

[Figure 15]
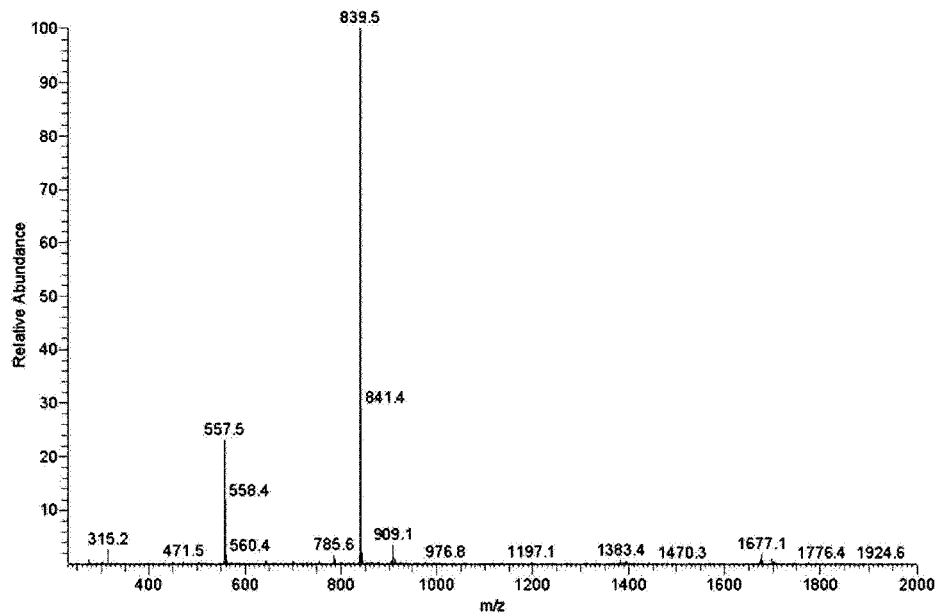
[Figure 16]
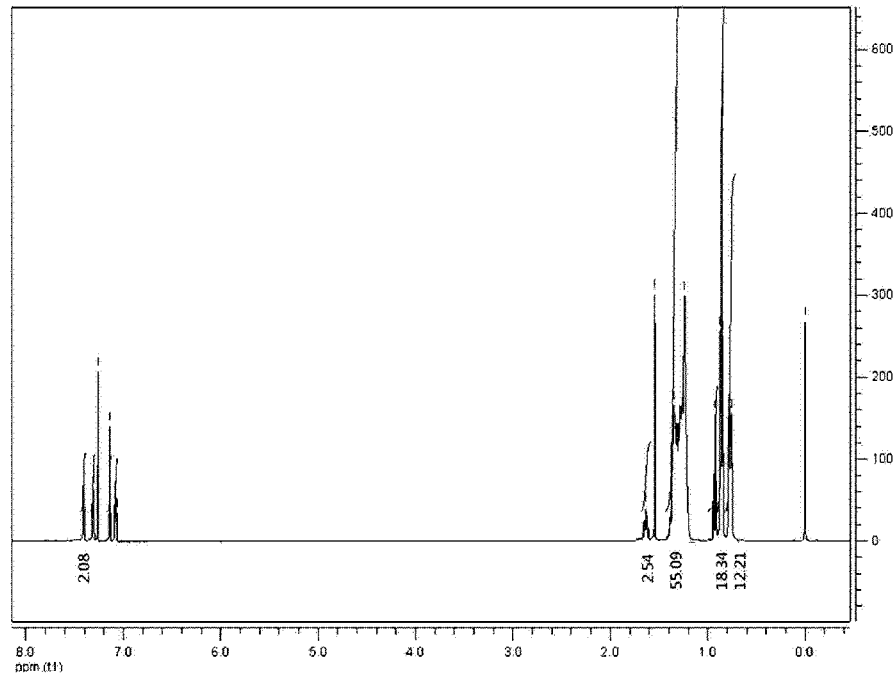

[Figure 17]
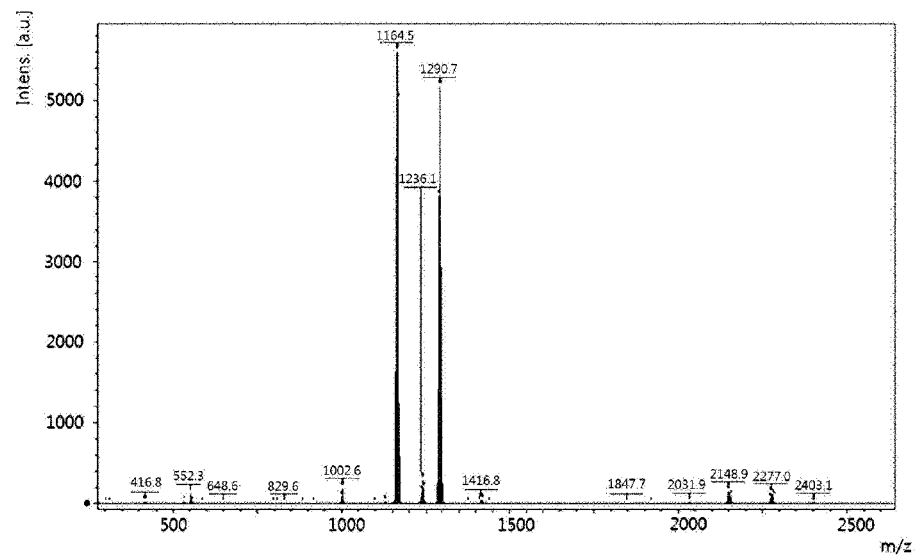
[Figure 18]
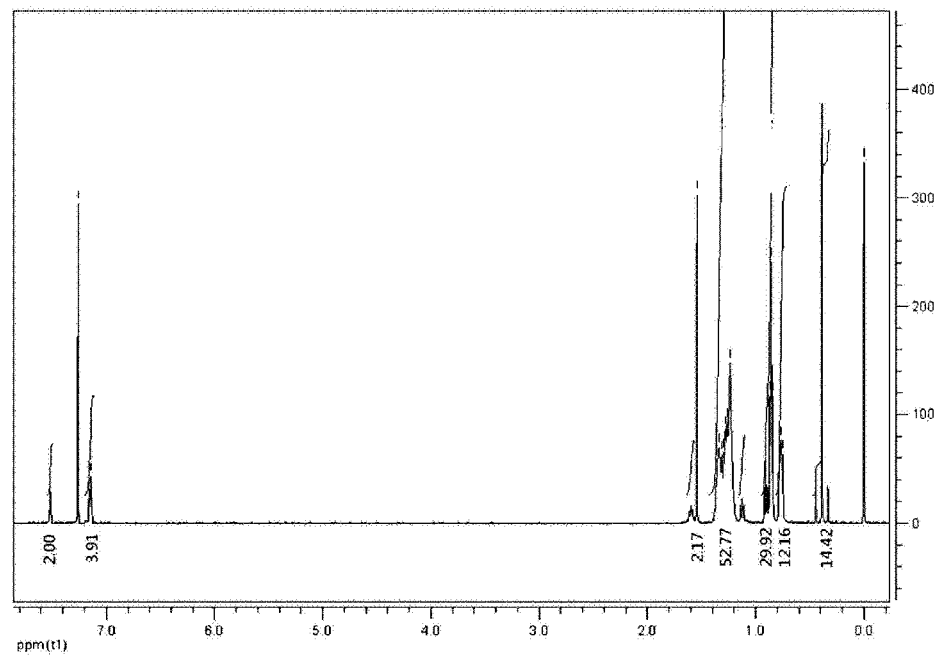

[Figure 19]
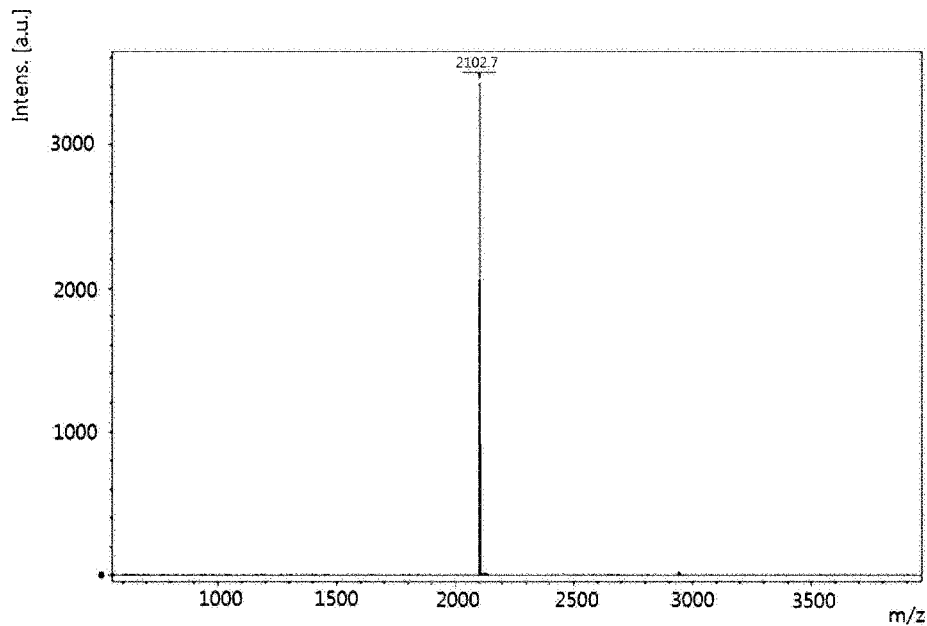
[Figure 20]
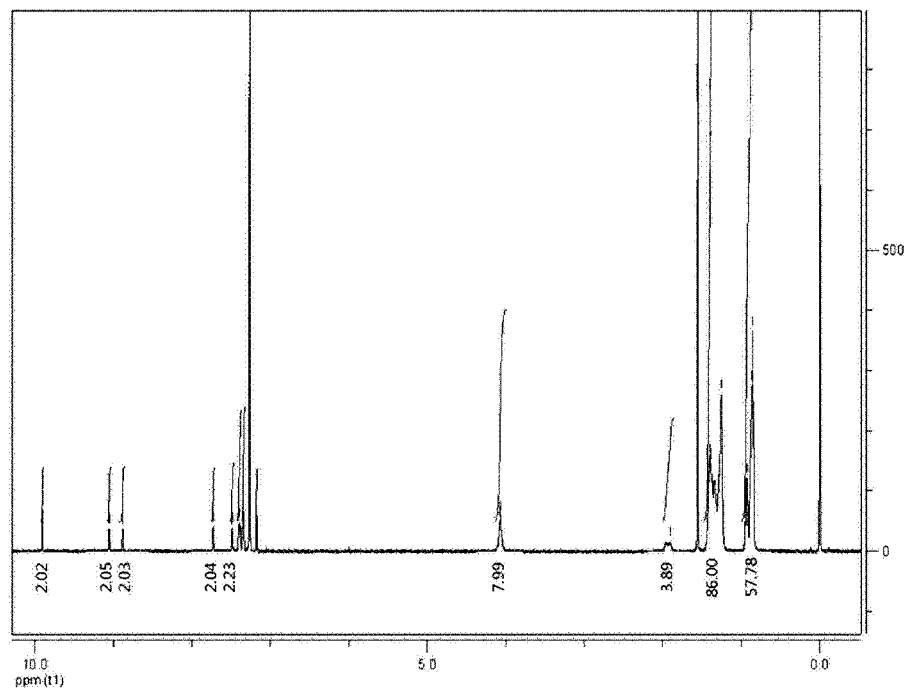

[Figure 21]
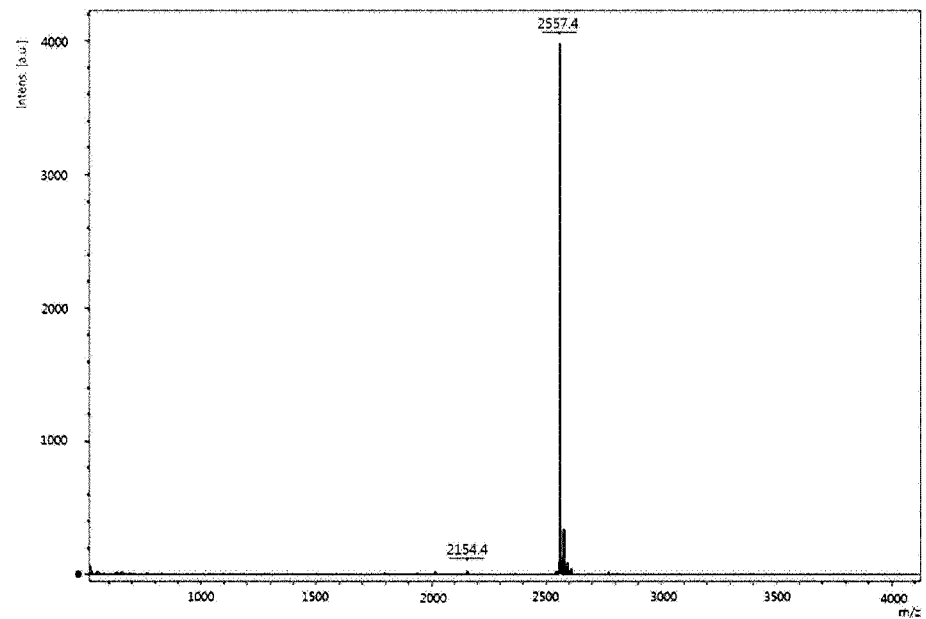
[Figure 22]
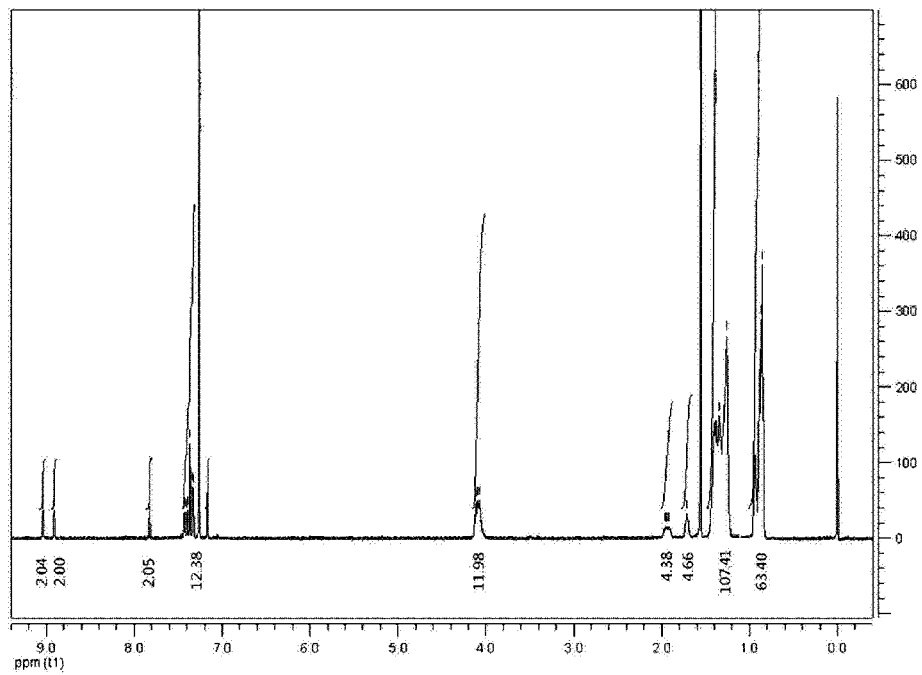

[Figure 23]
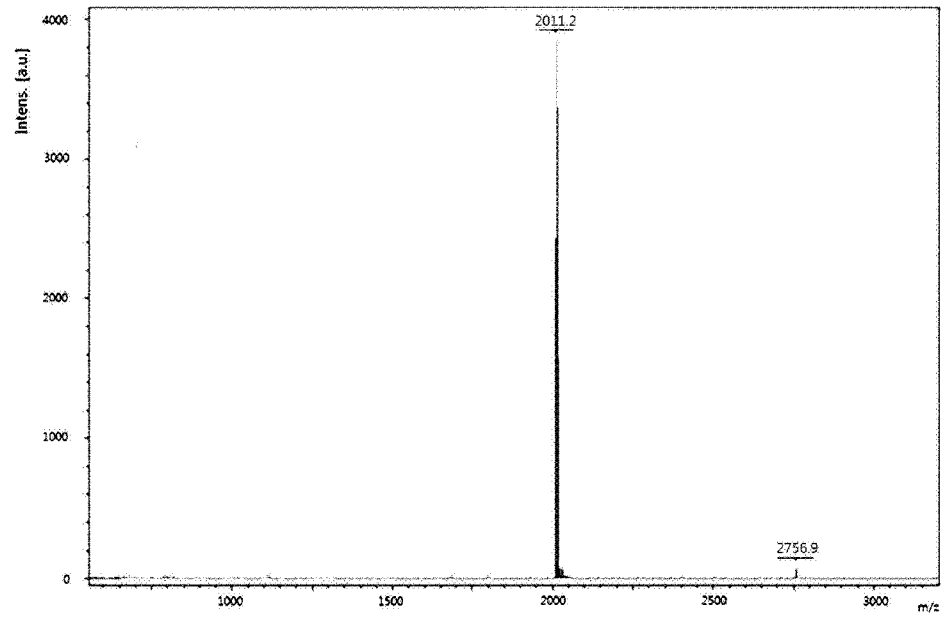
[Figure 24]
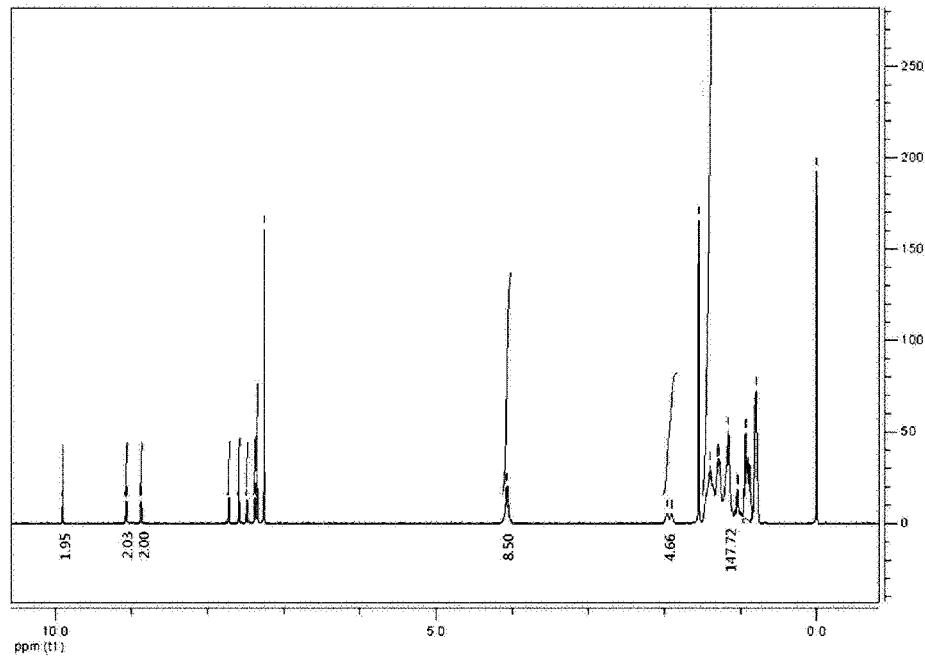

[Figure 25]
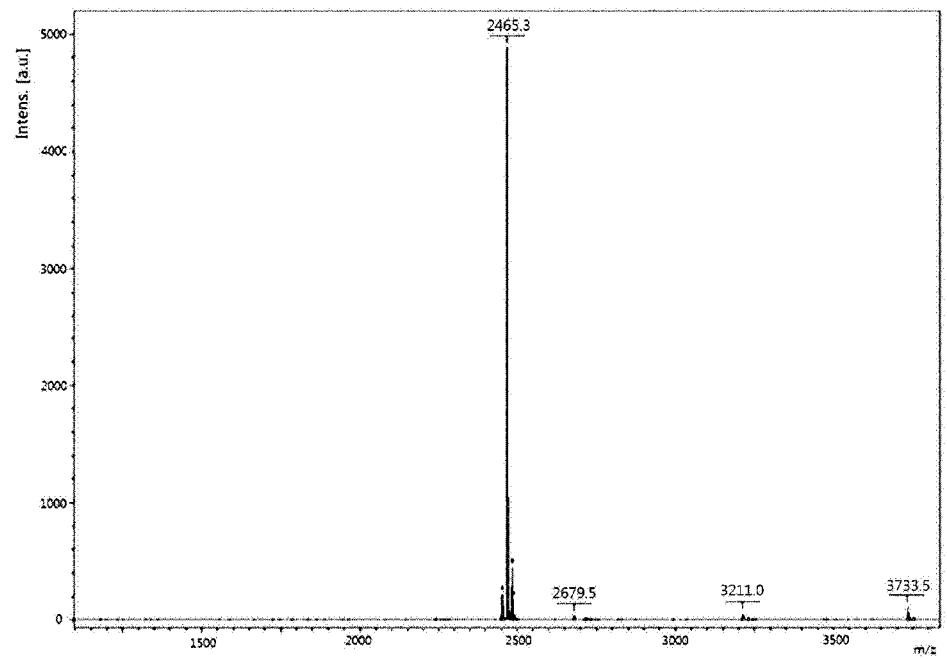
[Figure 26]
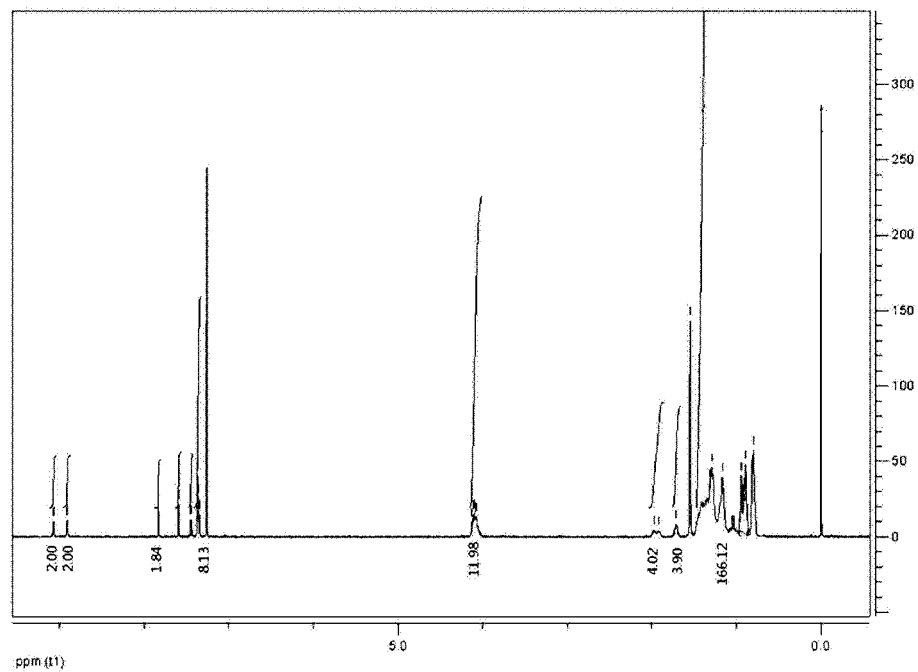

[Figure 27]
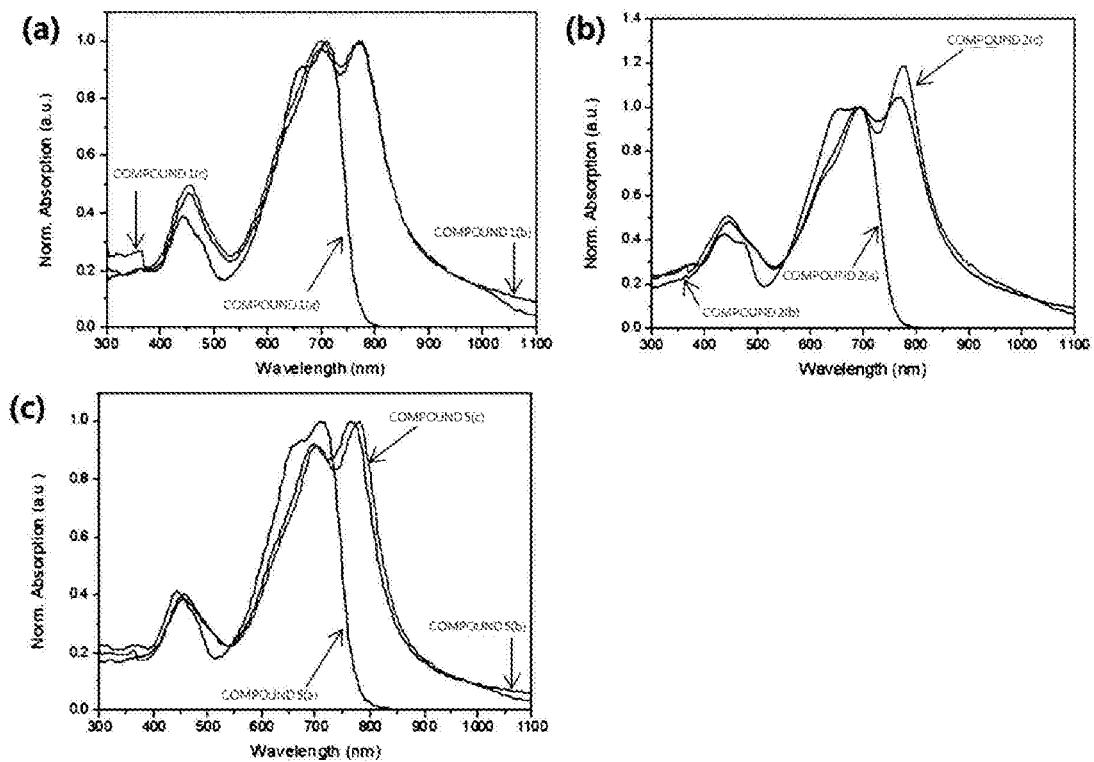
[Figure 28]
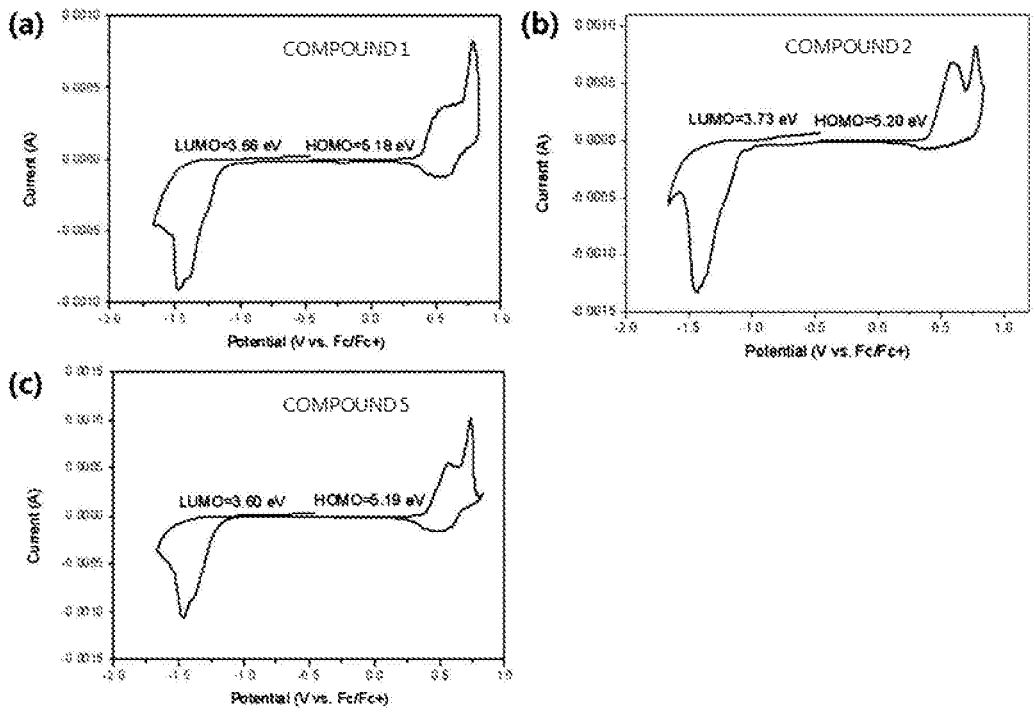

[Figure 29]
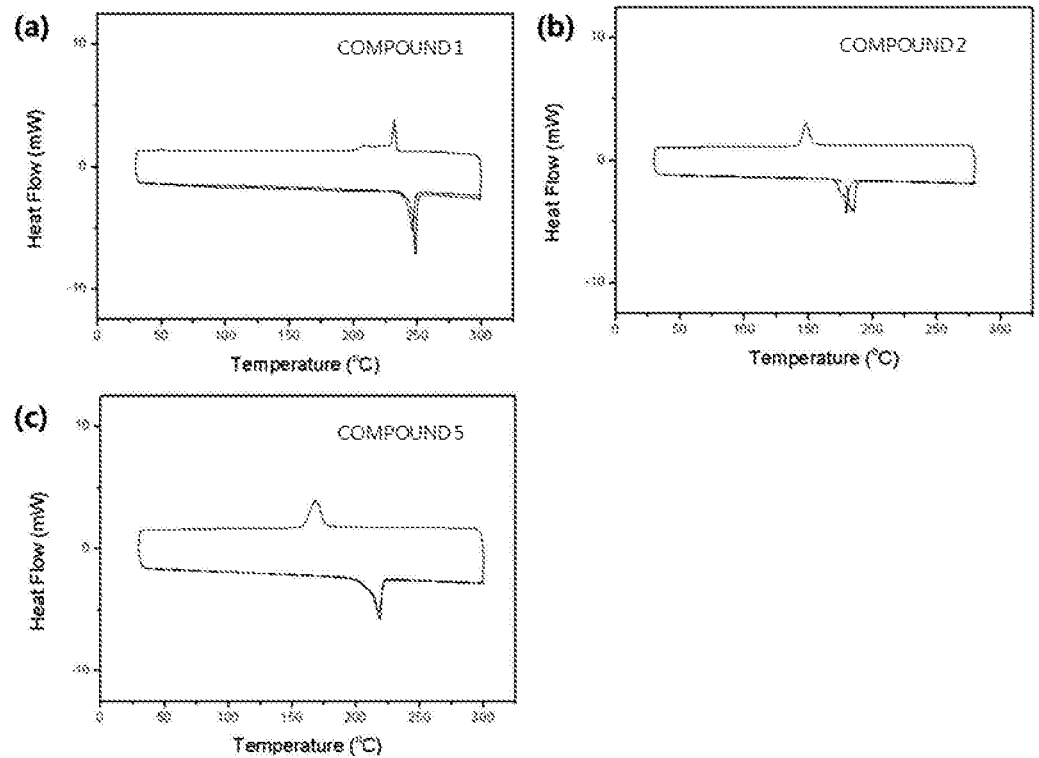
[Figure 30]
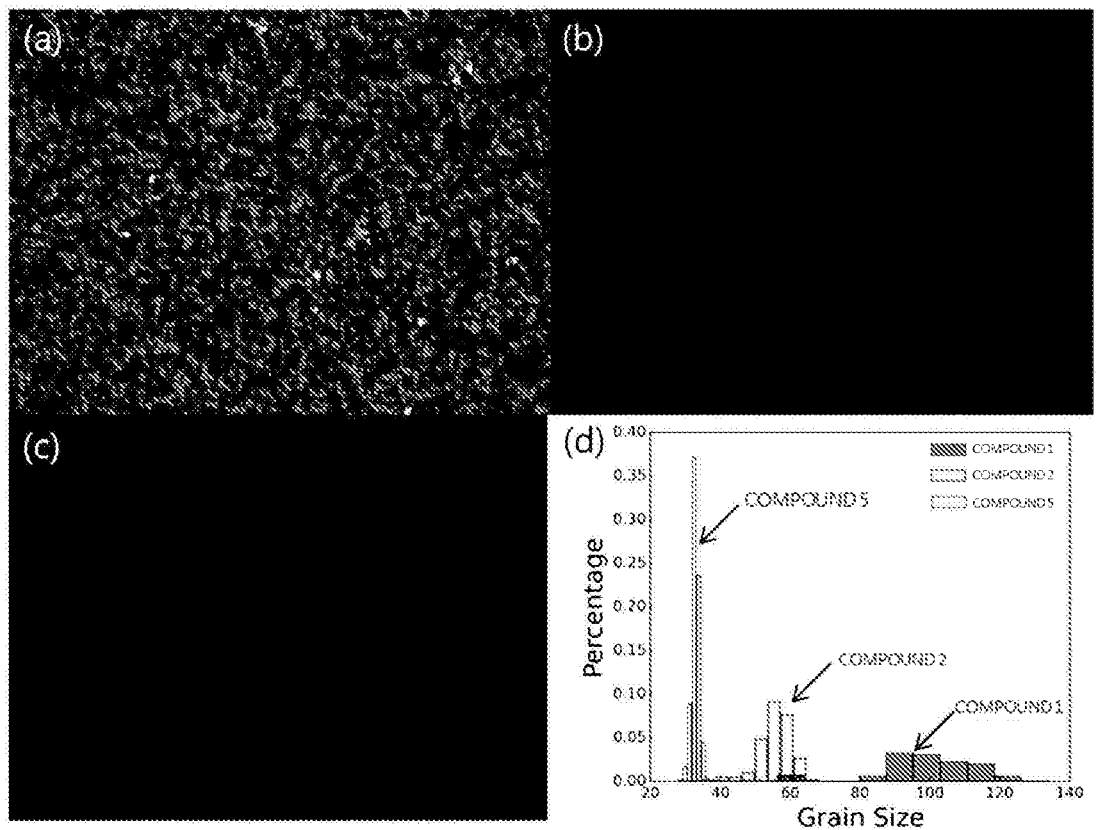

[Figure 31]
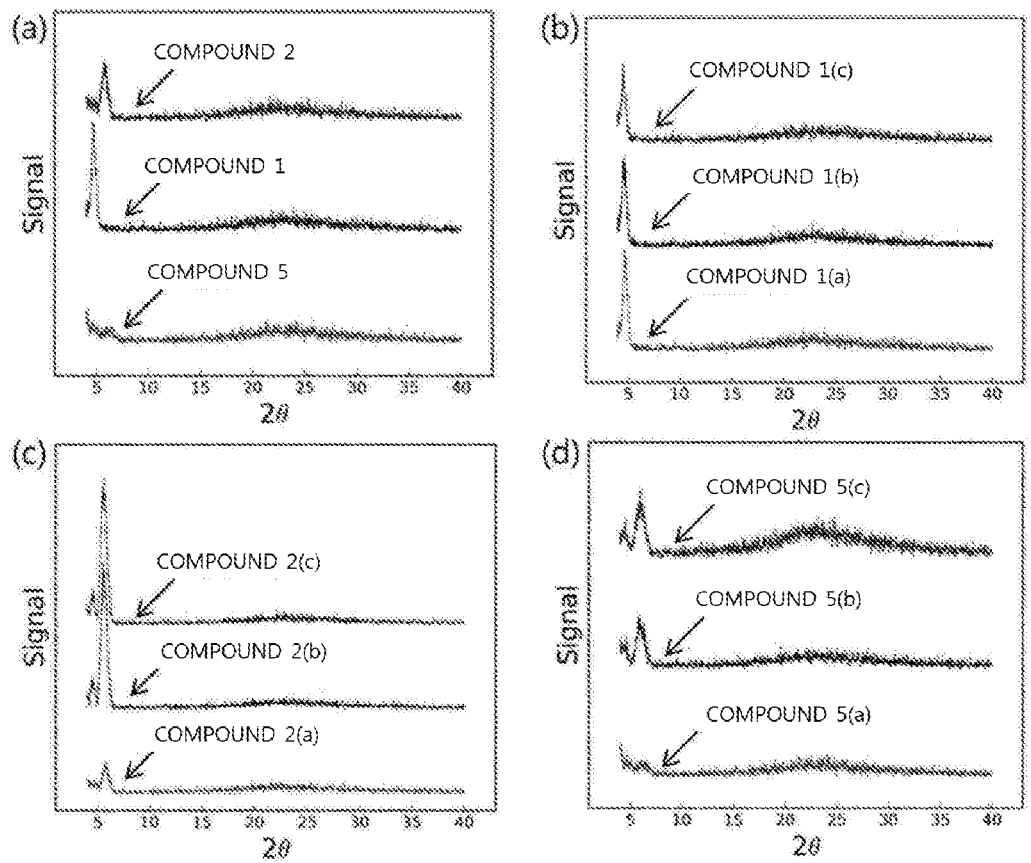
[Figure 32]
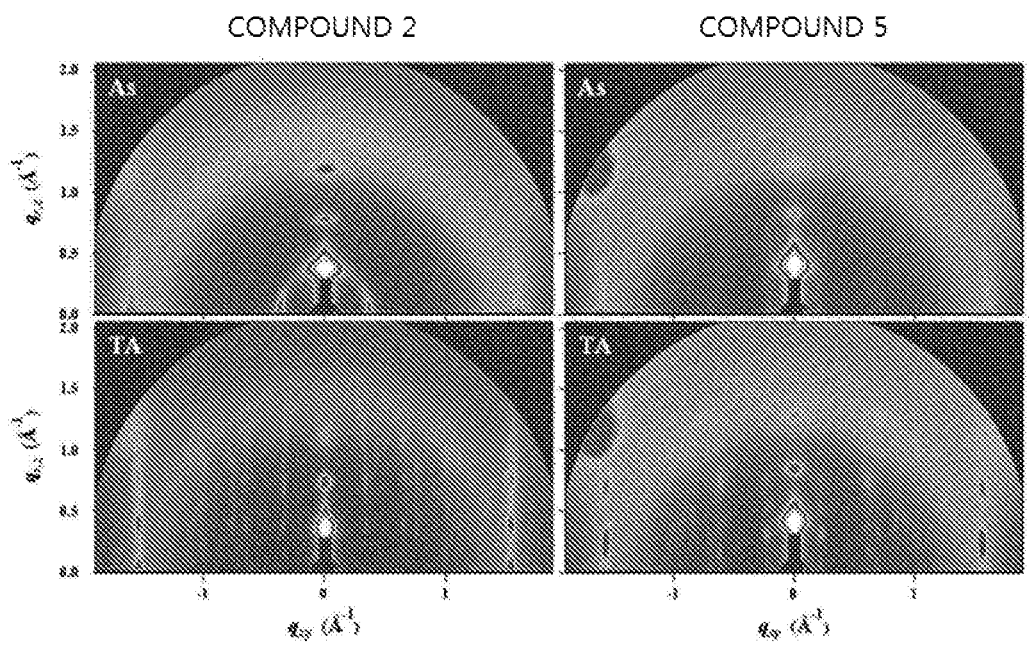

[Figure 33]
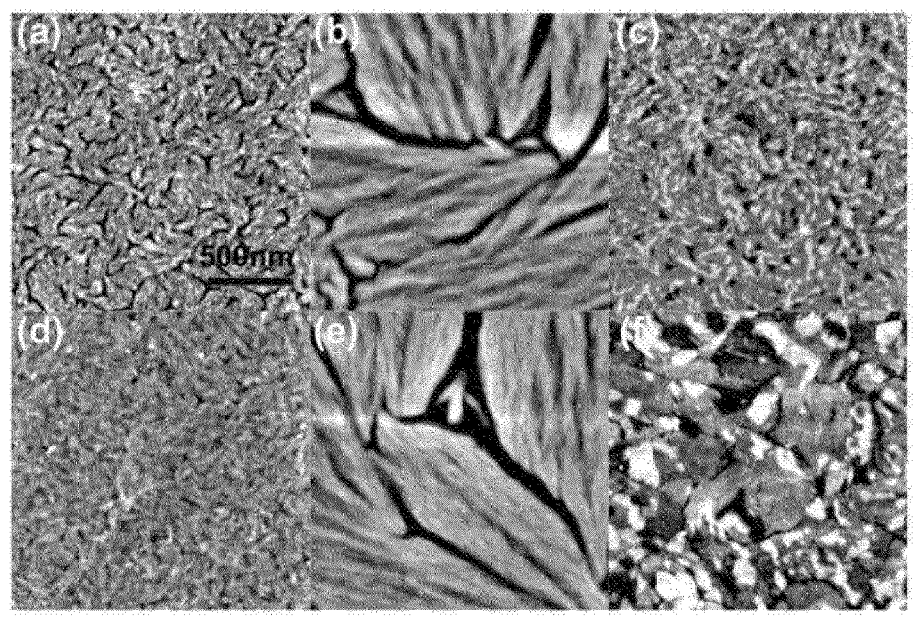
[Figure 34]
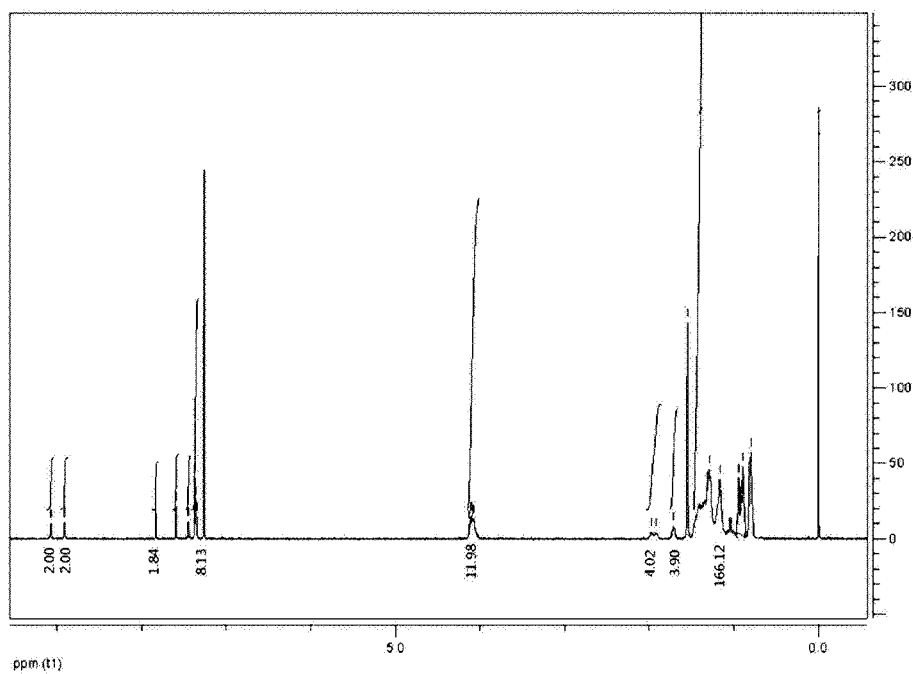

[Figure 35]
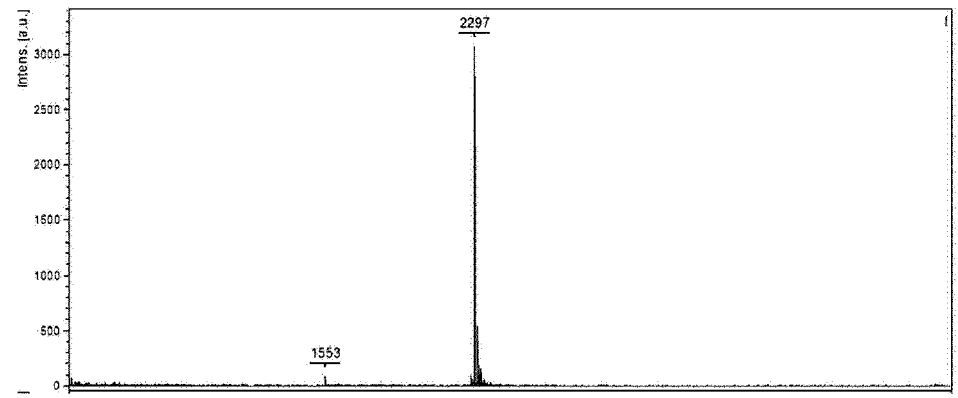
[Figure 36]
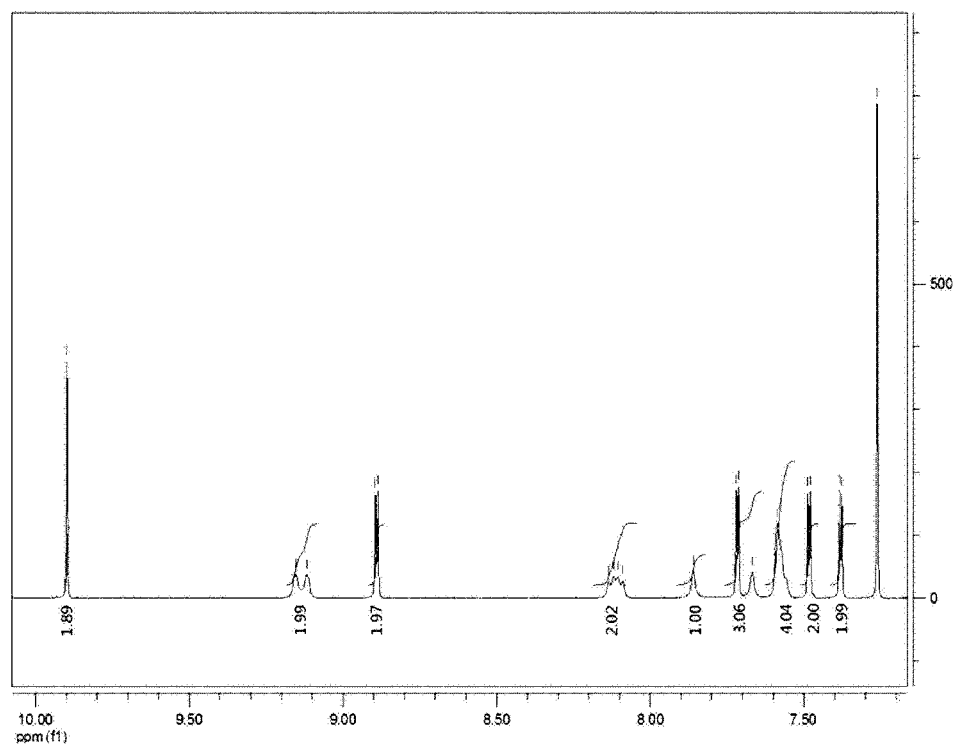

[Figure 37]
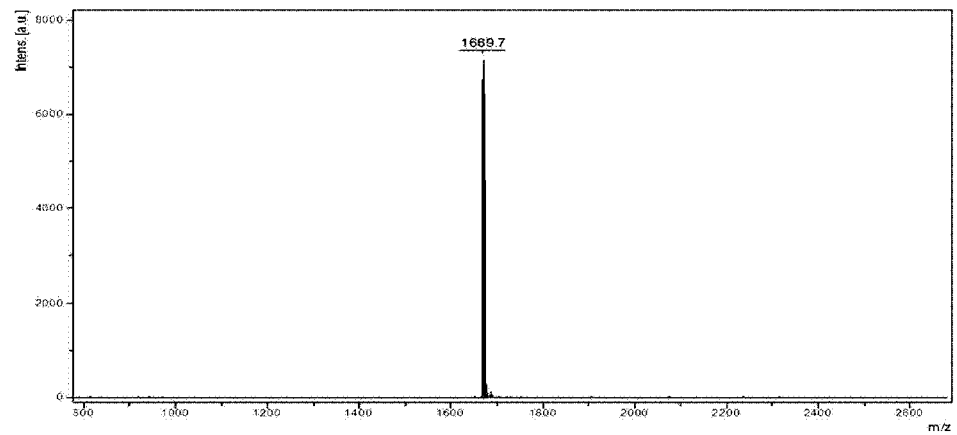
[Figure 38]
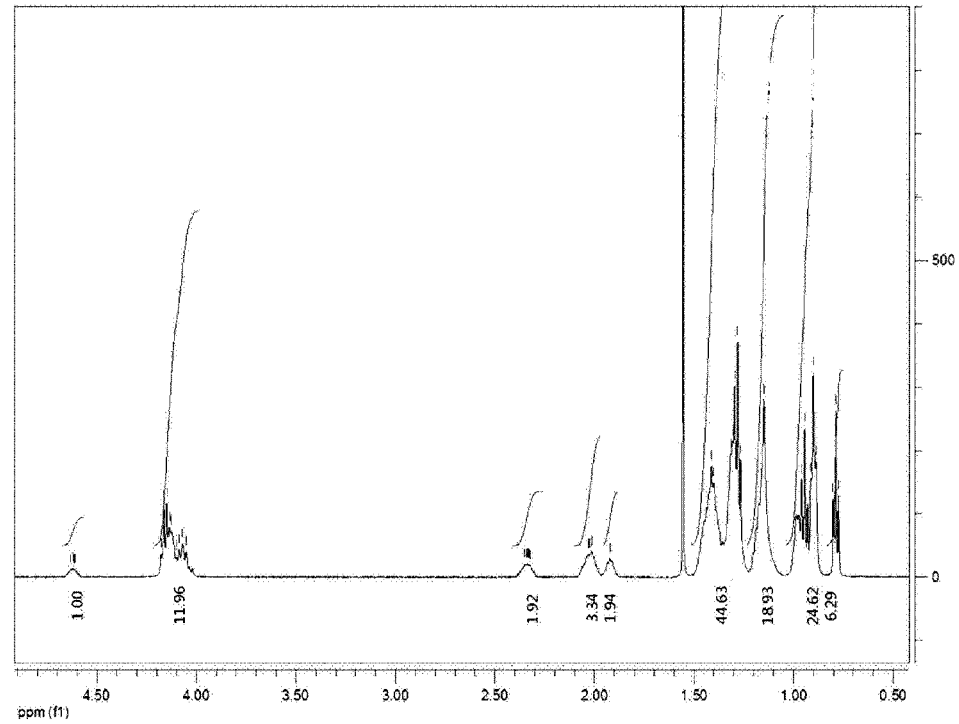

[Figure 39]
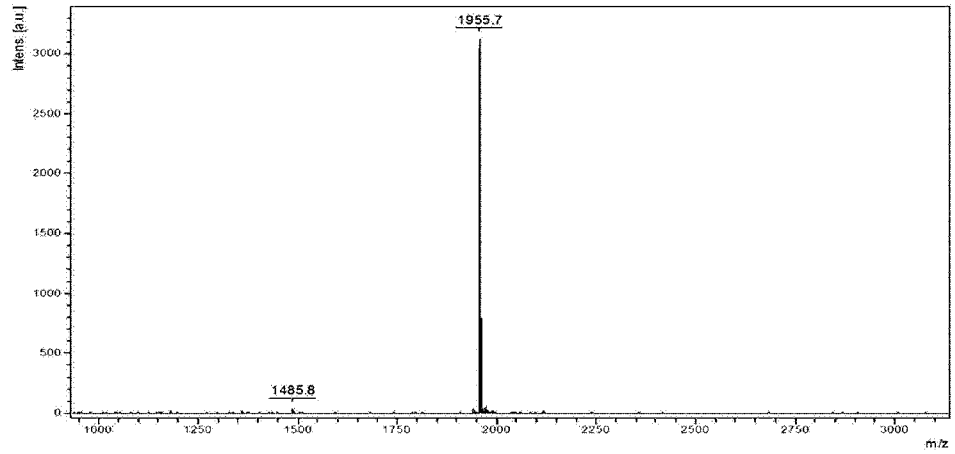
[Figure 40]
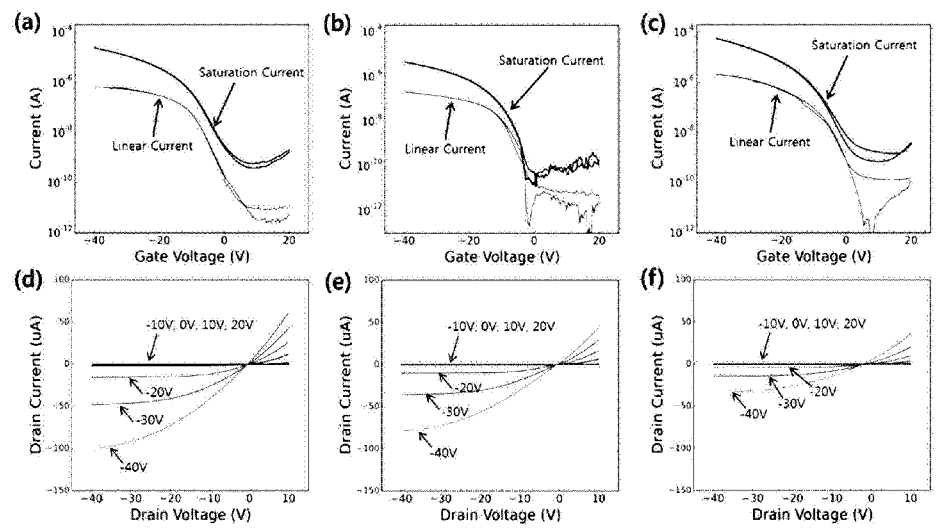
[Figure 41]
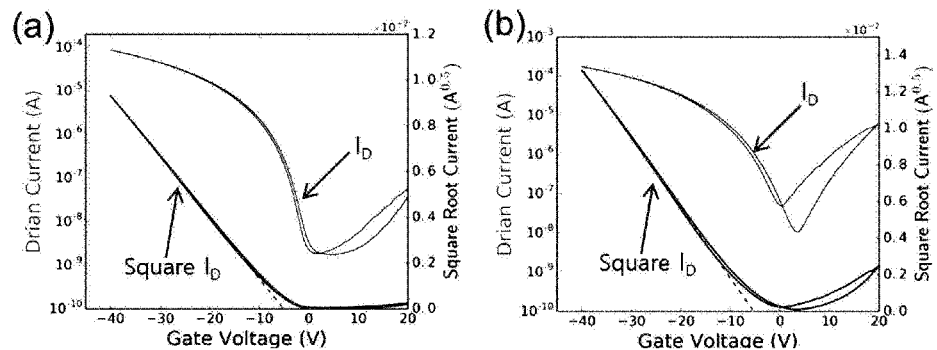

[Figure 42]
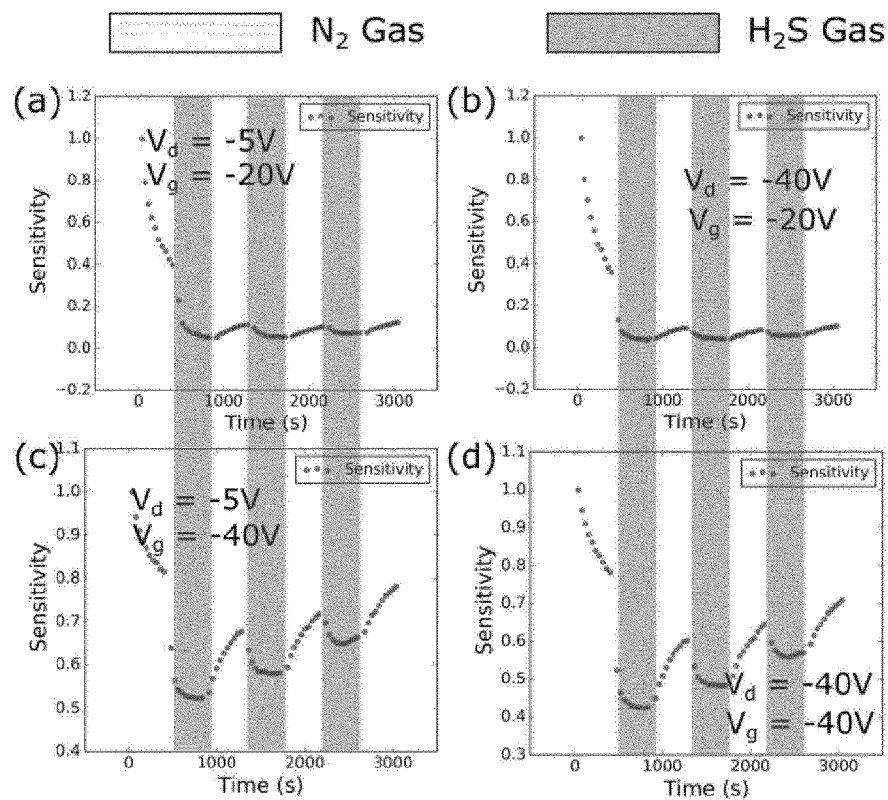

[Figure 43]
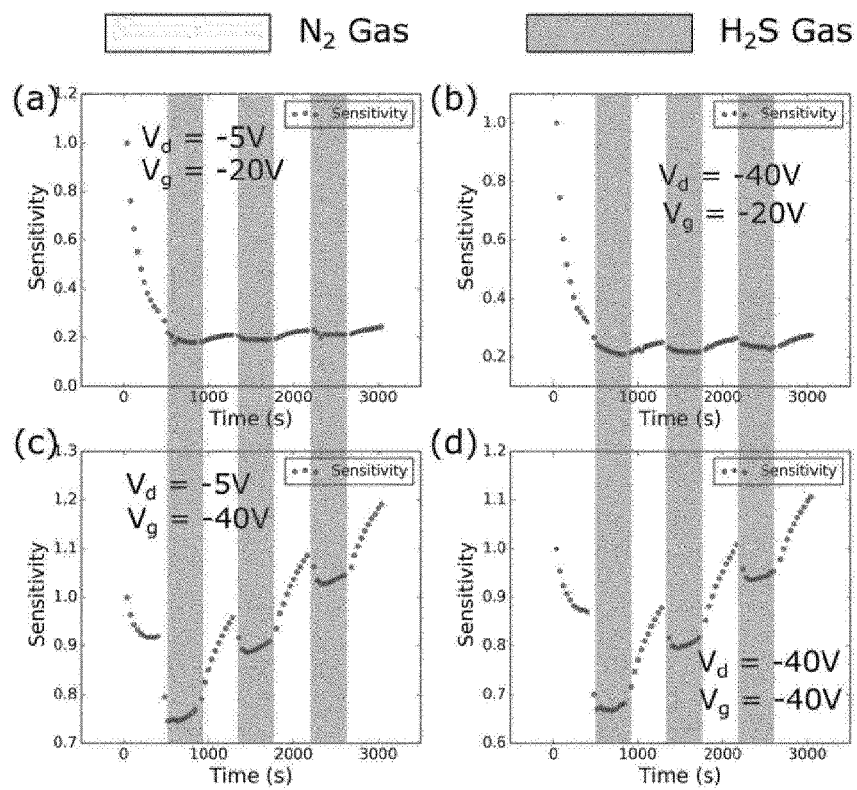

ORGANIC TRANSISTOR AND GAS SENSOR

CROSS REFERENCE TO RELATED APPLICATIONS

This application is a 35 U.S.C. § 371 national stage application of PCT International Application No. PCT/KR2017/005745, filed on Jun. 1, 2017, which claims priority from Korean Patent Application No. 10-2016-0071224, filed on Jun. 8, 2016, the contents of which are incorporated herein by reference in their entireties. The above-referenced PCT International Application was published in the Korean language as International Publication No. WO 2017/213379 A1 on Dec. 14, 2017.

TECHNICAL FIELD

This application claims priority to and the benefit of Korean Patent Application No. 10-2016-0071224 filed in the Korean Intellectual Property Office on Jun. 8, 2016, the entire contents of which are incorporated herein by reference.

The present specification relates to an organic transistor and a gas sensor.

BACKGROUND ART

A field-effect transistor (FET) in the form of a thin film is composed of a source electrode, a drain electrode, a gate electrode, an insulating layer, and a semiconductor layer, and recently, interests in an organic transistor in which an organic material such as a single molecule, a polymer, and an oligomer is applied to a semiconductor layer have been increased.

Among the organic materials, a single molecule for a solution process can be applied to a flexible substrate, can be subjected to a low temperature process, and can be applied to a large area, thereby improving processability and economic feasibility. Further, the single molecule for a solution process has no batch-to-batch difference as compared to a polymer and thus is advantageous in commercialization when applied to a semiconductor layer.

Meanwhile, the structure of the organic transistor may have a top gate or bottom gate structure depending on the position of a gate electrode, and the bottom gate structure may be divided into a top contact or bottom contact structure depending on whether the source/drain electrode is disposed on or below the semiconductor layer.

The top gate structure may be advantageous in performance because the semiconductor layer has a relatively large area in which the semiconductor layer is brought into contact with the source electrode and the drain electrode, and the top gate structure may be advantageous in air stability because a top electrode is applied onto the semiconductor layer. In contrast, the bottom gate structure may be disadvantageous in stability as compared to the top gate structure.

The performance of an organic transistor may be evaluated in terms of charge mobility, on/off ratio, and the like, and a high performance organic semiconductor needs to be developed in order to improve the performance of the organic transistor.

Meanwhile, a gas sensor is installed in various places and thus serves an important role to monitor hazardous materials and contaminants in the atmosphere and environment where we live, and requires characteristics such as a quick response showing how fast the gas sensor can respond to a situation, sensibility showing that the gas sensor can respond to the detection of gas even when detecting a small amount of the gas, durability showing how long the gas sensor can operate, and economic feasibility showing that the gas sensor can be used by consumers without burdens. Further, the gas sensor needs to have characteristics of the easy integration and enumeration in order to be combined with an existing semiconductor process technology.

Examples of the operation principle of the gas sensor include a semiconductor type which uses a change of resistance values according to a change in amount of gas and an oscillator type which uses a change in frequency when gas is adsorbed onto an oscillator, which oscillates with a predetermined frequency. Most of the gas sensors have been used as the semiconductor type gas sensors having simple circuits and showing stable thermal characteristics at room temperature.

The semiconductor-type gas sensor is divided to an inorganic semiconductor-type gas sensor in which a silicon semiconductor being an inorganic material forms semiconductor crystals through interatomic covalent bonds and an organic semiconductor-type gas sensor in which the semiconductor crystals are bonded to each other by molecular bonds of a conductive polymer, that is, van der Waals interaction. Among them, a gas sensor based on tin oxide requires a high temperature to operate the sensor, so that products having a micro heater therein are commercially available, and it is difficult to manufacture the gas sensor into a thin film due to the problem. Further, the gas sensor has a limitation for being utilized over a wide application because it is impossible to measure a gas concentration with sensitivity of 50 ppm or less.

A gas sensor based on an organic semiconductor may significantly lower costs for manufacturing an existing gas sensor because the gas sensor can be manufactured in a solution phase through various printing processes by dissolving a semiconductor material in an organic solvent. Therefore, recently, studies have been actively conducted on a printing-type gas sensor which reports an organic semiconductor as a sensing material through a printing process such as inkjet printing, but there have been relatively few research studies conducted on various organic semiconductor materials for sensing.

DETAILED DESCRIPTION OF THE INVENTION

Technical Problem

The present specification provides an organic transistor and a gas sensor.

Technical Solution

An exemplary embodiment of the present specification provides an organic transistor including an organic semiconductor layer including a compound represented by the following Chemical Formula 1.

[Chemical Formula 1]

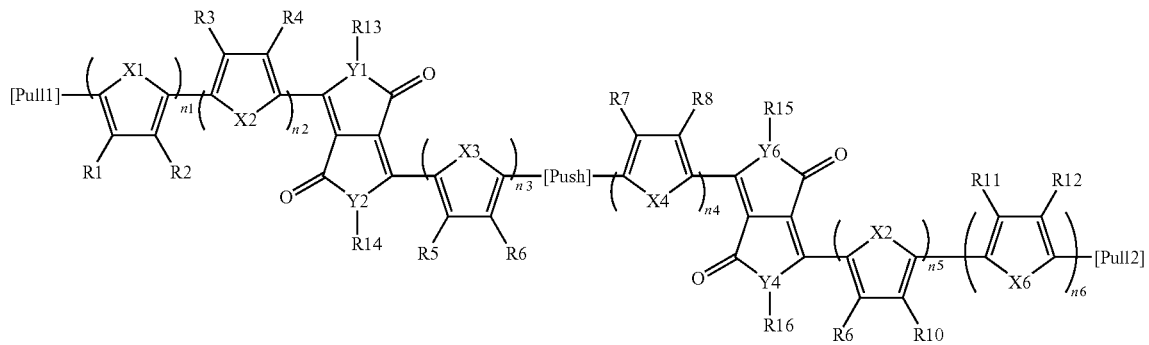

In Chemical Formula 1, n1 to n6 are each an integer from 1 to 3, when n1 to n6 are each 2 or more, two or more structures in the parenthesis are the same as or different from each other, X1 to X6 are the same as or different from each other, and are each independently CRR', NR, O, SiRR', PR, S, GeRR', Se, or Te, Y1 to Y4 are the same as or different from each other, and are each independently CR", N, SiR", P, or GeR",

[Push] is any one of the following structures,

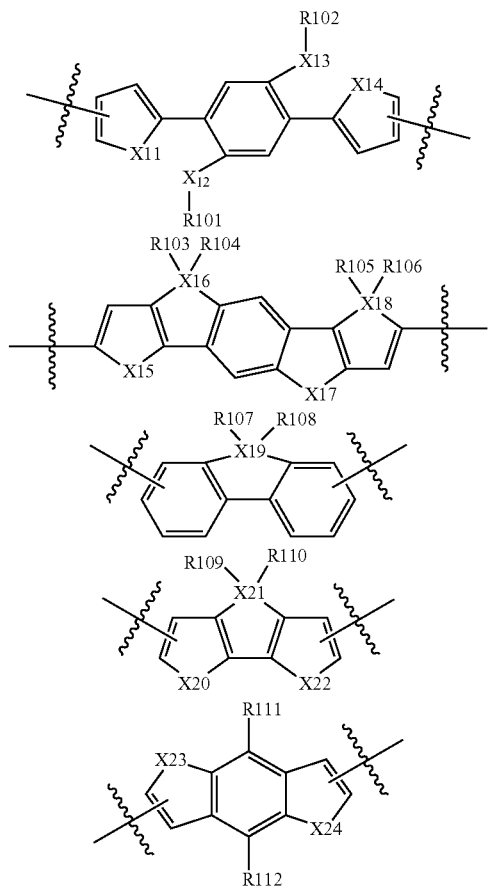

-continued

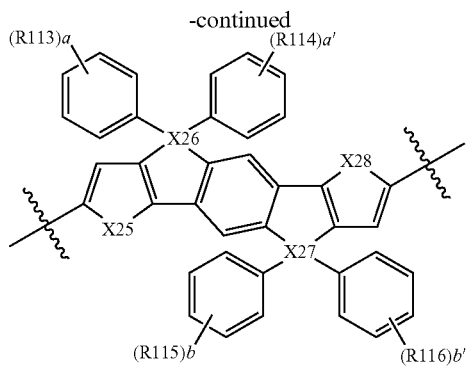

in the structures, a, a', b, and b' are each an integer from 1 to 5, when a is 2 or more, two or more R113's are the same as or different from each other, when a' is 2 or more, two or more R114's are the same as or different from each other, when b is 2 or more, two or more R115's are the same as or different from each other, when b' is 2 or more, two or more R116's are the same as or different from each other, X11, X14, X15, X17, X20, X22, X23, X24, X25, and X28 are the same as or different from each other, and are each independently CRR', NR, O, SiRR', PR, S, GeRR', Se, or Te, X12, X13, X16, X18, X19, X21, X26, and X27 are the same as or different from each other, and are each independently C, Si, or Ge,

[Pull1] and [Pull2] are the same as or different from each other, and are each any one of the following structures,

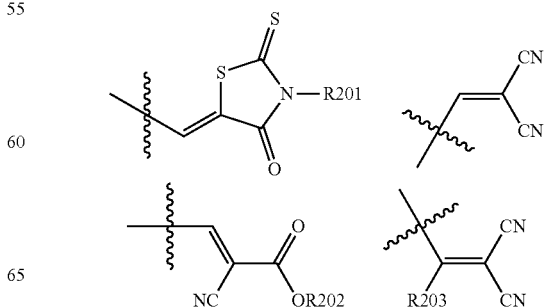

-continued

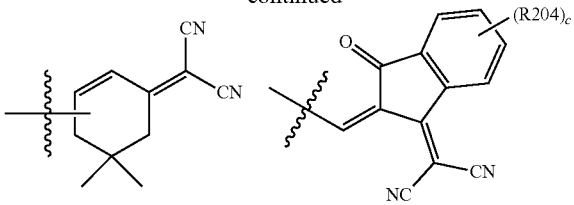

in the structures, c is an integer from 1 to 4, when c is 2 or more, two or more structures in the parenthesis are the same as or different from each other, R, R', R", R1 to R16, R101 to R116, and R201 to R204 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted siloxane group; a substituted or unsubstituted boron group; a substituted or unsubstituted amine group; a substituted or unsubstituted aryl group; or a substituted or unsubstituted heterocyclic group, at least one of R1 to R16 and R101 to R116 includes a substituted or unsubstituted silyl group or a substituted or unsubstituted siloxane group, and

is a moiety bonded to Chemical Formula 1.

Further, an exemplary embodiment of the present specification provides a gas sensor to which the organic transistor is applied.

Advantageous Effects

An organic transistor according to an exemplary embodiment of the present specification has excellent performance by applying a compound, which includes a substituted or unsubstituted silyl group or a substituted or unsubstituted siloxane group in the side-chain thereof, to an organic semiconductor layer.

The organic transistor according to an exemplary embodiment of the present specification has excellent performance by applying a compound having excellent crystallinity and excellent charge mobility to an organic semiconductor layer.

BRIEF DESCRIPTION OF DRAWINGS

FIGS. 1 to 4 are views illustrating an organic transistor according to an exemplary embodiment of the present invention.

FIG. 5 is a view illustrating an MS spectrum of Compound 1-b.

FIG. 6 is a view illustrating an MS spectrum of Compound 1-c.

FIG. 7 is a view illustrating NMR data of Chemical Formula 1-c.

FIG. 8 is a view illustrating an MS spectrum of Compound 1-d.

FIG. 9 is a view illustrating NMR data of Compound 1-d.

FIG. 10 is a view illustrating an MS spectrum of Compound 1-f.

FIG. 11 is a view illustrating NMR data of Compound 1-f.

FIG. 12 is a view illustrating an MS spectrum of Compound 1.

FIG. 13 is a view illustrating NMR data of Compound 1.

FIG. 14 is a view illustrating NMR data of Compound 2-b.

FIG. 15 is a view illustrating an MS spectrum of Compound 2-c.

FIG. 16 is a view illustrating NMR data of Compound 2-c.

FIG. 17 is a view illustrating an MS spectrum of Compound 2-d.

FIG. 18 is a view illustrating NMR data of Compound 2-d.

FIG. 19 is a view illustrating an MS spectrum of Compound 2-f.

FIG. 20 is a view illustrating NMR data of Compound 2-f.

FIG. 21 is a view illustrating an MS spectrum of Compound 2.

FIG. 22 is a view illustrating NMR data of Compound 2.

FIG. 23 is a view illustrating an MS spectrum of Compound 5-a.

FIG. 24 is a view illustrating NMR data of Compound 5-a.

FIG. 25 is a view illustrating an MS spectrum of Compound 5.

FIG. 26 is a view illustrating NMR data of Compound 5.

FIG. 27(a) is a view illustrating absorbance of Compound 1.

FIG. 27(b) is a view illustrating absorbance of Compound 2.

FIG. 27(c) is a view illustrating absorbance of Compound 5.

FIG. 28(a) is a view illustrating a measurement result of CV of Compound 1.

FIG. 28(b) is a view illustrating a measurement result of CV of Compound 2.

FIG. 28(c) is a view illustrating a measurement result of CV of Compound 5.

FIG. 29(a) is a view illustrating a measurement result of DSC of Compound 1.

FIG. 29(b) is a view illustrating a measurement result of DSC of Compound 2.

FIG. 29(c) is a view illustrating a measurement result of DSC of Compound 5.

FIG. 30(a) is a view illustrating an optical image of Compound 1 heat-treated at 100° C.

FIG. 30(b) is a view illustrating an optical image of Compound 2 heat-treated at 100° C.

FIG. 30(c) is a view illustrating an optical image of Compound 5 heat-treated at 100° C.

FIG. 30(d) is a view illustrating crystal size distributions of Compound 1, Compound 2, and Compound 5.

FIG. 31(a) is a view illustrating measurement results of XRD of Compound 1, Compound 2, and Compound 5.

FIG. 31(b) is a view illustrating measurement results of XRD of Compound 1 according to a heat treatment condition.

FIG. 31(c) is a view illustrating the measurement result of XRD of Compound 2 according to a heat treatment condition.

FIG. 31(d) is a view illustrating the measurement result of XRD of Compound 5 according to the heat treatment condition.

FIG. 32 is a view illustrating measurement results of GIWAXS of Compound 2 and Compound 5.

FIG. 33 is atomic force microscope (AFM) measurement results after Compounds 1, 2, and 5 are formed as a film.

FIG. 34 is a view illustrating an NMR spectrum of Compound 6.

FIG. 35 is a view illustrating an MS spectrum of Compound 6.

FIG. 36 is a view illustrating an NMR spectrum of Compound 7-b.

FIG. 37 is a view illustrating an MS spectrum of Compound 7-b.

FIG. 38 is a view illustrating an NMR spectrum of Compound 7.

FIG. 39 is a view illustrating an MS spectrum of Compound 7.

FIGS. 40 and 41 are views illustrating the evaluation of characteristics of an organic transistor according to an exemplary embodiment of the present specification.

FIGS. 42 and 43 are views illustrating the evaluation of characteristics of a gas sensor according to an exemplary embodiment of the present specification.

10: Substrate
20: Gate electrode
30: Insulating layer
40: Source electrode
50: Drain electrode
60: Organic semiconductor layer

BEST MODE

Hereinafter, the present specification will be described in detail.

The present specification provides an organic transistor including an organic semiconductor layer including the compound represented by Chemical Formula 1.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a nitrile group; a nitro group; an imide group; an amide group; a carbonyl group; an ester group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a siloxane group; a boron group; an amine group; an arylphosphine group; a phosphine oxide group; an aryl group; and a heterocyclic group, or being substituted with a substituent to which two or more substituents among the exemplified substituents are linked or having no substituent. For example, "the substituent to which two or more substituents are linked" may be a biphenyl group. That is, the biphenyl group may also be an aryl group, and may be interpreted as a substituent to which two phenyl groups are linked.

In the present specification,

means a moiety bonded to another substituent or a bonding portion.

In the present specification, a halogen group may be fluorine, chlorine, bromine, or iodine.

In the present specification, the number of carbon atoms of an imide group is not particularly limited, but is preferably 1 to 30. Specifically, the imide group may be a compound having the following structures, but is not limited thereto.

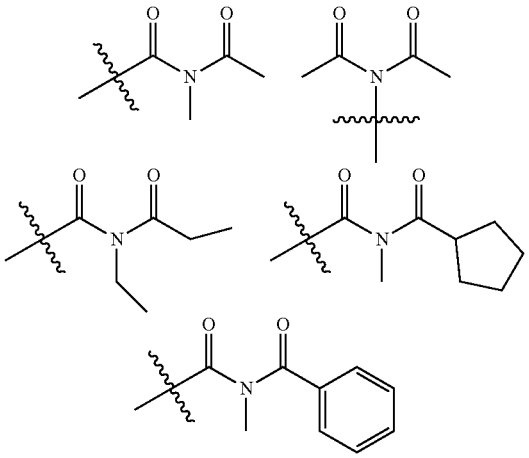

In the present specification, for an amide group, the nitrogen of the amide group may be substituted with hydrogen, a straight, branched, or cyclic alkyl group having 1 to 30 carbon atoms, or an aryl group having 6 to 30 carbon atoms. Specifically, the amide group may be a compound having the following structural formulae, but is not limited thereto.

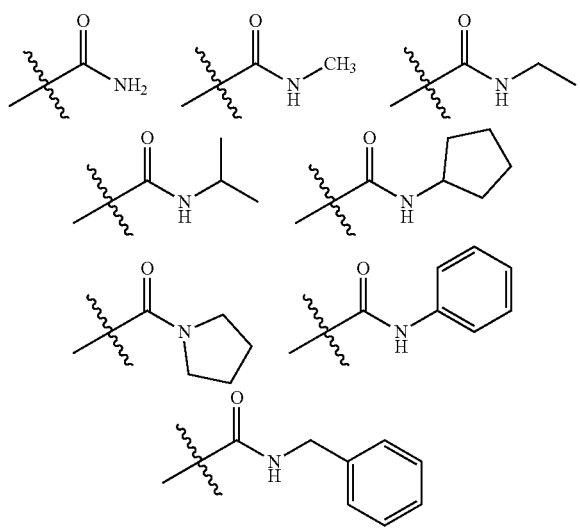

In the present specification, the number of carbon atoms of a carbonyl group is not particularly limited, but is preferably 1 to 30. Specifically, the carbonyl group may be a compound having the following structures, but is not limited thereto.

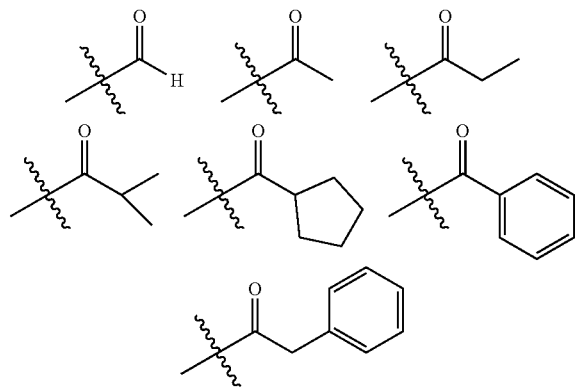

In the present specification, for an ester group, the oxygen of the ester group may be substituted with a straight, branched, or cyclic alkyl group having 1 to 25 carbon atoms, or an aryl group having 6 to 30 carbon atoms. Specifically, the ester group may be a compound having the following structural formulae, but is not limited thereto.

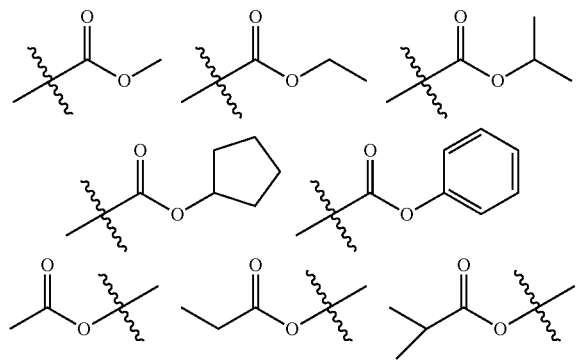

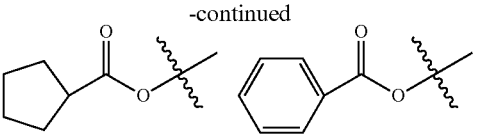

In the present specification, the alkyl group may be straight or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, an amine group may be selected from the group consisting of —NH₂; an alkylamine group; an N-arylalkylamine group; an arylamine group; an N-arylheteroarylamine group; an N-alkylheteroarylamine group; and a heteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, and the like, but are not limited thereto.

In the present specification, an N-alkylarylamine group means an amine group in which an alkyl group and an aryl group are substituted with N of the amine group.

In the present specification, an N-arylheteroarylamine group means an amine group in which an N of the amine group is substituted with aryl group and a heteroaryl group.

In the present specification, an N-alkylheteroarylamine group means an amine group in which an N of the amine group is substituted with alkyl group and a heteroarylamine group.

In the present specification, the alkyl group in the alkylamine group, the N-arylalkylamine group, the alkylthioxy group, the alkylsulfoxy group, and the N-alkylheteroarylamine group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include methyl, an ethylsulfoxy group, a propylsulfoxy group, a butylsulfoxy group, and the like, but the examples are not limited thereto.

In the present specification, the alkenyl group may be straight or branched, and the number of carbon atoms thereof is not particularly limited, but is preferably 2 to 30. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —$BR_{100}R_{200}$, and $R_{100}$ and $R_{200}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, dinaphthylphosphine oxide, and the like, but are not limited thereto.

In the present specification, an aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may be bonded to each other to form a ring.

When the fluorenyl group is substituted, the fluorenyl group may be

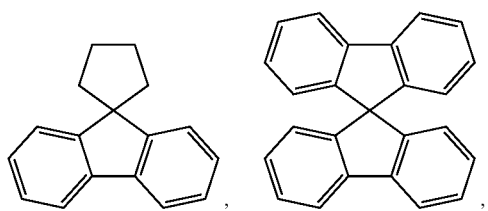

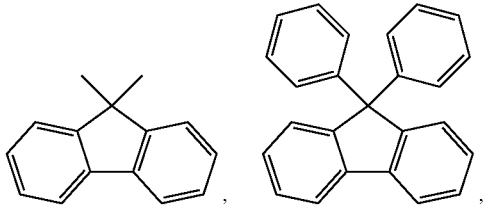

and the like. However, the fluorenyl group is not limited thereto.

In the present specification, the aryl group in the aryloxy group, the arylthioxy group, the arylsulfoxy group, the N-arylalkylamine group, the N-arylheteroarylamine group, and the arylphosphine group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group. For example, the aryl group in the arylamine group may be selected from the above-described examples of the aryl group.

In the present specification, a heterocyclic group and a heteroaryl group include one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and the heterocyclic group and the heteroaryl group may be monocyclic or polycyclic. Examples of the heterocyclic group and the heteroaryl group include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a phenothiazinyl group, a dibenzofuranyl group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include a monocyclic heteroaryl group, a polycyclic heteroaryl group, or both a monocyclic heteroaryl group and a polycyclic heteroaryl group. For example, the heteroaryl group in the heteroarylamine group may be selected from the above-described examples of the heteroaryl group.

In the present specification, examples of the heteroaryl group in the N-arylheteroarylamine group and the N-alkylheteroarylamine group are the same as the above-described examples of the heteroaryl group.

In the present specification, the [Push] acts as an electron donor in a compound.

In the present specification, the [Pull1] and the [Pull2] act as an electron acceptor in a compound.

In the present specification, in Chemical Formula 1, [Push] has oxidation characteristics in the compound.

In the present specification, in Chemical Formula 1, [Pull1] and [Pull2] have reduction characteristics in the compound.

In the present specification, when the [Push], the [Pull1], and the [Pull2] are measured by using cyclic voltammetry (CV), the [Push] has relative oxidation characteristics as compared to the [Pull1] and the [Pull2], and the [Pull1] and the [Pull2] have relative reduction characteristics as compared to the [Push].

However, in the present specification, the oxidation characteristics and the reduction characteristics are relative, and the [Push] has oxidation characteristics, but may also have reduction characteristics, and the [Pull1] and the [Pull2] have reduction characteristics, but may also have oxidation characteristics.

In the compound according to an exemplary embodiment of the present specification, [Push] relatively acts as an electron donor, and [Pull1] and [Pull2] act as an electron acceptor. In this case, electrons in the lowest unoccupied molecular orbital (LUMO) state are relatively localized in [Pull1] and [Pull2]. For this reason, there is polarization between [Push] and [Pull1] and between [Push] and [Pull2].

The present specification may maximize localization of electrons by introducing a linker, which has relatively excellent planarity and has a conjugation, between the [Push] and the [Pull1] and between the [Push] and the [Pull2], to allow the electrons to rapidly move in the direction of [Pull] in the compound. In this case, the formed excitons may rapidly move in the molecule, and polarization of the excitons may be maximized, thereby having low band gap characteristics.

In the present specification, an energy level means a size of energy. Accordingly, even when the energy level is expressed in a negative (−) direction from a vacuum level, it is interpreted that the energy level means an absolute value of the corresponding energy value. For example, the HOMO energy level means a distance from the vacuum level to the highest occupied molecular orbital. Further, the LUMO energy level means the distance from the vacuum level to the lowest unoccupied molecular orbital.

According to an exemplary embodiment of the present specification, R1 to R16, R101 to R116, and R201 to R204 in Chemical Formula 1 are the same as or different from each other, and are each independently hydrogen; a halogen group; a substituted or unsubstituted alkyl group; a substituted or unsubstituted cycloalkyl group; a substituted or unsubstituted alkoxy group; a substituted or unsubstituted silyl group; a substituted or unsubstituted siloxane group; a substituted or unsubstituted amine group; a substituted or unsubstituted aryl group; or a substituted or unsubstituted heterocyclic group, and at least one of R1 to R16 and R101 to R116 is a substituted or unsubstituted silyl group, or a substituted or unsubstituted siloxane group.

According to an exemplary embodiment of the present specification, R1 to R16, R101 to R116, and R201 to R204 in Chemical Formula 1 are the same as or different from each other, and are each independently hydrogen; a substituted or unsubstituted alkyl group; a substituted or unsubstituted silyl group; or a substituted or unsubstituted siloxane group, and at least one of R1 to R16 and R101 to R116 is a substituted or unsubstituted silyl group, or a substituted or unsubstituted siloxane group.

According to an exemplary embodiment of the present specification, in Chemical Formula 1, X1 to X6 are the same as or different from each other, and are each independently O, SiRR', or S, and R and R' are the same as those described above.

According to an exemplary embodiment of the present specification, in Chemical Formula 1, Y1 to Y4 are the same as or different from each other, and are each independently CR'', N, or SiR'', and R'' is the same as that described above.

According to an exemplary embodiment of the present specification, in Chemical Formula 1, X11 to X28 are the same as or different from each other, and are each independently O, SiRR', or S, and R and R' are the same as those described above.

In the present specification, including a substituted or unsubstituted silyl group or a substituted or unsubstituted siloxane group means being substituted with not only a substituted or unsubstituted silyl group or a substituted or unsubstituted siloxane group, but also a silyl group or a siloxane group. For example, the substituent may be an alkyl group substituted with a silyl group and an alkoxy group substituted with a silyl group.

In the present specification, the compound of Chemical Formula 1 includes a substituted or unsubstituted silyl group or a substituted or unsubstituted siloxane group in the side-chain of the compound, and thus has an effect of improving the crystallinity.

In the present specification, the compound of Chemical Formula 1 includes a substituted or unsubstituted silyl group or a substituted or unsubstituted siloxane group in the side-chain of the compound, and thus has an effect of improving the performance of an organic transistor, such as charge mobility and on-off ratio, when applied to an organic semiconductor layer of the organic transistor.

According to an exemplary embodiment of the present specification, Chemical Formula 1 may be represented by the following Chemical Formula 1-1 or Chemical Formula 1-2.

[Chemical Formula 1-1]

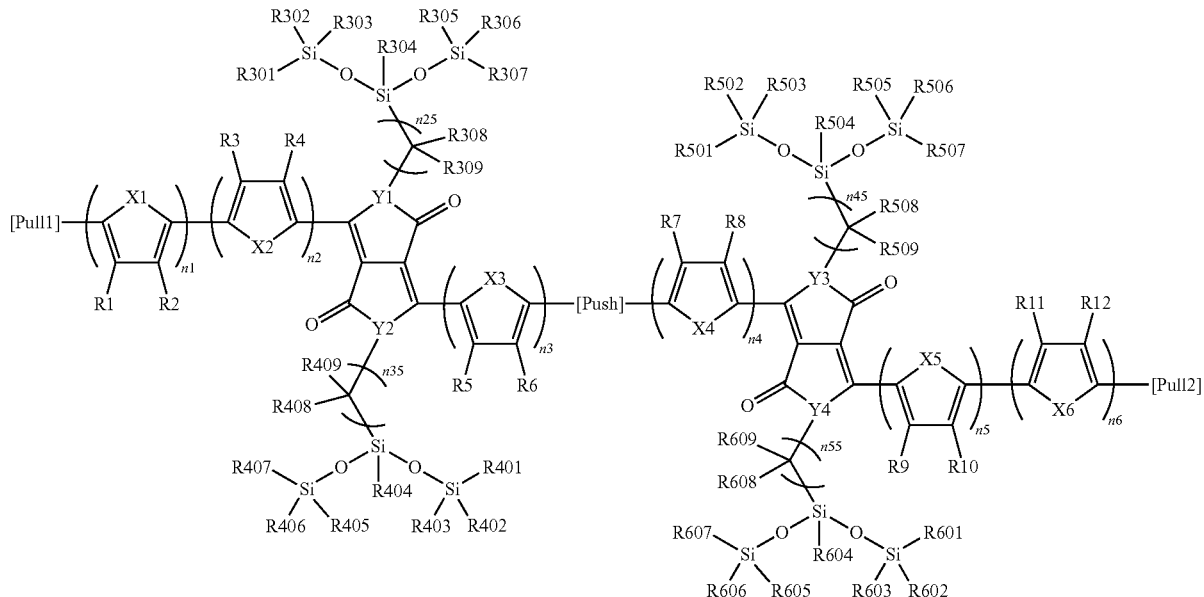

[Chemical Formula 1-2]

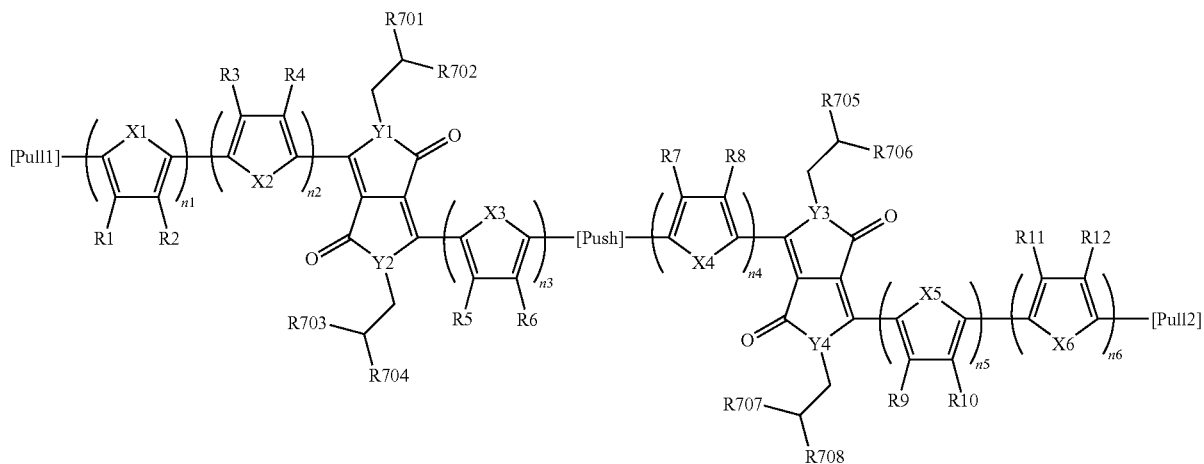

In Chemical Formulae 1-1 and 1-2, the definitions of n1 to n6, [Push], [Pull1], [Pull2], X1 to X6, Y1 to Y4, and R1 to R12 are the same as those in Chemical Formula 1, n25, n35, n45, and n55 are each an integer from 0 to 5, when n25, n35, n45, and n55 are each 2 or more, two or more structures in the parenthesis are the same as or different from each other, and R301 to R309, R401 to R409, R501 to R509, R601 to R609, and R701 to R708 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted siloxane group; a substituted or unsubstituted boron group; a substituted or unsubstituted amine group; a substituted or unsubstituted aryl group; or a substituted or unsubstituted heterocyclic group.

According to an exemplary embodiment of the present specification, Chemical Formula 1 may be represented by any one of the following Chemical Formulae 1-3 to 1-8.

[Chemical Formula 1-3]
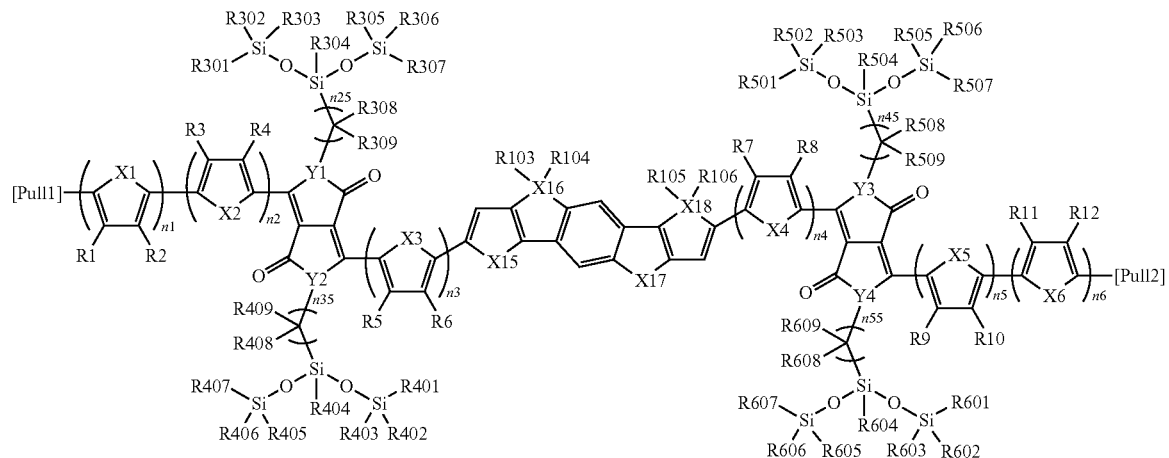
[Chemical Formula 1-4]
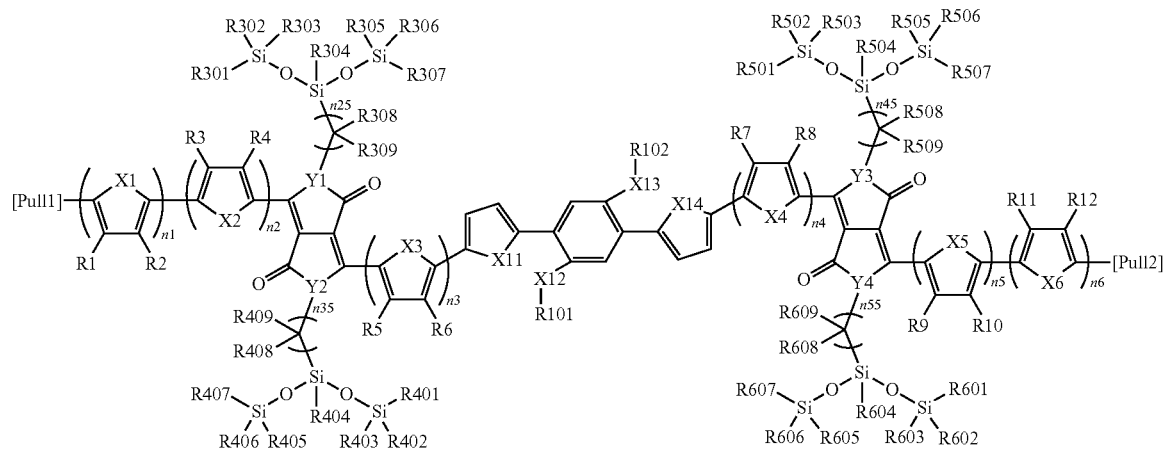
[Chemical Formula 1-5]
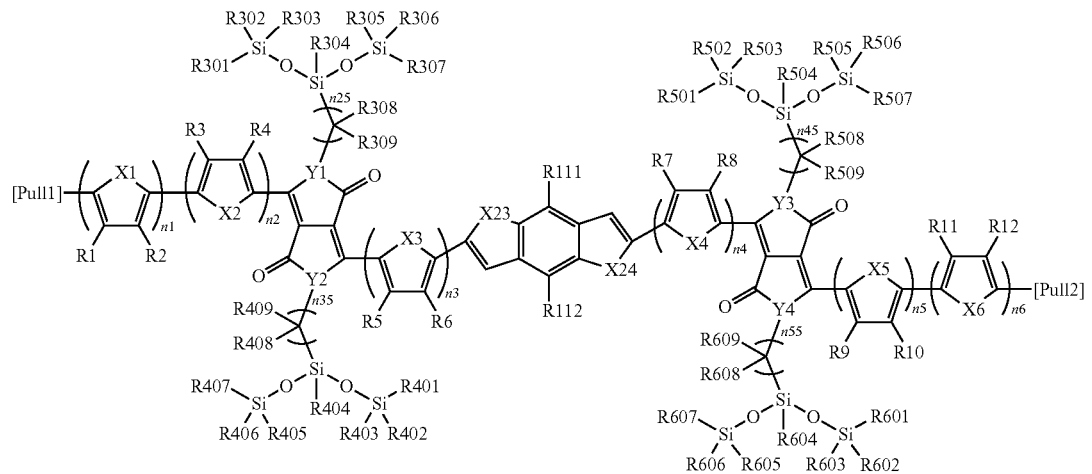

[Chemical Formula 1-6]

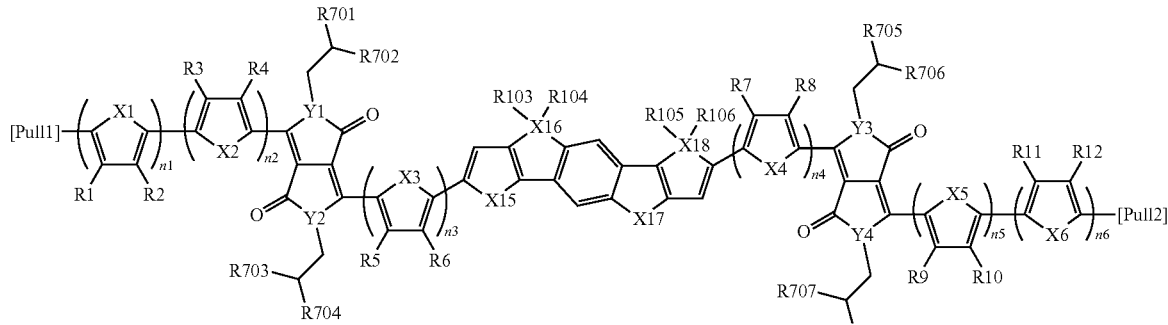

[Chemical Formula 1-7]

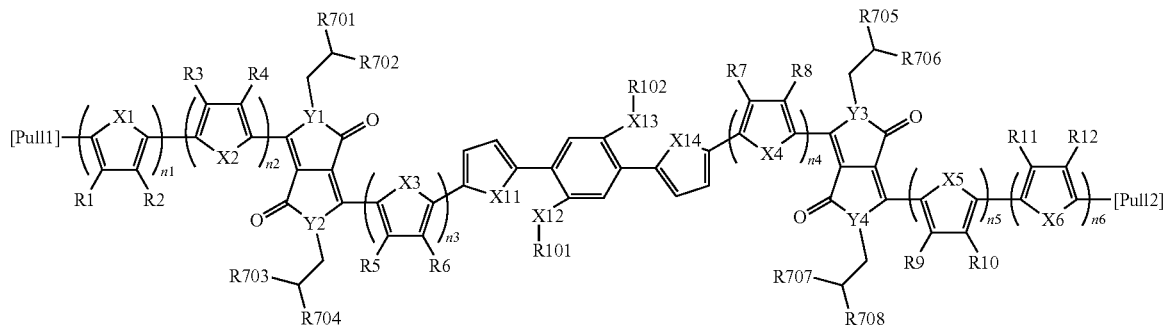

[Chemical Formula 1-8]

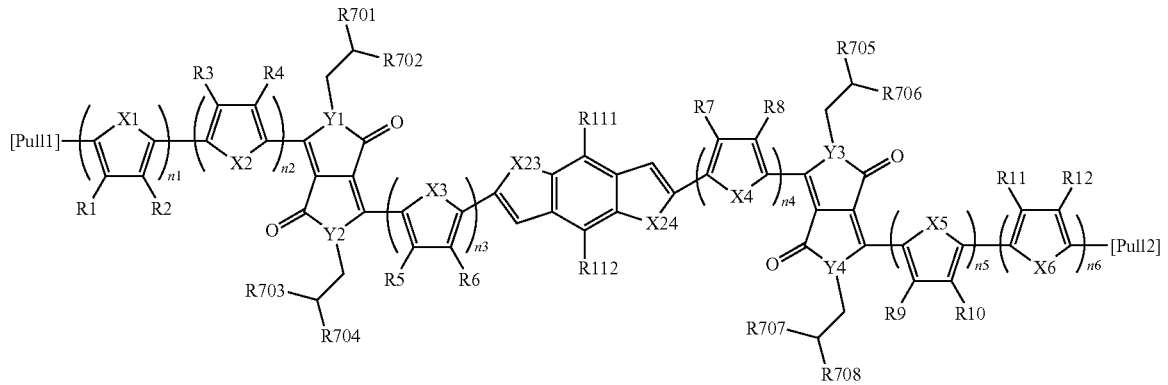

In Chemical Formulae 1-3 to 1-8, the definitions of n1 to n6, [Push], [Pull1], [Pull2], X1 to X6, X11 to X18, X23, X24, Y1 to Y4, R1 to R12, R101, R102, R111, and R112 are the same as those in Chemical Formula 1, n25, n35, n45, and n55 are each an integer from 0 to 5, when n25, n35, n45, and n55 are each 2 or more, two or more structures in the parenthesis are the same as or different from each other, and R301 to R309, R401 to R409, R501 to R509, R601 to R609, and R701 to R708 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted siloxane group; a substituted or unsubstituted boron group; a substituted or unsubstituted amine group; a substituted or unsubstituted aryl group; or a substituted or unsubstituted heterocyclic group.

In an exemplary embodiment of the present specification, R301 to R309, R401 to R409, R501 to R509, R601 to R609, and R701 to R708 are the same as or different from each other, and are each independently hydrogen; a halogen group; a substituted or unsubstituted alkyl group; a substituted or unsubstituted cycloalkyl group; a substituted or unsubstituted alkoxy group; a substituted or unsubstituted silyl group; a substituted or unsubstituted siloxane group; a substituted or unsubstituted amine group; a substituted or unsubstituted aryl group; or a substituted or unsubstituted heterocyclic group.

In an exemplary embodiment of the present specification, R301 to R309, R401 to R409, R501 to R509, R601 to R609, and R701 to R708 are the same as or different from each other, and are each independently hydrogen; a substituted or unsubstituted alkyl group; a substituted or unsubstituted silyl group; or a substituted or unsubstituted siloxane group.

In an exemplary embodiment of the present specification, R301 to R309, R401 to R409, R501 to R509, R601 to R609, and R701 to R708 are the same as or different from each other, and are each independently hydrogen; or a substituted or unsubstituted alkyl group.

In an exemplary embodiment of the present specification, R301 to R309, R401 to R409, R501 to R509, R601 to R609, and R701 to R708 are the same as or different from each other, and are each independently hydrogen; or a substituted or unsubstituted straight or branched alkyl group having 1 to 30 carbon atoms.

In an exemplary embodiment of the present specification, R301 to R309, R401 to R409, R501 to R509, R601 to R609, and R701 to R708 are the same as or different from each other, and are each independently hydrogen; or a substituted or unsubstituted straight or branched alkyl group having 1 to 20 carbon atoms.

In an exemplary embodiment of the present specification, R301 to R309, R401 to R409, R501 to R509, R601 to R609, and R701 to R708 are the same as or different from each other, and are each independently hydrogen; or a substituted or unsubstituted straight or branched alkyl group having 1 to 10 carbon atoms.

In an exemplary embodiment of the present specification, R301 to R309, R401 to R409, R501 to R509, R601 to R609, and R701 to R708 are the same as or different from each other, and are each independently hydrogen; or a substituted or unsubstituted straight alkyl group having 1 to 5 carbon atoms.

In an exemplary embodiment of the present specification, R301 to R309, R401 to R409, R501 to R509, and R601 to R609 are the same as or different from each other, and are each independently hydrogen; or a substituted or unsubstituted methyl group.

In an exemplary embodiment of the present specification, X1 is S.

In an exemplary embodiment of the present specification, X2 is S.

In an exemplary embodiment of the present specification, X3 is S.

In an exemplary embodiment of the present specification, X4 is S.

In an exemplary embodiment of the present specification, X5 is S.

In an exemplary embodiment of the present specification, X6 is S.

In an exemplary embodiment of the present specification, Y1 is N.

In an exemplary embodiment of the present specification, Y2 is N.

In an exemplary embodiment of the present specification, Y3 is N.

In an exemplary embodiment of the present specification, Y4 is N.

In an exemplary embodiment of the present specification, X11 is S.

In an exemplary embodiment of the present specification, X12 is O.

In an exemplary embodiment of the present specification, X13 is O.

In an exemplary embodiment of the present specification, X14 is S.

In an exemplary embodiment of the present specification, X15 is S.

In an exemplary embodiment of the present specification, X16 is Si.

In an exemplary embodiment of the present specification, X17 is Si.

In an exemplary embodiment of the present specification, X18 is S.

In an exemplary embodiment of the present specification, X23 is S.

In an exemplary embodiment of the present specification, X24 is S.

According to an exemplary embodiment of the present specification, the [Pull1] and the [Pull2] are each

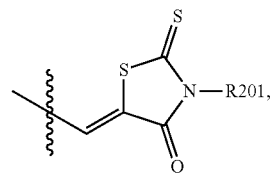

and the definition of R201 is the same as that defined in Chemical Formula 1.

In an exemplary embodiment of the present specification, the [Pull1] and the [Pull2] are each

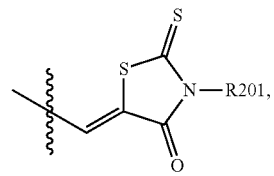

and R201 is a substituted or unsubstituted alkyl group.

In an exemplary embodiment of the present specification, R201 is a straight or branched alkyl group having 1 to 30 carbon atoms.

In an exemplary embodiment of the present specification, R201 is a straight or branched alkyl group having 1 to 20 carbon atoms.

In an exemplary embodiment of the present specification, R201 is a straight alkyl group having 1 to 10 carbon atoms.

In an exemplary embodiment of the present specification, R201 is an octyl group.

In an exemplary embodiment of the present specification, R201 is an ethyl group.

According to an exemplary embodiment of the present specification, Chemical Formula 1 is any one of the following compounds.

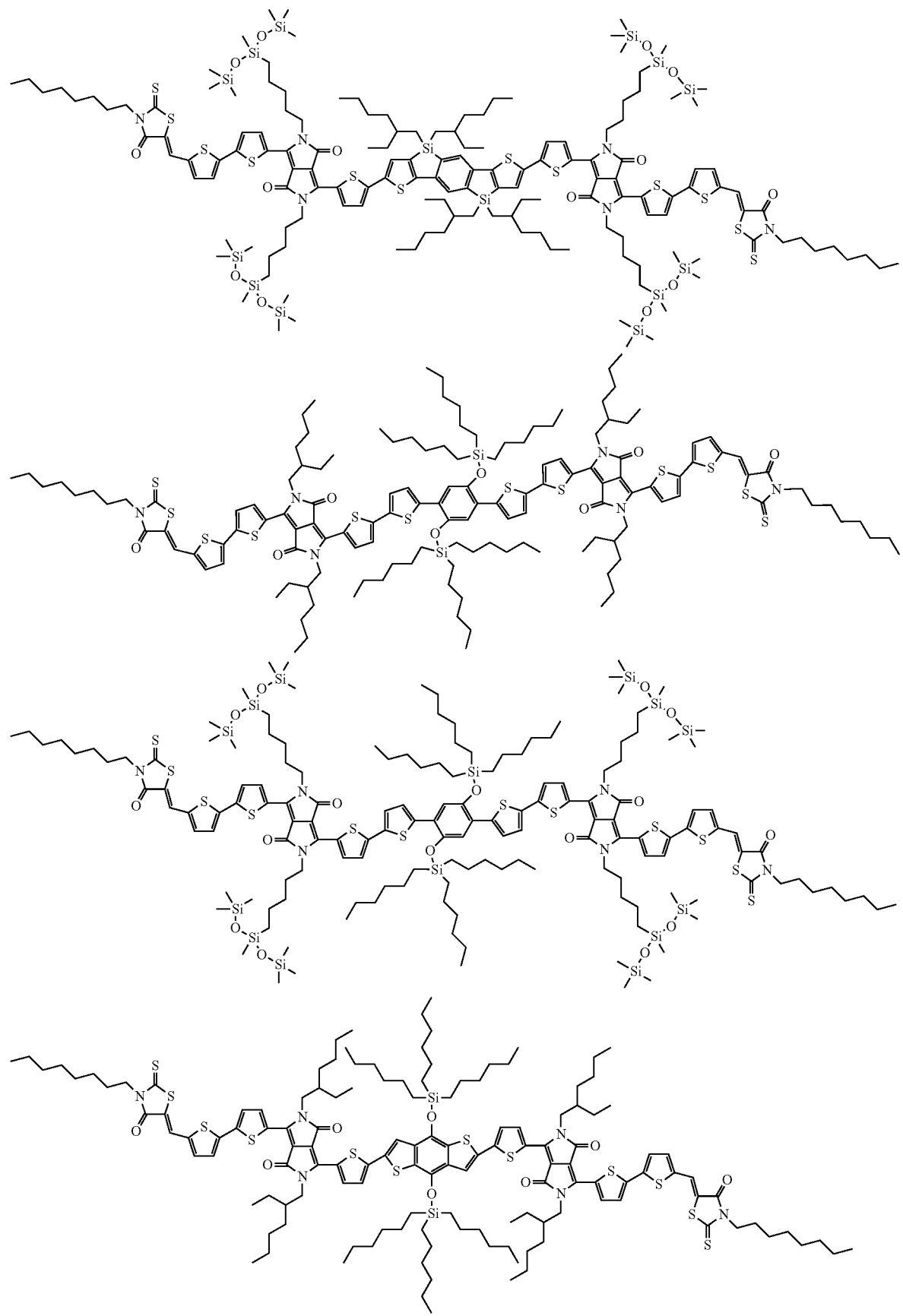

25
-continued
26
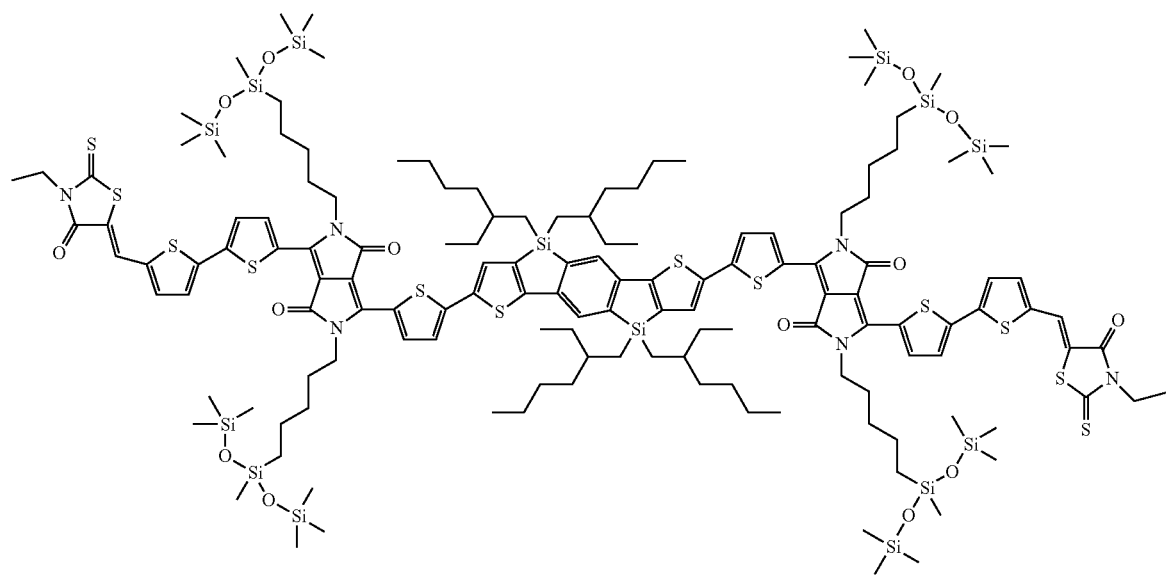
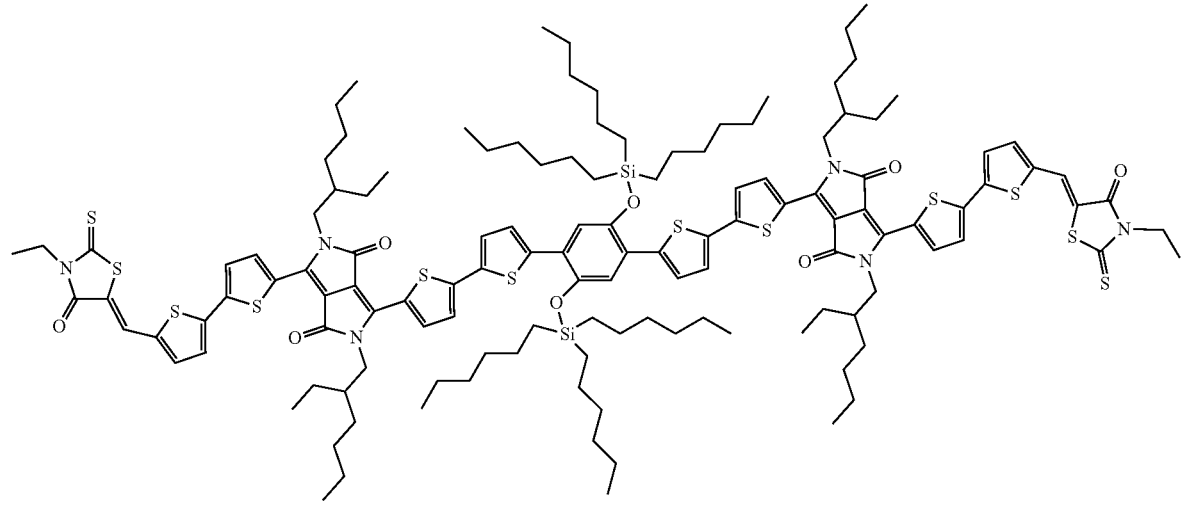
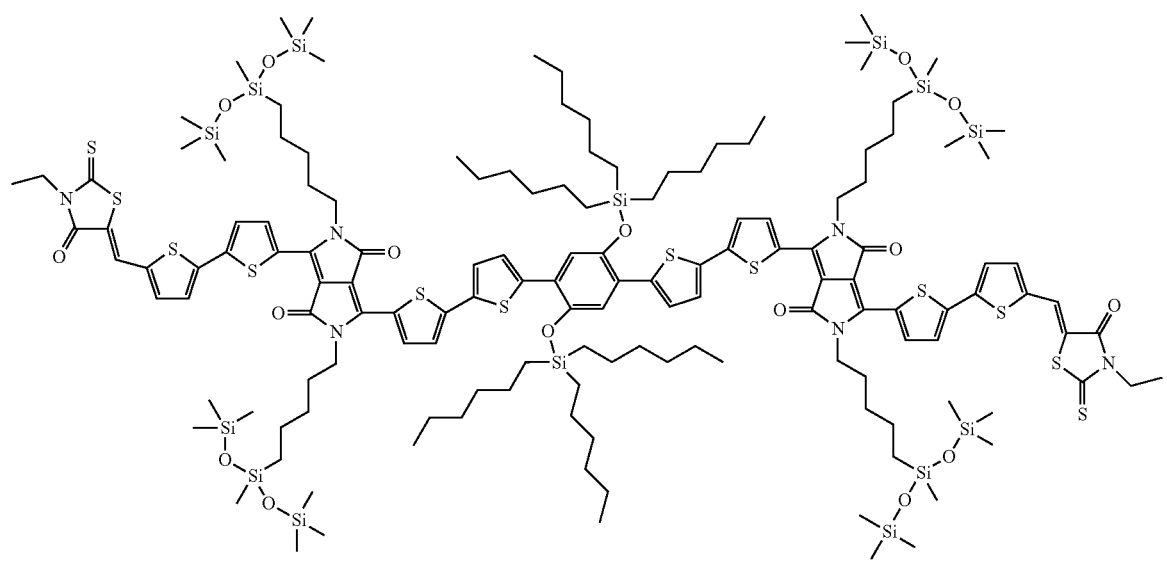

-continued

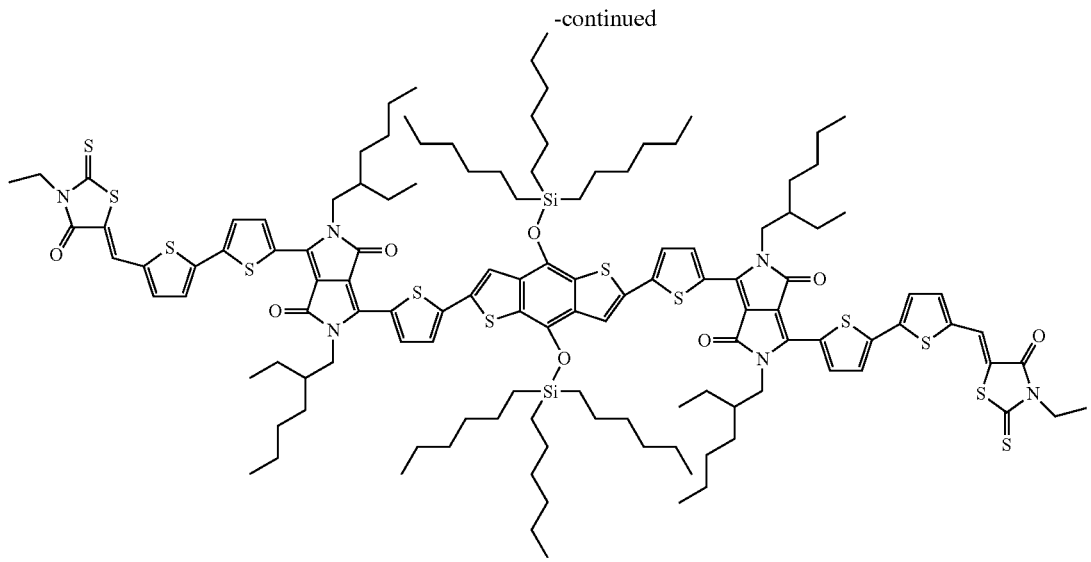

The compound according to an exemplary embodiment of the present specification includes a substituted or unsubstituted silyl group or a substituted or unsubstituted siloxane group in the side-chain of the compound, and thus has an effect of improving the crystallinity.

Since the compound according to an exemplary embodiment of the present specification includes a structure which is a bulky side chain, the solubility may be improved.

Further, the compound according to an exemplary embodiment of the present specification may impart elasticity. In this case, the compound may be used as a material for a flexible device.

The compound according to an exemplary embodiment of the present specification includes a substituted or unsubstituted silyl group or a substituted or unsubstituted siloxane group in the side-chain thereof, and thus has an effect in that when the compound is applied to an organic semiconductor layer of an organic transistor, the performance of the organic transistor, such as charge mobility and on/off ratio, is improved as compared to the case where a compound, which does not include a substituted or unsubstituted silyl group or a substituted or unsubstituted siloxane group, is applied to an organic transistor.

An exemplary embodiment of the present specification provides an organic transistor including a gate source, a source electrode, a drain electrode, and an insulating layer, which is brought into contact with the organic semiconductor layer.

In the present specification, a method for manufacturing the organic semiconductor layer is not particularly limited as long as the method is used in the art, and the organic semiconductor layer may be manufactured by using a vacuum deposition method, sputtering, E-beam, thermal deposition, spin coating, screen printing, inkjet printing, doctor blade, or a gravure printing method.

In the present specification, the organic transistor may have a top gate structure. Specifically, a source electrode and a drain electrode are first formed on a substrate, and then an organic semiconductor layer, an insulating layer, and a gate electrode may be sequentially formed. FIG. 1 illustrates a structure of the organic transistor.

In the present specification, the organic transistor may have a bottom contact structure in the bottom gate structure. Specifically, a gate electrode and an insulating layer may be sequentially formed on a substrate, and then a source electrode and a drain electrode may be formed on the insulating layer, and finally, an organic semiconductor layer may be formed on the source electrode and the drain electrode. FIGS. 2 and 3 illustrate a structure of the organic transistor.

In the present specification, the organic transistor may have a top contact structure in the bottom gate structure. Specifically, a gate electrode and an insulating layer may be sequentially formed on a substrate, and then an organic semiconductor layer may be formed on the insulating layer, and finally, a source electrode and a drain electrode may be formed on the organic semiconductor layer. FIG. 4 illustrates a structure of the organic transistor.

In the present specification, as the substrate, a material used in the art may be used. For example, it is possible to use a plastic substrate or a glass substrate such as glass, polyethylenenaphthalate (PEN), polyethyleneterephthalate (PET), polycarbonate (PC), polyvinylalcohol (PVP), polyacrylate, polyimide, polynorbornene, and polyethersulfone (PES).

Further, as a surface treatment between the source electrode and the drain electrode and the organic semiconductor layer, 1,1,1,3,3,3-hexamethyldisilazane (HMDS), octyltrichlorosilane (OTS), or octadecyltrichlorosilane (OTDS) may be coated or may not be coated.

In the present specification, materials for the gate electrode, the source electrode, and the drain electrode are not particularly limited as long as the materials are used in the art. For example, the material may be a conductive material. Specifically, the material may be a material selected from the group consisting of gold (Au), silver (Ag), aluminum (Al), nickel (Ni), chromium (Cr), and indium tin oxide (ITO).

In the present specification, the source electrode and the drain electrode may be manufactured by using E-beam and a photolithography method, but the manufacturing method is not limited thereto.

In the present specification, a material for the insulating layer is not particularly limited as long as the material is used in the art. For example, it is possible to use silicon dioxide ($SiO_2$) which has a high insulation rate and may be easily formed on a gate electrode.

In the present specification, a method for manufacturing the insulating layer is not particularly limited as long as the method is used in the art, and for example, the insulating layer may be manufactured by using E-beam and a photolithography method, but the manufacturing method is not limited thereto.

In the present specification, the organic transistor may be formed as a single layer or a multilayer.

The present specification provides a gas sensor to which the above-described organic transistor is applied. Specifically, the gas sensor may use characteristics in which electrical characteristics are changed by exposing the organic transistor to a specific gas to bring the organic semiconductor layer of the organic transistor into contact with a gas material.

In an exemplary embodiment of the present specification, the gas sensor is provided with a gate electrode, a source electrode, a drain electrode, an insulating layer, and an organic semiconductor layer including a compound including the unit of Chemical Formula 1.

In an exemplary embodiment of the present specification, the gas sensor may further include a carbon-based material in the organic semiconductor layer.

In the present specification, the carbon-based material means one or more selected from the group consisting of carbon black, carbon nanotube (CNT), graphite, graphene, activated carbon, mesoporous carbon, carbon fiber, and carbon nano wire.

In an exemplary embodiment of the present specification, the gas sensor senses ammonia ($NH_3$), ethylene ($C_2H_4$), formaldehyde (HCHO), hydrofluoric acid (HF), nitrogen oxide, sulfur oxide and/or ethanol.

In an exemplary embodiment of the present specification, it is possible to measure sensitivity of the gas sensor by exposing the gas sensor to the saturated vapor pressure of each gas and connecting the sensor to a probe station, but the measurement method is not limited thereto, and it is possible to evaluate characteristics of the gas sensor by means of devices which are connected to the electrodes of the transistor used in the art and thus may measure the current value.

In the present specification, "sensing" means a change in density of conduction electrons on a surface of the organic semiconductor layer by interaction of the surface of the organic semiconductor layer of the gas sensor with a gas.

In an exemplary embodiment of the present specification, the gas sensor may have sensitivity to sulfur oxide at 0.1 ppm or more as compared to the air. Specifically, the gas sensor may have sensitivity to sulfur oxide at 0.1 ppm or more and 90% or less as compared to the air.

In the present specification, "sensitivity at 0.1 ppm or more as compared to the air" may mean that a gas can be sensed if present in an amount of 0.1 ppm or more in the air. For example, "sensitivity to sulfur oxide at 0.1 ppm or more as compared to the air" may mean that sulfur oxide can be sensed if present in an amount of 0.1 ppm or more in the air.

In the present specification, 1% is 10,000 ppm.

In an exemplary embodiment of the present specification, the gas sensor may have sensitivity to ammonia ($NH_3$) at 0.1 ppm or more as compared to the air. Specifically, the gas sensor may have sensitivity to ammonia ($NH_3$) at 0.1 ppm or more and 90% or less as compared to the air.

In an exemplary embodiment of the present specification, the gas sensor may have sensitivity to ethylene ($C_2H_4$) at 0.1 ppm or more as compared to the air. Specifically, the gas sensor may have sensitivity to ethylene ($C_2H_4$) at 0.1 ppm or more and 90% or less as compared to the air.

In an exemplary embodiment of the present specification, the gas sensor may have sensitivity to ethanol at more than 0 and 20% or less as compared to the air.

In an exemplary embodiment of the present specification, the gas sensor may have sensitivity to formaldehyde (HCHO) at 0.1 ppm or more as compared to the air. Specifically, the gas sensor may have sensitivity to formaldehyde (HCHO) at 0.1 ppm or more and 90% or less as compared to the air.

In an exemplary embodiment of the present specification, the gas sensor may have sensitivity to hydrofluoric acid (HF) at 0.1 ppm or more as compared to the air. Specifically, the gas sensor may have sensitivity to hydrofluoric acid (HF) at 0.1 ppm or more and 90% or less as compared to the air.

In an exemplary embodiment of the present specification, the gas sensor may have sensitivity to nitrogen oxide at 0.1 ppm or more as compared to the air. Specifically, the gas sensor may have sensitivity to nitrogen oxide at 0.1 ppm or more and 90% or less as compared to the air.

[Mode for Invention]

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Preparation Example 1. Preparation of Compound 1

(1) Preparation of Compound 1-b

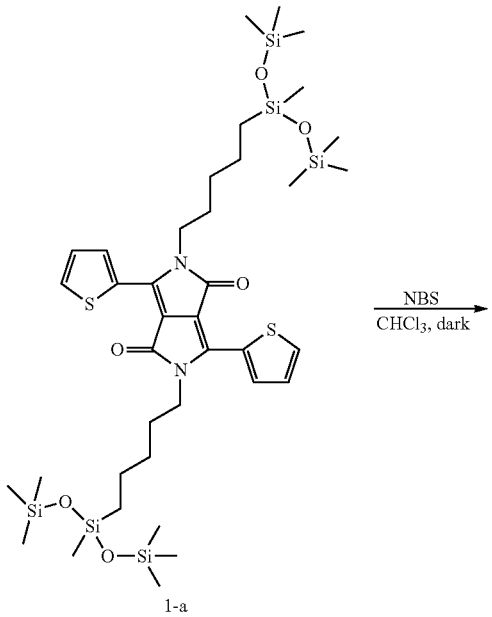

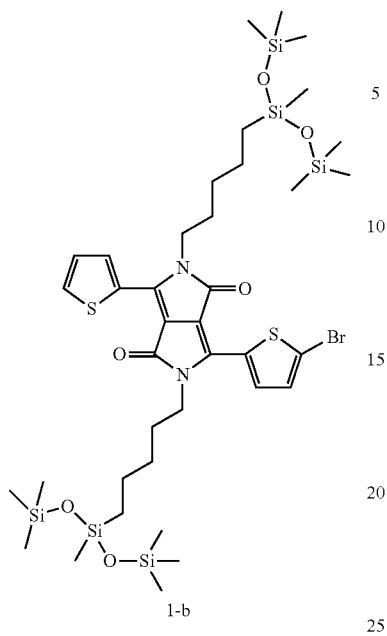

1-b

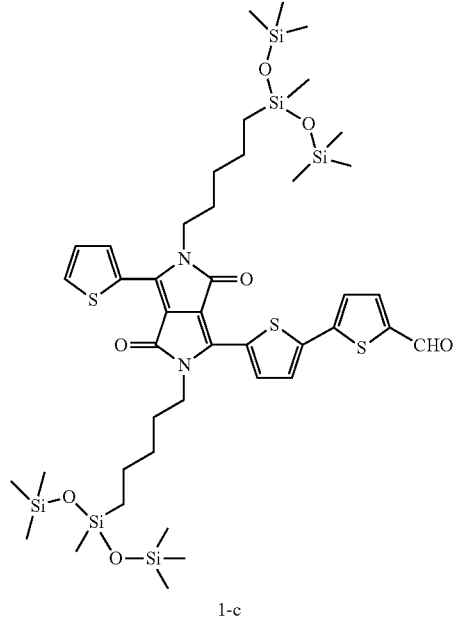

1-c

After 1-a (5.29 g, 6 mmol) was dissolved in 150 mL of chloroform (CHCl₃), N-bromosuccinimide (NBS) (1.28 g, 7.2 mmol) was injected thereinto at room temperature, and then the resulting mixture was stirred for 48 hours. After reaction, the reactant was added to 250 mL of water, and an extraction was performed with dichloromethane. Thereafter, the remaining water was removed over magnesium sulfate (MgSO₄), and then the solvent was removed under reduced pressure. The remaining product was purified with silica column (hexane:dichloromethane=2:1 (eluent)) to obtain Compound 1-b. (Yield: 71%)

FIG. 5 is a view illustrating an MS spectrum of Compound 1-b.

(2) Preparation of Compound 1-c

Compound 1-b (4.092 g, 4.26 mmol) and 2-aldehyde-thiophene boronic ester (0.935 g, 6 mmol) were dissolved in 200 mL of tetrahydrofuran (THF) and 50 mL of 2 M potassium carbonate (K₂CO₃), a tetrakis(triphenylphosphine)palladium (0) (Pd(PPh₃)₄) catalyst (0.2427 g, 0.21 mmol) was added thereto, and the resulting mixture was stirred at 70° C. for 72 hours. After reaction, an extraction was performed with dichloromethane, the remaining water was removed over magnesium sulfate (MgSO₄), and then the solvent was removed under reduced pressure. The remaining product was purified with silica column (hexane:dichloromethane=10:1 to 1:1 (eluent)) to obtain Compound 1-c. (Yield: 79%)

FIG. 6 is a view illustrating an MS spectrum of Compound 1-c.

FIG. 7 is a view illustrating an NMR spectrum of Compound 1-c.

(3) Preparation of Compound 1-d

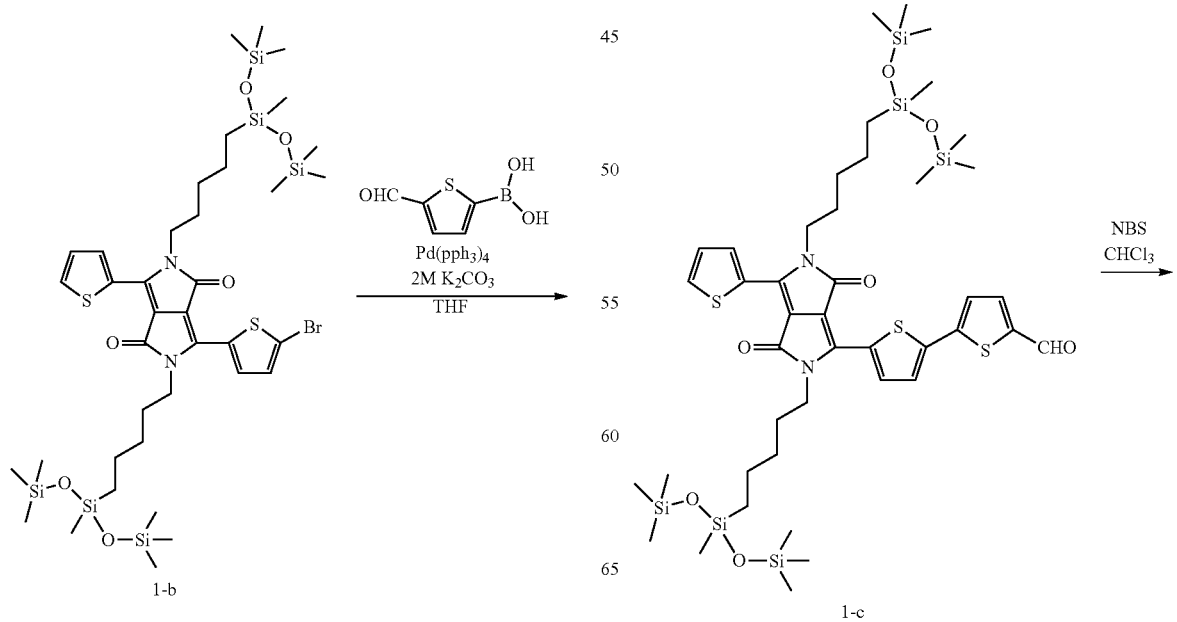

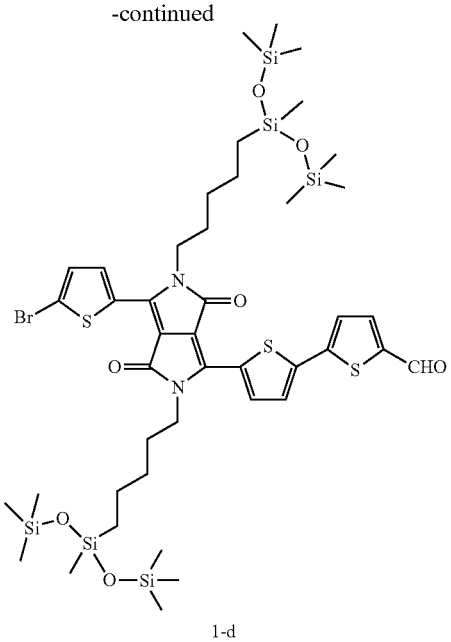

1-d

Compound 1-c (3 g, 3.03 mmol) was dissolved in 80 mL of chloroform (CHCl$_3$), N-bromosuccinimide (NBS) (0.59 g, 3.33 mmol) was added thereto, and the resulting mixture was stirred at room temperature for 48 hours. After reaction, an extraction was performed with dichloromethane, the remaining water was removed over magnesium sulfate (MgSO$_4$), and then the solvent was removed under reduced pressure. The remaining product was purified with silica column (hexane:dichloromethane=10:1 to 1:1 (eluent)) to obtain Compound 1-d. (Yield: 81%)

FIG. 8 is a view illustrating an MS spectrum of Compound 1-d.

FIG. 9 is a view illustrating an NMR spectrum of Compound 1-d.

(4) Preparation of Compound 1-f

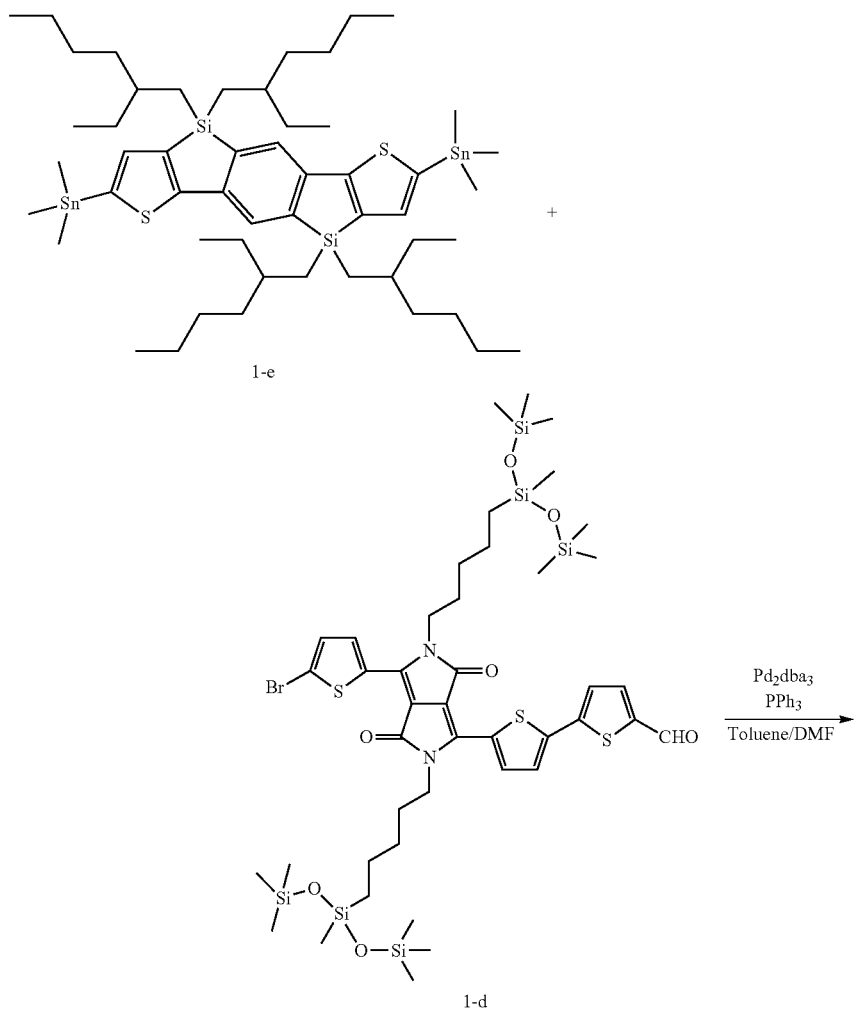

-continued

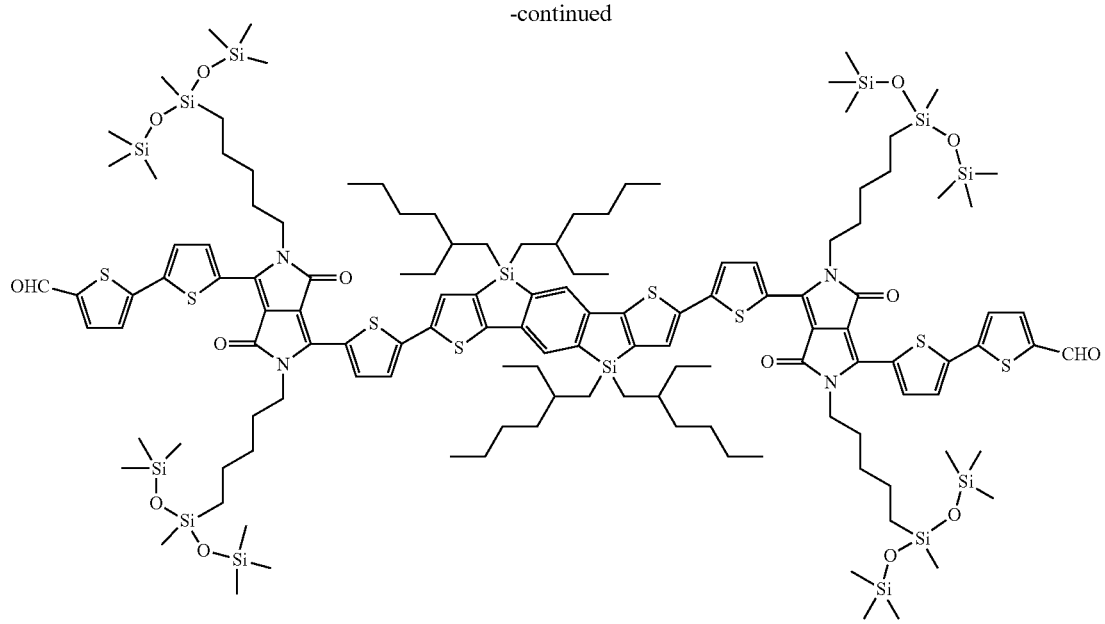

1-f

Compound 1-e (1.18 g, 1.10 mmol) and Compound 1-d (2.623 g, 2.45 mmol) were dissolved in 60 mL of toluene and 6 mL of dimethylformamide (DMF), a tris(dibenzylideneacetone)dipalladium(0) ($Pd_2dba_3$) catalyst (0.0504 g, 0.055 mmol) and a triphenylphosphine ($PPh_3$) ligand (0.0577 g, 0.22 mmol) were added thereto, and the resulting mixture was stirred at 110° C. for 48 hours. After reaction, an extraction was performed with dichloromethane, the remaining water was removed over magnesium sulfate ($MgSO_4$), and then the solvent was removed under reduced pressure. The remaining product was subjected to silica column (eluent: hexane) to obtain Compound 1-f. (Yield: 57%)

FIG. 10 is a view illustrating an MS spectrum of Compound 1-f.

FIG. 11 is a view illustrating an NMR spectrum of Compound 1-f.

(5) Preparation of Compound 1

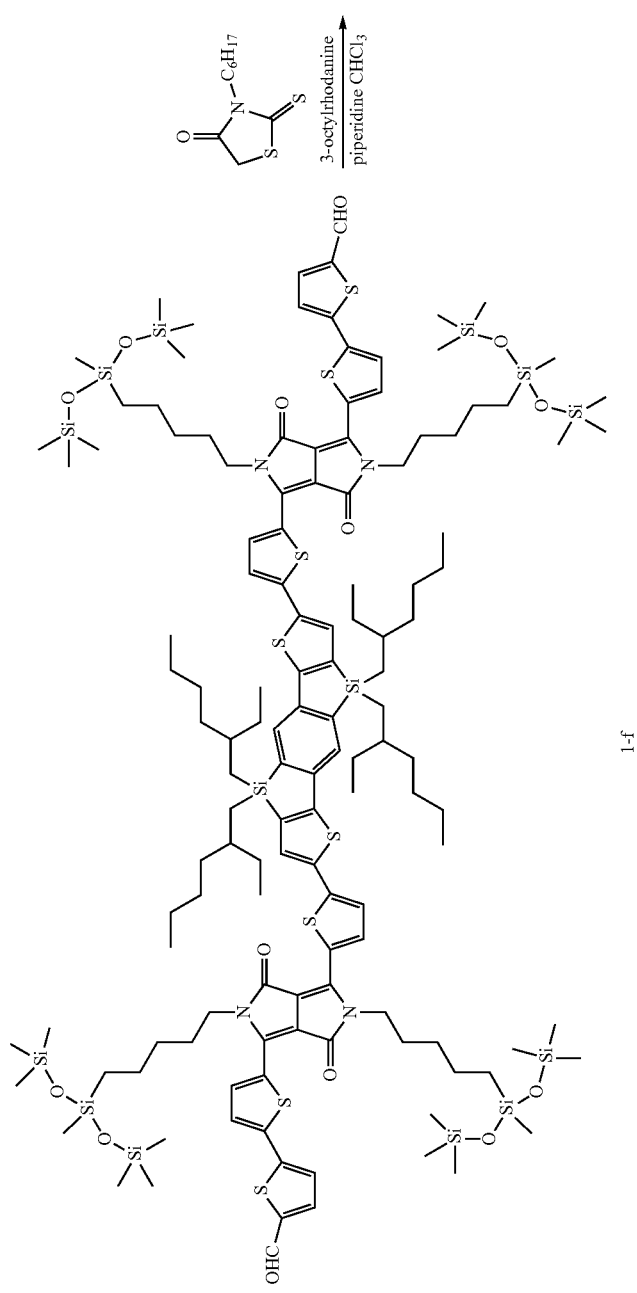

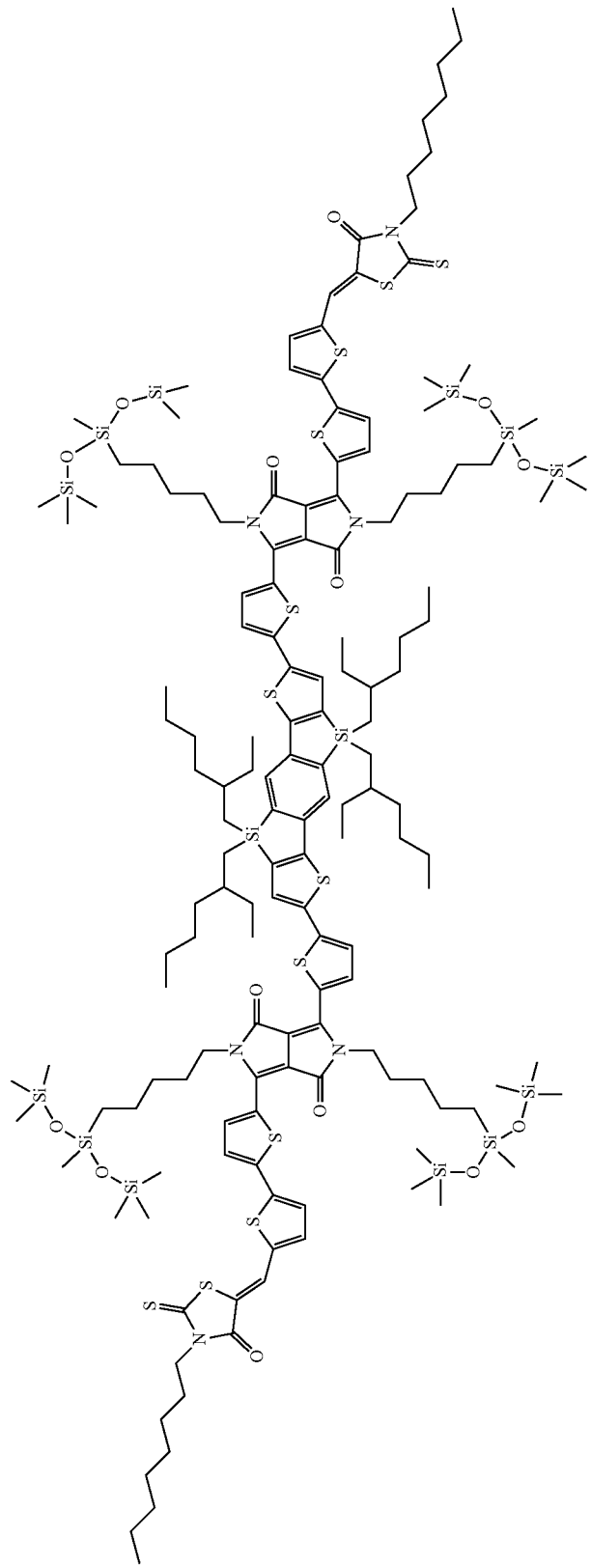

Compound 1-f (0.409 g, 0.15 mmol) and 3-octylrhodanine (0.3681 g, 1.5 mmol) were dissolved in 30 mL of chloroform ($CHCl_3$), three drops of piperidine were added thereto at room temperature, and the resulting mixture was refluxed for 24 hours. After reaction, an extraction was performed with dichloromethane, the remaining water was removed over magnesium sulfate ($MgSO_4$), and then the solvent was removed under reduced pressure. A dark brown solid was obtained by subjecting the remaining product to silica column (eluent: dichloromethane ($CH_2Cl_2$) and chloroform ($CHCl_3$)). The obtained solid was recrystallized two or three times with $CHCl_3$ and hexane to obtain Compound 1. (Yield: 67%)

FIG. 12 is a view illustrating an MS spectrum of Compound 1.

FIG. 13 is a view illustrating an NMR spectrum of Compound 1.

Preparation Example 2. Preparation of Compound 2

(1) Preparation of Compound 2-b stirred at room temperature for 12 hours. After reaction, a reactant was added to 100 mL of water, an extraction was performed with dichloromethane, the remaining water was removed over magnesium sulfate ($MgSO_4$), and then the solvent was removed under reduced pressure. The remaining product was purified with silica column (eluent: hexane) to obtain Compound 2-b. (Yield: 94%)

FIG. 14 is a view illustrating an NMR spectrum of Compound 2-b.

(2) Preparation of Compound 2-c

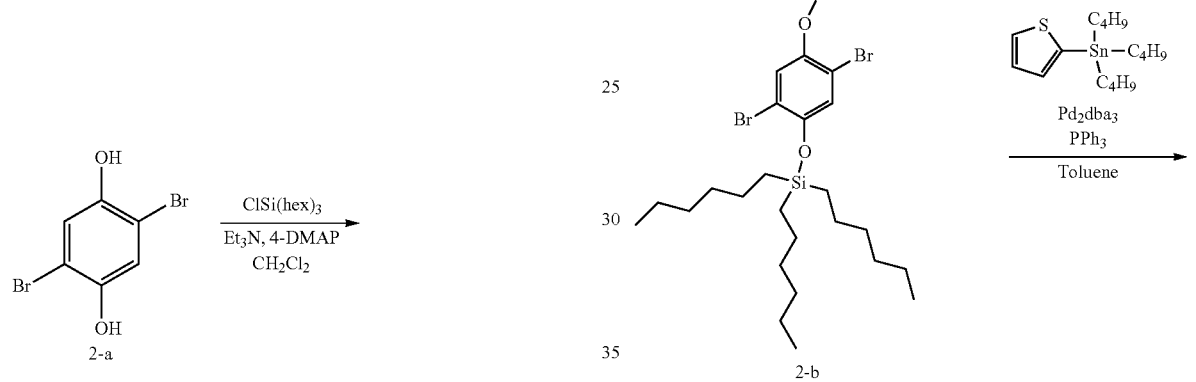

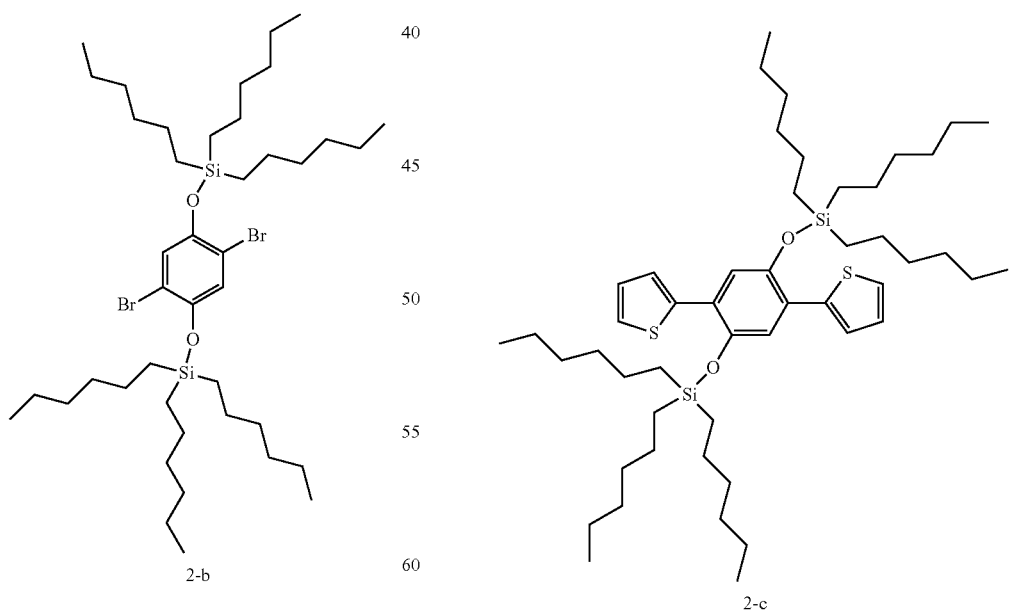

2-a and 4-dimethylaminopyridine (4-DMAP) (0.36 g, 2.92 mmol) were dissolved in 30 mL of dichloromethane, and then triethylamine ($Et_3N$) (3 mL, 21.51 mmol) and trihexylchlorosilane ($ClSi(hex)_3$) (7.46 mL, 20.37 mmol) were added thereto at 0° C., and the resulting mixture was Compound 2-b (5 g, 6 mmol) and tributyltin-thiophene (9.33 g, 25 mmol) were dissolved in 70 mL of toluene, a tris(dibenzylideneacetone)dipalladium(0) ($Pd_2dba_3$) catalyst (0.458 g, 0.05 mmol) and a triphenylphosphine ($PPh_3$)

ligand (0.52 g, 2 mmol) were added thereto, and the resulting mixture was stirred at 110° C. for 48 hours. After reaction, an extraction was performed with dichloromethane, the remaining water was removed over magnesium sulfate (MgSO$_4$), and then the solvent was removed under reduced pressure. Compound 2-c was obtained by subjecting the remaining product to silica column (eluent: hexane). (Yield: 59%)

FIG. 15 is a view illustrating an MS spectrum of Compound 2-c.

FIG. 16 is a view illustrating an NMR spectrum of Compound 2-c.

(3) Preparation of Compound 2-d

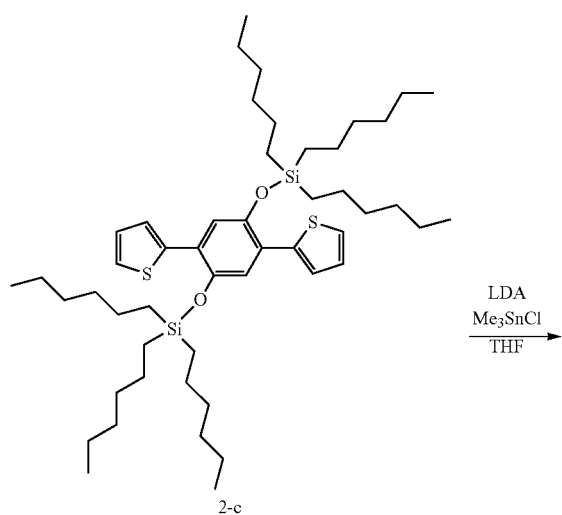

2-c

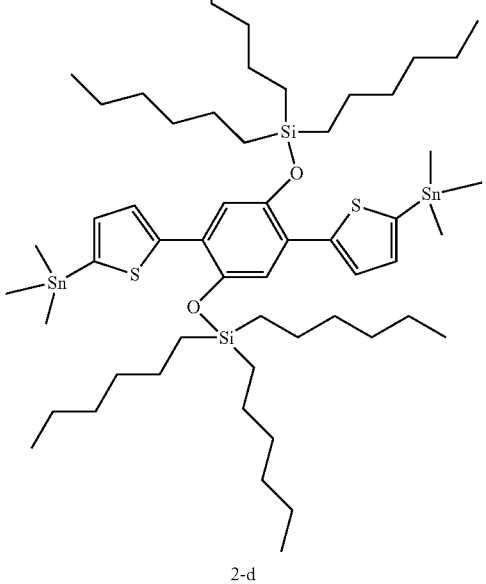

2-d

After Compound 2-c (3 g, 3.55 mmol) was dissolved in 100 mL of tetrahydrofuran (THF), 2 M lithium diisopropylamide (LDA) (5.325 mL, 10.65 mmol) was slowly injected thereinto at −78° C., and then the resulting mixture was stirred at −78° C. for 2 hours. Trimethyltin chloride (Me$_3$SnCl) (11 mL, 11 mmol) was added thereto at the same temperature, and the resulting mixture was slowly warmed to room temperature, and then reacted at room temperature for 3 hours. After reaction, an extraction was performed with dichloromethane, the remaining water was removed over magnesium sulfate (MgSO$_4$), and then the solvent was removed under reduced pressure to obtain Compound 2-d. (Yield: 83.4%)

FIG. 17 is a view illustrating an MS spectrum of Compound 2-d.

FIG. 18 is a view illustrating an NMR spectrum of Compound 2-d.

(4) Preparation of Compound 2-f

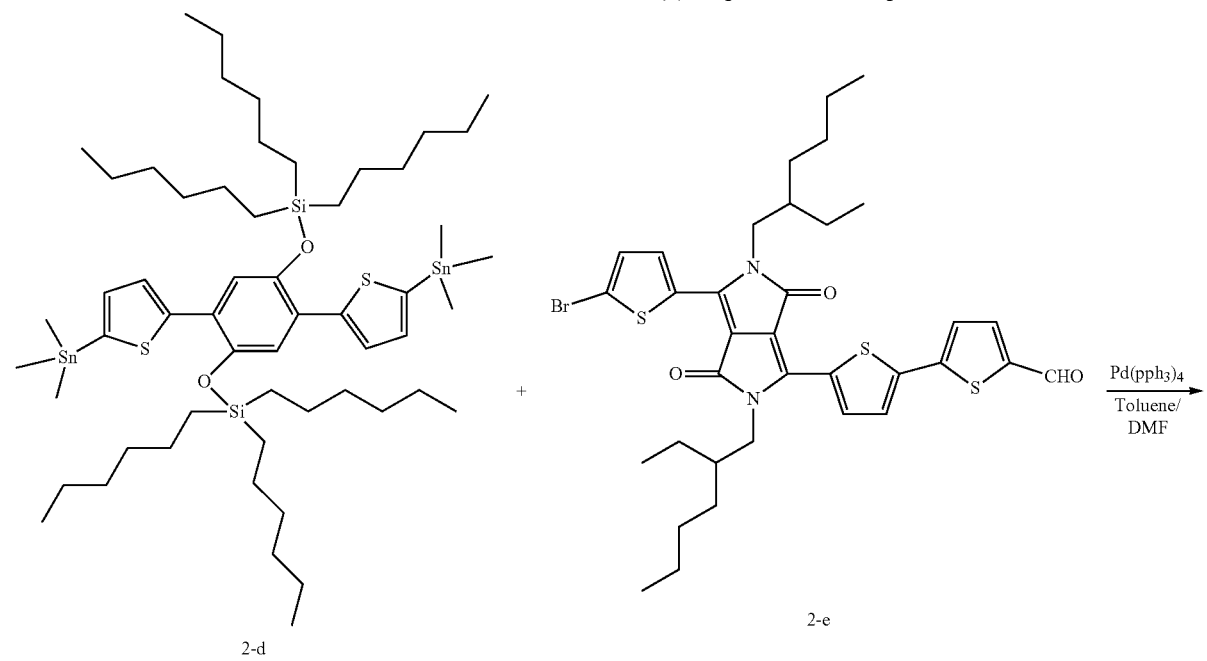

-continued

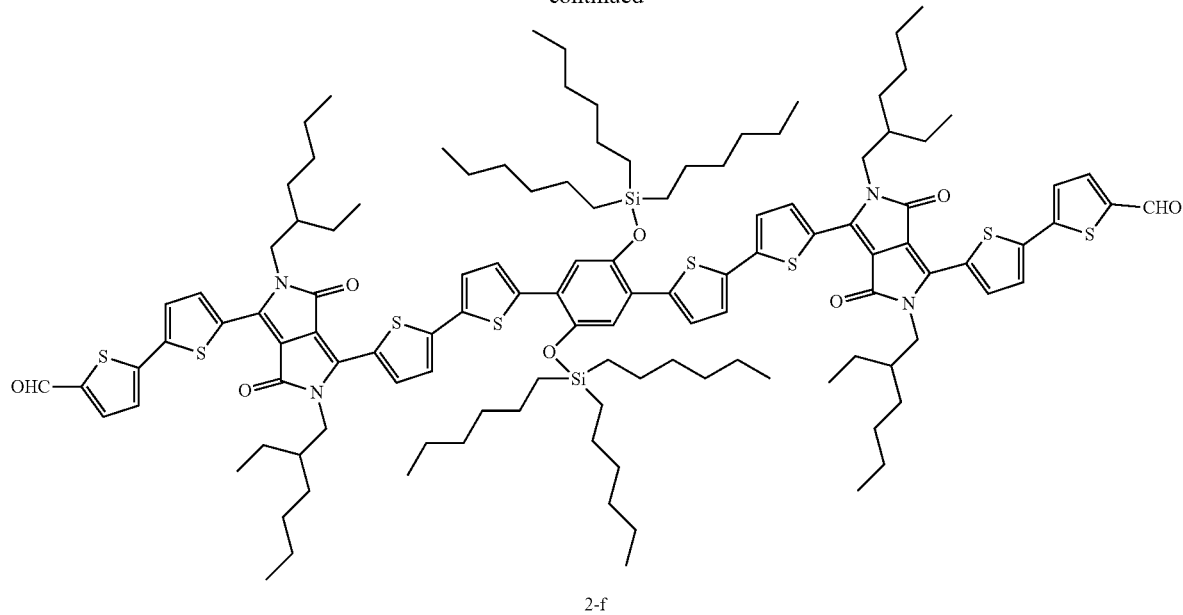

2-f

Compound 2-d (0.93 g, 0.80 mmol) and Compound 2-e (1.48 g, 2.08 mmol) were dissolved in 30 mL of toluene and 10 mL of dimethylformamide (DMF), a tris(dibenzylideneacetone)dipalladium(0) ($Pd_2dba_3$) catalyst (0.029 g, 0.025 mmol) and was added thereto, and the resulting mixture was stirred at 110° C. for 48 hours. After reaction, an extraction was performed with dichloromethane, the remaining water was removed over magnesium sulfate ($MgSO_4$), and then the solvent was removed under reduced pressure. Compound 2-f was obtained by subjecting the remaining product to silica column (eluent: dichloromethane ($CH_2Cl_2$) and chloroform ($CHCl_3$)). (Yield: 59%)

FIG. 19 is a view illustrating an MS spectrum of Compound 2-f.

FIG. 20 is a view illustrating an NMR spectrum of Compound 2-f.

(5) Preparation of Compound 2

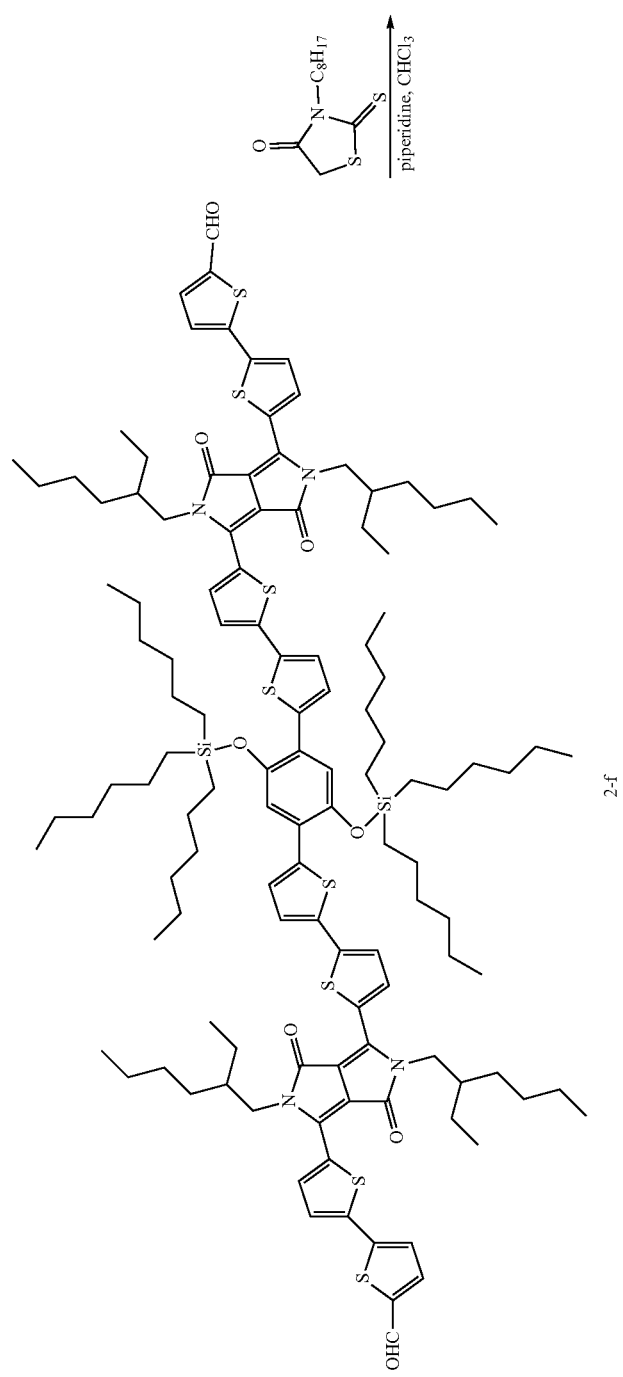

-continued
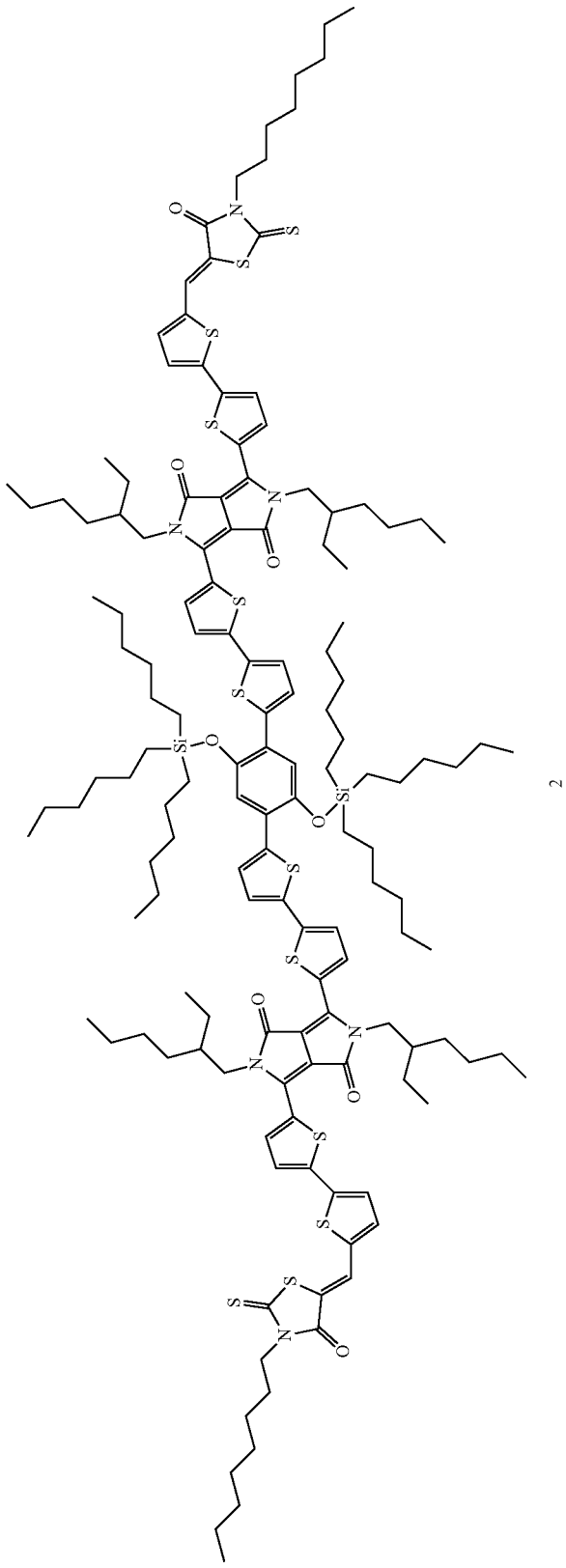

Compound 2-f (0.42 g, 0.2 mmol) and 3-octylrhodanine (0.368 g, 1.5 mmol) were dissolved in 30 mL of chloroform (CHCl₃), three drops of piperidine were added thereto at room temperature, and the resulting mixture was refluxed for 24 hours. After reaction, an extraction was performed with dichloromethane, the remaining water was removed over magnesium sulfate (MgSO₄), and then the solvent was removed under reduced pressure. Compound 2 was obtained by subjecting the remaining product to silica column (eluent: dichloromethane (CH₂Cl₂) and chloroform (CHCl₃)). (Yield: 61%)

FIG. 21 is a view illustrating an MS spectrum of Compound 2.

FIG. 22 is a view illustrating an NMR spectrum of Compound 2.

Preparation Example 3. Preparation of Compound 5

(1) Preparation of Compound 5-a

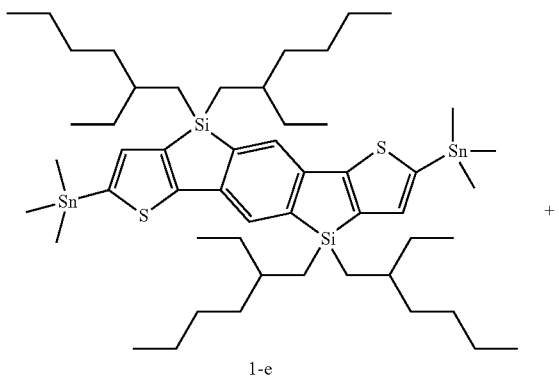

1-e

+

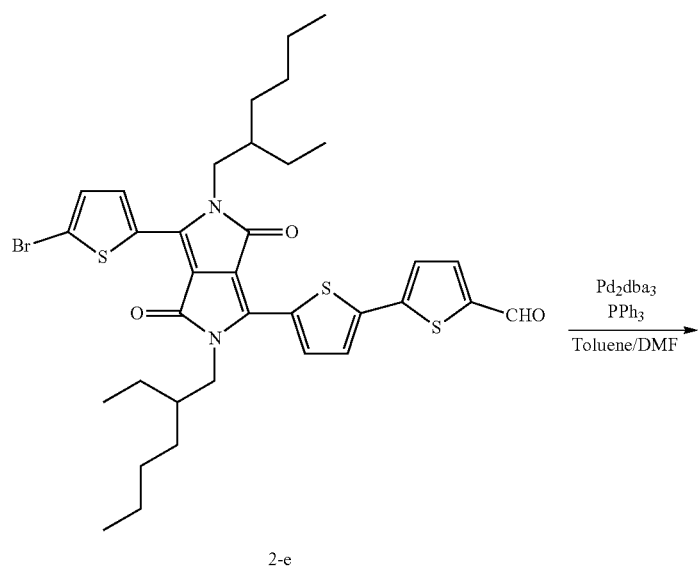

2-e

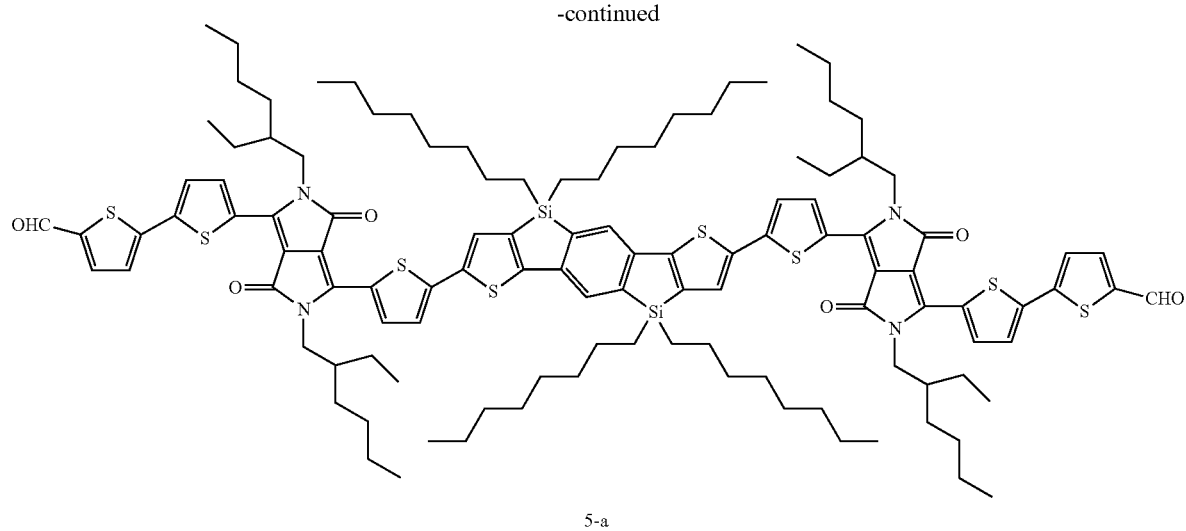

5-a

Compound 1-e (0.86 g, 0.8 mmol) and Compound 2-e (1.34 g, 1.88 mmol) were dissolved in 60 mL of toluene and 6 mL of dimethylformamide (DMF), a tris(dibenzylideneacetone)dipalladium(0) (Pd₂dba₃) catalyst (0.0504 g, 0.055 mmol) and a triphenylphosphine (PPh₃) ligand (0.0577 g, 0.22 mmol) were added thereto, and the resulting mixture was stirred at 110° C. for 48 hours. After reaction, an extraction was performed with dichloromethane, the remaining water was removed over magnesium sulfate (MgSO₄), and then the solvent was removed under reduced pressure. Compound 5-a was obtained by subjecting the remaining product to silica column (eluent: dichloromethane (CH₂Cl₂) and chloroform (CHCl₃)). (Yield: 58%)

FIG. 23 is a view illustrating an MS spectrum of Compound 5-a.

FIG. 24 is a view illustrating an NMR spectrum of Compound 5-a.

(2) Preparation of Compound 5

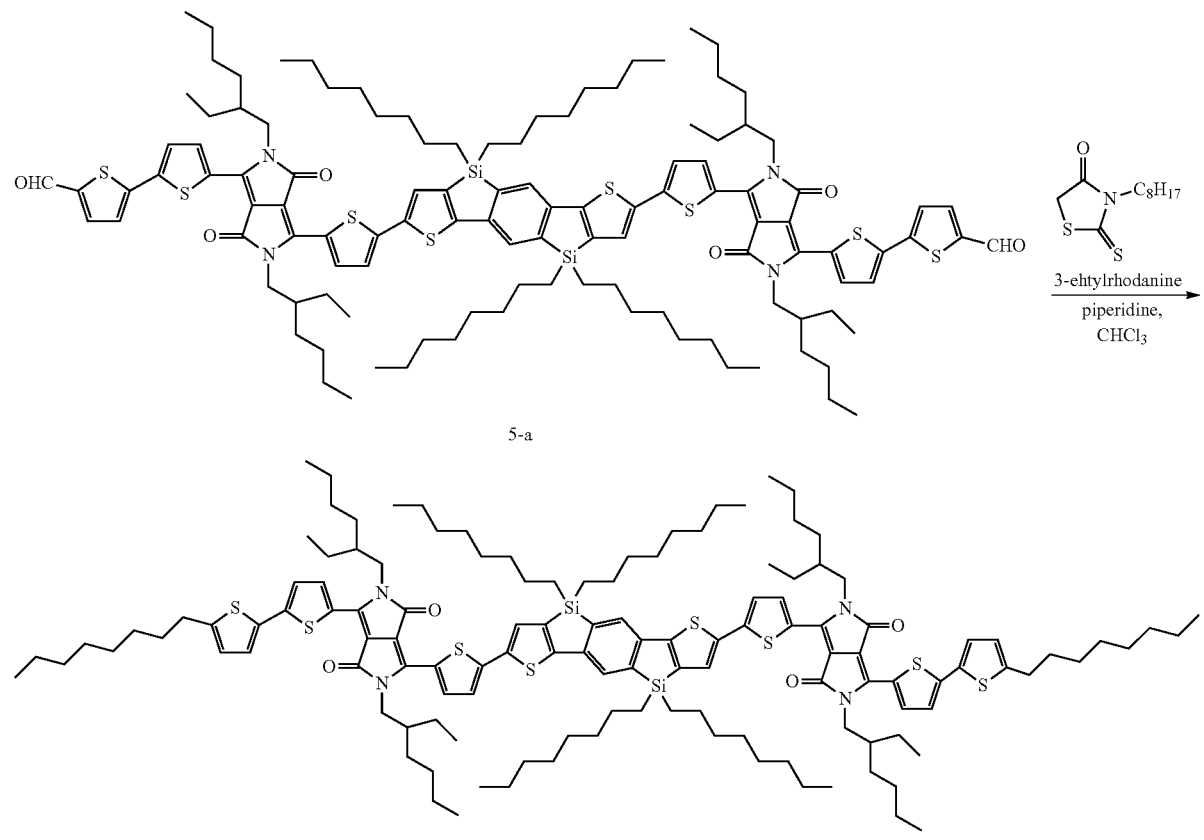

Compound 5-a (0.402 g, 0.20 mmol) and 3-octylrhodanine (0.491 g, 2.0 mmol) were dissolved in 20 mL of chloroform ($CHCl_3$), three drops of piperidine were added thereto at room temperature, and the resulting mixture was refluxed for 24 hours. After reaction, an extraction was performed with dichloromethane, the remaining water was removed over magnesium sulfate ($MgSO_4$), and then the solvent was removed under reduced pressure. A dark brown solid was obtained by subjecting the remaining product to silica column (eluent: dichloromethane ($CH_2Cl_2$) and chloroform ($CHCl_3$)). The obtained solid was recrystallized two or three times with chloroform ($CHCl_3$) and hexane to obtain Compound 5. (Yield: 66%)

FIG. 25 is a view illustrating an MS spectrum of Compound 5.

FIG. 26 is a view illustrating an NMR spectrum of Compound 5.

FIG. 27(a) is a view illustrating absorbance of Compound 1.

In FIG. 27(a), Compound 1(a), Compound 1(b), and Compound 1(c) mean Compound 1 in a solution state, Compound 1 formed as a thin film, and Compound 1 formed as a thin film and then heat-treated at 110° C., respectively.

FIG. 27(b) is a view illustrating absorbance of Compound 2.

In FIG. 27(b), Compound 2(a), Compound 2(b), and Compound 2(c) mean Compound 2 in a solution state, Compound 2 formed as a thin film, and Compound 2 formed as a thin film and then heat-treated at 110° C., respectively.

FIG. 27(c) is a view illustrating absorbance of Compound 5.

In FIG. 27(c), Compound 5(a), Compound 5(b), and Compound 5(c) mean Compound 5 in a solution state, Compound 5 formed as a thin film, and Compound 5 formed as a thin film and then heat-treated at 110° C., respectively.

In FIGS. 27(a) and 27(v), it can be confirmed that $\lambda_{max}$ of Compound 1(a) in a solution state and $\lambda_{max}$ of Compound 5(a) in a solution state are 710 nm, which are the same as each other, whereas $\lambda_{max}$ of Compound 1(b) in a thin film state is 775 nm, $\lambda_{max}$ of Compound 5(b) in a thin film state is 765 nm, and Compound 1(b) is more red-shifted than Compound 5(b). Through the confirmation, it can be seen that even though Compound 1 has a bulky side-chain, Compound 1 shows improved characteristics in terms of film packing.

Even in FIGS. 27(b) and 27(c), it can be seen that even though Compound 2 has a bulkier side-chain than Compound 5, Compound 2 shows improved characteristics in terms of film packing. Further, considering that a vibronic peak of Compound 2(c) is significantly increased after the film is heat-treated at 110° C., it can be seen that Compound 2 has excellent crystallinity.

FIGS. 28(a), 28(b), and 28(c) are views illustrating measurement results of CV of Compound 1, Compound 2, and Compound 5, respectively. Through the measurement results, the HOMO and LUMO energy levels of the respective compounds can be known.

FIGS. 29(a), 29(b), and 29(c) are views illustrating measurement results of DSC of Compound 1, Compound 2, and Compound 5, respectively. Through the measurement results, it can be seen that Compound 1, Compound 2, and Compound 5 have different $T_m$ and $T_c$.

FIG. 30(a) is a view illustrating an optical image of Compound 1 after being heat-treated at 100° C.

FIG. 30(b) is a view illustrating an optical image of Compound 2 after being heat-treated at 100° C.

FIG. 30(c) is a view illustrating an optical image of Compound 5 after being heat-treated at 100° C.

FIG. 30(d) is a view illustrating crystal size distributions of Compound 1, Compound 2, and Compound 5.

Through FIG. 30(d), it can be confirmed that Compound 5 has small crystals, whereas Compounds 1 and 2 have large crystals.

FIG. 31(a) is a view illustrating measurement results of XRD of Compound 1, Compound 2, and Compound 5 immediately after being prepared.

FIG. 31(b) is a view illustrating a measurement result of XRD of Compound 1 according to a heat treatment condition.

In FIG. 31(b), Compound 1(a) illustrates Compound 1 immediately after being prepared, Compound 1(b) illustrates Compound 1 after being heat-treated at 373 K, and Compound 1(c) illustrates Compound 1 after being heat-treated at 393 K.

FIG. 31(c) is a view illustrating a measurement result of XRD of Compound 2 according to a heat treatment condition.

In FIG. 31(c), Compound 2(a) illustrates Compound 2 immediately after being prepared, Compound 2(b) illustrates Compound 2 after being heat-treated at 373 K, and Compound 2(c) illustrates Compound 2 after being heat-treated at 393 K.

FIG. 31(d) is a view illustrating a measurement result of XRD of Compound 5 according to a heat treatment condition.

In FIG. 31(d), Compound 5(a) illustrates Compound 5 immediately after being prepared, Compound 5(b) illustrates Compound 5 after being heat-treated at 373 K, and Compound 5(c) illustrates Compound 5 after being heat-treated at 393 K.

Through FIG. 31(a), it can be confirmed that Compound 1 and Compound 2 show crystallinity even before the heat treatment, but Compound 5 does not show crystallinity before the heat treatment.

Through FIG. 31(b), it can be confirmed that Compound 1 shows crystallinity both before and after the heat treatment, and through FIG. 31(c), it can be confirmed that Compound 2 shows crystallinity even before the heat treatment, but has significantly improved crystallinity after the heat treatment.

Through FIG. 31(d), it can be confirmed that Compound 5 shows crystallinity after the heat treatment, but has insignificant crystallinity as compared to those of Compounds 1 and 2.

FIG. 32 illustrates measurement results of GIWAXS of Compound 2 and Compound 5 before and after the heat treatment.

In FIG. 32, As and TA mean before the heat treatment and after the heat treatment, respectively. It can be confirmed that both Compound 2 and Compound 5 have a change in a crystal direction after the heat treatment, but the case of Compound 2 has a more significantly changed crystal direction from a face-on direction to an edge-on direction than the case of Compound 5.

FIG. 33 is atomic force microscope (AFM) measurement results after Compounds 1, 2, and 5 are formed as a film.

FIG. 33(a) illustrates Compound 5 formed as a film, and FIG. 33(d) illustrates Compound 5 formed as a film and then heat-treated at 140° C.

FIG. 33(b) illustrates Compound 1 formed as a film, and FIG. 33(e) illustrates Compound 1 formed as a film and then heat-treated at 140° C.

FIG. 33(c) illustrates Compound 2 formed as a film, and FIG. 33(f) illustrates Compound 2 formed as a film and then heat-treated at 140° C.

Preparation Example 4. Preparation of Compound 6

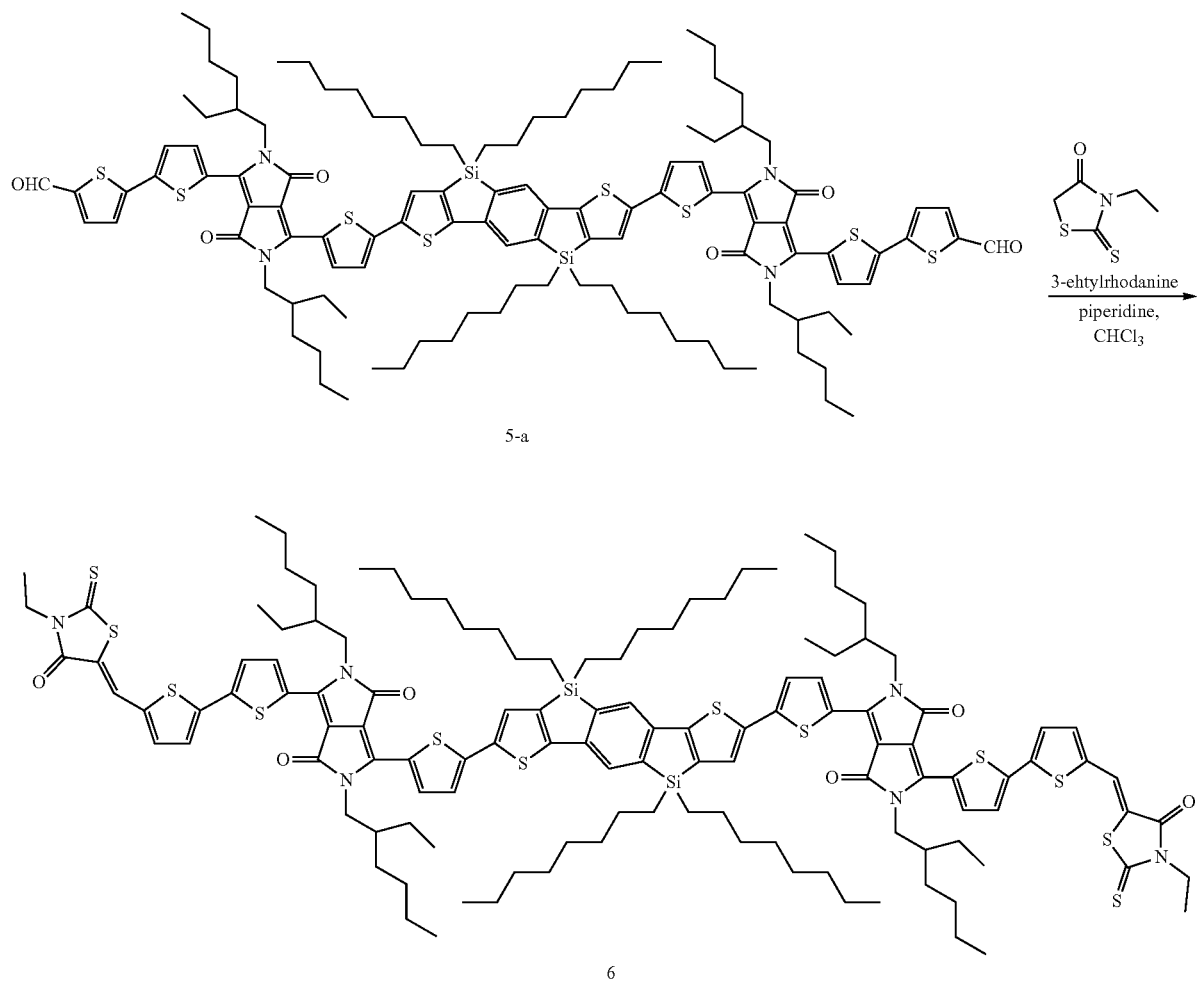

After Compound 5-a (0.52 g, 0.26 mmol) and 3-ethylrhodanine (0.48 g, 3 mmol) were dissolved in chloroform, three drops of piperidine were added thereto, and the resulting mixture was refluxed for 24 hours. Thereafter, the reactant was put into dichloromethane and washed with water, and then the solvent was removed. The obtained reactant was subjected to silica purification, recrystallized again with chloroform and methanol, and filtered to obtain 0.5 g of Compound 6. (Yield: 84%)

FIG. 34 is a view illustrating an NMR spectrum of Compound 6.

FIG. 35 is a view illustrating an MS spectrum of Compound 6.

Preparation Example 5. Preparation of Compound 7

(1) Preparation of Compound 7-b

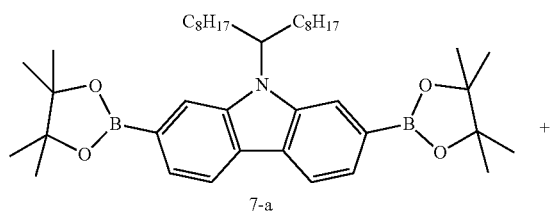

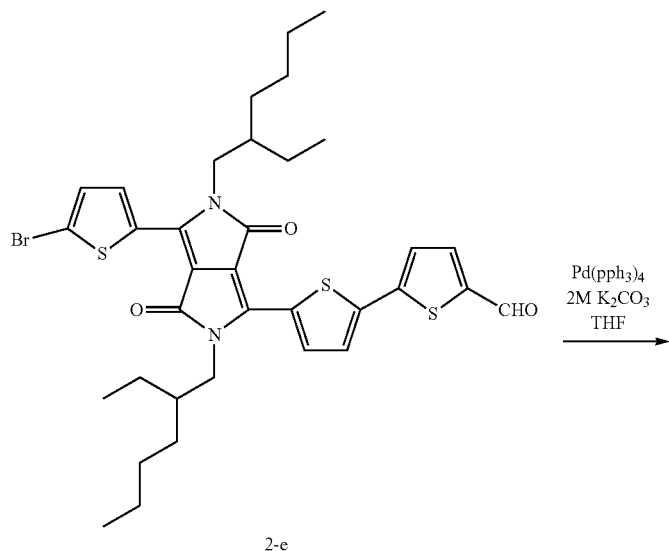

2-e

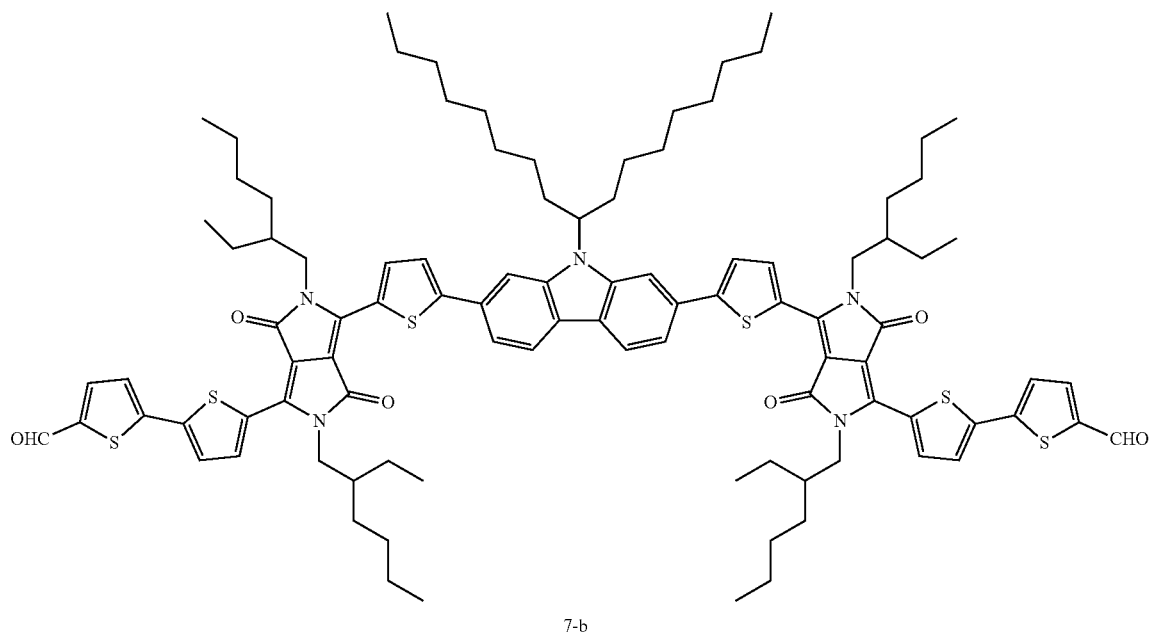

7-b

Compound 7-a (0.46 g, 0.7 mmol), Compound 2-e (1.07 g, 1.5 mmol), and tetrakis(triphenylphosphine)palladium(0) (Pd(PPh$_3$)$_4$) (58 mg, 0.05 mmol) were dissolved in 30 mL of tetrahydrofuran (THF) and 2 M potassium carbonate (K$_2$CO$_3$) (7.5 mL, 15 mmol), and the resulting solution was stirred at 70° C. for 48 hours. Thereafter, the reactant was precipitated in methanol, the precipitated reactant was filtered, and then subjected to silica purification. The obtained compound was recrystallized again with chloroform and methanol and filtered to obtain 0.68 g of Compound 7-b. (Yield: 59%)

FIG. 36 is a view illustrating an NMR spectrum of Compound 7-b.

FIG. 37 is a view illustrating an MS spectrum of Compound 7-b.

(2) Preparation of Compound 7

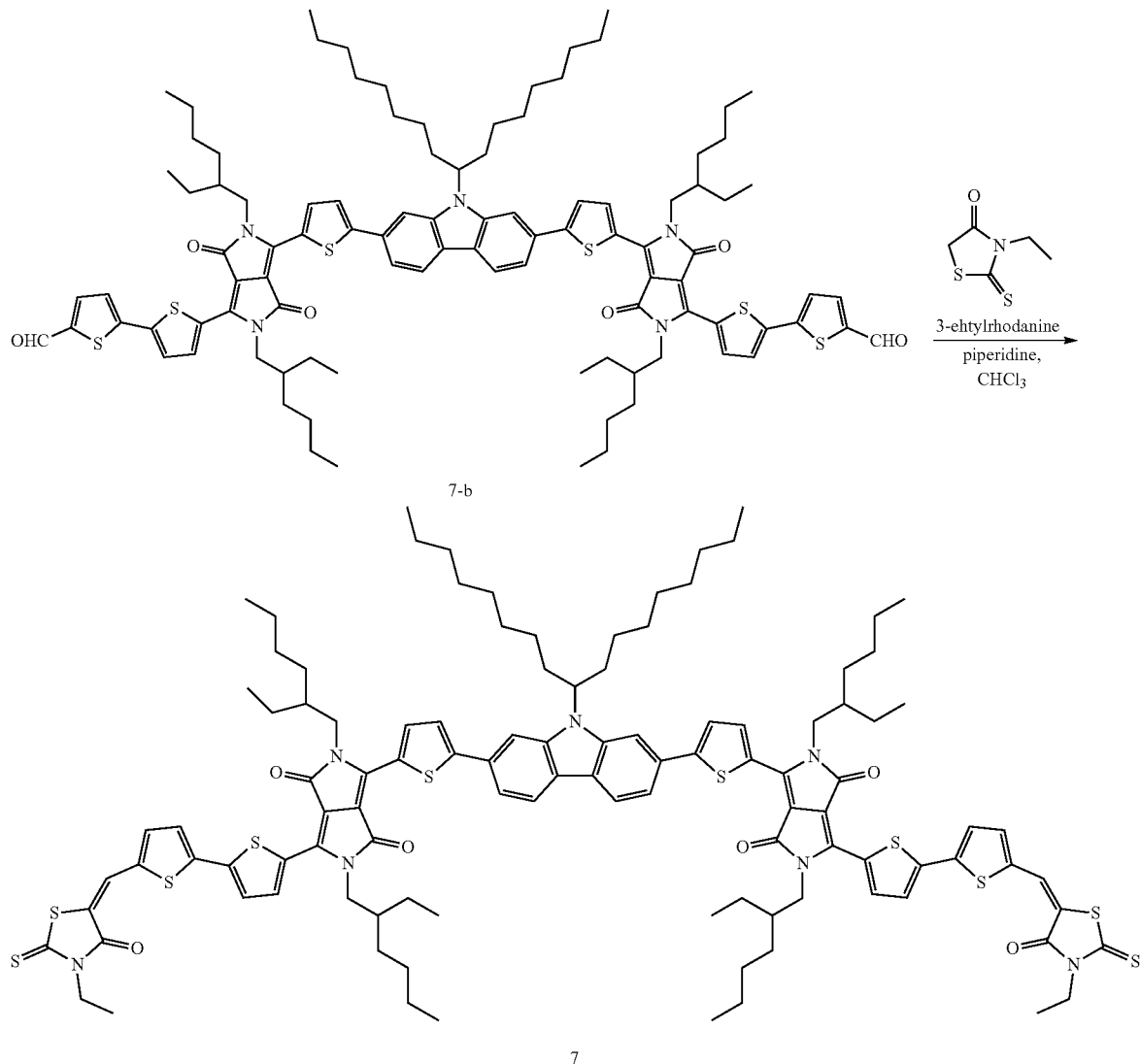

After Compound 7-b (0.40 g, 0.24 mmol) and 3-ethylrhodanine (0.74 g, 4.6 mmol) were dissolved in chloroform, three drops of piperidine were added thereto, and the resulting mixture was refluxed for 24 hours. Thereafter, the reactant was put into dichloromethane and washed with water, and then the solvent was removed. The obtained reactant was subjected to silica purification, recrystallized again with chloroform and methanol, and filtered to obtain 0.41 g of Compound 7. (Yield: 87%)

FIG. 38 is a view illustrating an NMR spectrum of Compound 7.

FIG. 39 is a view illustrating an MS spectrum of Compound 7.

Example 1

Source and drain electrodes of gold/nickel (Au/Ni) (13/3 nm) were formed on a washed glass substrate by using photolithography. The substrate on which the source and drain electrodes were formed was washed with acetone, distilled water, and isopropyl alcohol, and then dried at 110° C. for 1 hour. The dried substrate was treated with UV/ozone for 30 minutes, and then put into a glove box. A solution in which Compound 1 was dissolved at a concentration of 3 mg/mL in chlorobenzene was spin-coated at 1,500 rpm on the substrate put into the glove box, and the substrate was heat-treated at 100° C. Thereafter, CYTOP was spin-coated at 2,000 rpm thereon, and the substrate was heat-treated at 90° C. for 1 hour to form an insulating layer. Aluminum (Al) was thermally deposited (thermal evaporation) to have a thickness of 50 nm on the insulating layer, thereby forming a gate electrode.

Example 2

An organic transistor was manufactured in the same manner as in Example 1, except that in the manufacturing method in Example 1, the solution including Compound 1 was spin-coated on the substrate, and then the substrate was heat-treated at 120° C.

Example 3

An organic transistor was manufactured in the same manner as in Example 1, except that in the manufacturing method in Example 1, the solution including Compound 1 was spin-coated on the substrate, and then the substrate was heat-treated at 140° C.

Example 4

An organic transistor was manufactured in the same manner as in Example 1, except that in the manufacturing method in Example 1, Compound 2 was used instead of Compound 1.

Example 5

An organic transistor was manufactured in the same manner as in Example 2, except that in the manufacturing method in Example 2, Compound 2 was used instead of Compound 1.

Example 6

An organic transistor was manufactured in the same manner as in Example 3, except that in the manufacturing method in Example 3, Compound 2 was used instead of Compound 1.

Comparative Example 1

An organic transistor was manufactured in the same manner as in Example 1, except that in the manufacturing method in Example 1, Compound 5 was used instead of Compound 1.

Comparative Example 2

An organic transistor was manufactured in the same manner as in Comparative Example 1, except that in the manufacturing method in Comparative Example 1, the solution including Compound 5 was heat-treated at 120° C.

Comparative Example 3

An organic transistor was manufactured in the same manner as in Comparative Example 1, except that in the manufacturing method in Comparative Example 1, the solution including Compound 5 was heat-treated at 140° C.

Table 1 and FIG. 40 show the evaluation of characteristics of the organic transistors according to an exemplary embodiment of the present specification.

TABLE 1

| | Compound | Heat treatment temperature (° C.) | Average charge mobility ($cm^2/Vs$) | Highest charge mobility ($cm^2/Vs$) | Subthreshold swing (V/Dec) | Threshold voltage (V) | on/off ($10^6$) |
|---|---|---|---|---|---|---|---|
| Example 1 | Compound 1 | 100 | 1.06 ± 0.57 | 2.38 | 0.31 ± 0.07 | −8.13 ± 1.49 | 1.00 ± 0.61 |
| Example 2 | Compound 1 | 120 | 0.85 ± 0.26 | 2.18 | 0.29 ± 0.13 | −4.62 ± 1.56 | 0.24 ± 0.17 |
| Example 3 | Compound 1 | 140 | 0.67 ± 0.28 | 1.67 | 0.36 ± 0.13 | −8.08 ± 2.62 | 0.43 ± 0.30 |
| Example 4 | Compound 2 | 100 | 1.00 ± 0.41 | 2.02 | 1.85 ± 1.40 | −8.56 ± 0.56 | 0.25 ± 0.13 |
| Example 5 | Compound 2 | 120 | 0.92 ± 0.29 | 2.51 | 0.32 ± 0.12 | −7.36 ± 0.58 | 0.12 ± 0.10 |
| Example 6 | Compound 2 | 140 | 1.09 ± 0.32 | 3.16 | 0.30 ± 0.08 | −14.49 ± 3.13 | 1.65 ± 1.45 |
| Comparative Example 1 | Compound 5 | 100 | 0.41 ± 0.02 | 0.47 | 0.36 ± 0.07 | −10.13 ± 0.88 | 1.38 ± 0.90 |
| Comparative Example 2 | Compound 5 | 120 | — | — | — | — | — |
| Comparative Example 3 | Compound 5 | 140 | — | — | — | — | — |

FIG. 40(a) and FIG. 40(d) are views illustrating characteristics of an organic transistor according to Example 1 of the present specification.

FIG. 40(b) and FIG. 40(e) are views illustrating characteristics of an organic transistor according to Example 4 of the present specification.

FIG. 40(c) and FIG. 40(f) are views illustrating characteristics of an organic transistor according to Comparative Example 1 of the present specification.

From the results of Table 1 and FIG. 40, it can be confirmed that the organic transistors of Examples 1 to 6 in which the compounds (Compounds 1 and 2) including a substituted or unsubstituted silyl group or a substituted or unsubstituted siloxane group in the side-chain thereof were applied to the organic semiconductor layer of the organic transistor had more improved performances, such as an average charge mobility, a highest charge mobility, and an on/off ratio, than those of Comparative Examples 1 to 3 in which a compound (Compound 5), which did not include a substituted or unsubstituted silyl group or a substituted or unsubstituted siloxane group in the side-chain thereof, was applied to the organic semiconductor layer of the organic transistor.

Example 7

Source and drain electrodes of gold/nickel (Au/Ni) (13/3 nm) were formed on a washed glass substrate by using photolithography. The substrate on which the source and drain electrodes were formed was washed with acetone, distilled water, and isopropyl alcohol, and then dried at 110° C. for 1 hour. The dried substrate was treated with UV/ozone for 30 minutes, and then put into a glove box. A solution in which Compound 1 was dissolved at a concentration of 3 mg/mL in 2-methyltetrahydrofuran was spin-coated at 1,500 rpm on the substrate put into the glove box, and the substrate was heat-treated at 100° C. Thereafter, CYTOP was spin-coated at 2,000 rpm thereon, and the substrate was heat-treated at 90° C. for 1 hour to form an insulating layer. Aluminum (Al) was thermally deposited (thermal evaporation) to have a thickness of 50 nm on the insulating layer, thereby forming a gate electrode.

Example 8

Source and drain electrodes of gold/nickel (Au/Ni) (13/3 nm) were formed on a washed glass substrate by using photolithography. The substrate on which the source and drain electrodes were formed was washed with acetone, distilled water, and isopropyl alcohol, and then dried at 110° C. for 1 hour. The dried substrate was treated with UV/ozone for 30 minutes, and then put into a glove box. A solution in which Compound 2 was dissolved at a concentration of 3 mg/mL in 2-methyltetrahydrofuran was spin-coated at 1,500 rpm on the substrate put into the glove box, and the substrate was heat-treated at 140° C. Thereafter, CYTOP was spin-coated at 2,000 rpm thereon, and the substrate was heat-treated at 90° C. for 1 hour to form an insulating layer. Aluminum (Al) was thermally deposited (thermal evaporation) to have a thickness of 50 nm on the insulating layer, thereby forming a gate electrode.

Comparative Example 4

It was attempted to manufacture a device by using Compound 6, but the device could not be manufactured because Compound 6 was not dissolved in the solvent (2-methyltetrahydrofuran)).

Comparative Example 5

It was attempted to manufacture a device by using Compound 7, but the device could not be manufactured because Compound 7 was not dissolved in the solvent (2-methyltetrahydrofuran)).

Table 2 and FIG. 41 show the evaluation of characteristics of the organic transistors according to an exemplary embodiment of the present specification.

TABLE 2

| | Compound | Heat treatment temperature (° C.) | Average charge mobility (cm$^2$/Vs) | Highest charge mobility (cm$^2$/Vs) | Subthreshold swing (V/Dec) | Threshold voltage (V) | on/off (10$^6$) | Contact Resistance (MΩ) |
|---|---|---|---|---|---|---|---|---|
| Example 7 | Compound 1 | 100 | 1.53 ± 0.71 | 2.60 | 3.41 ± 1.27 | −5.11 ± 1.58 | 0.82 ± 0.49 | 0.41 ± 0.19 |
| Example 8 | Compound 2 | 140 | 2.64 ± 0.65 | 3.06 | 3.64 ± 0.17 | −4.66 ± 1.12 | 0.89 ± 0.73 | 0.15 ± 0.08 |

FIG. 41(*a*) is a view illustrating characteristics of an organic transistor according to Example 7 of the present specification.

FIG. 41(*b*) is a view illustrating characteristics of an organic transistor according to Example 8 of the present specification.

From the results of Table 2 and FIG. 41, it can be confirmed that compounds (Compounds 1 and 2) including a substituted or unsubstituted silyl group or a substituted or unsubstituted siloxane group in the side-chain thereof were dissolved well in an eco-friendly solvent (2-methyltetrahydrofuran), and the cases (Examples 7 and 8) where the compounds are applied to an organic semiconductor layer of an organic transistor showed performances similar to those of the cases (Examples 1 to 6) where the compounds were dissolved in a general solvent.

In contrast, from Comparative Examples 4 and 5, it can be confirmed that the compounds (Compounds 6 and 7), which did not include a substituted or unsubstituted silyl group or a substituted or unsubstituted siloxane group in the side-chain thereof, were not dissolved in an eco-friendly solvent.

Example 9

An aluminum gate electrode was deposited to have a thickness of 50 nm on a flexible polyethylene naphthalate (PEN) substrate, which was washed with distilled water (DI water), acetone, and isopropyl alcohol (IPA) in this order each for 10 minutes, through thermal deposition. Thereafter, polyimide dissolved at 80 mg/ml in cyclohexanone was spin-coated as an insulating layer, dried at 90° C. for 2 minutes, and then crosslinked under UV at a wavelength of 365 nm for 10 minutes, and then heat-treated at 90° C. for 10 minutes. Thereafter, Compound 1 dissolved in chlorobenzene was spin-coated on the insulating layer. Finally, Au was formed to have a thickness of 13 nm as a source electrode and a drain electrode by using thermal deposition, thereby manufacturing an organic transistor-based gas sensor.

FIG. 42 is a view illustrating a performance measurement result of the gas sensor manufactured in Example 9. FIG. 42 (*a*) is a graph when the drain voltage is −5 V and the gate voltage is −20 V, FIG. 42(*b*) is a graph when the drain voltage is −40 V and the gate voltage is −20 V, FIG. 42(*c*) is a graph when the drain voltage is −5 V and the gate voltage is −40 V, and FIG. 42(*d*) is a graph when the drain voltage is −40 V and the gate voltage is −40 V.

Example 10

A gas sensor was manufactured in the same manner as in Example 9, except that in Example 9, Compound 2 was used instead of Compound 1.

FIG. 43 is a view illustrating the performance measurement result of the gas sensor manufactured in Example 10. FIG. 43 (*a*) is a graph when the drain voltage is −5 V and the gate voltage is −20 V, FIG. 43(*b*) is a graph when the drain voltage is −40 V and the gate voltage is −20 V, FIG. 43(*c*) is a graph when the drain voltage is −5 V and the gate voltage is −40 V, and FIG. 43(*d*) is a graph when the drain voltage is −40 V and the gate voltage is −40 V.

What is claimed is:

1. An organic transistor comprising:
   an organic semiconductor layer including a compound of Chemical Formula 1-1 or 1-2:

[Chemical Formula 1-1]

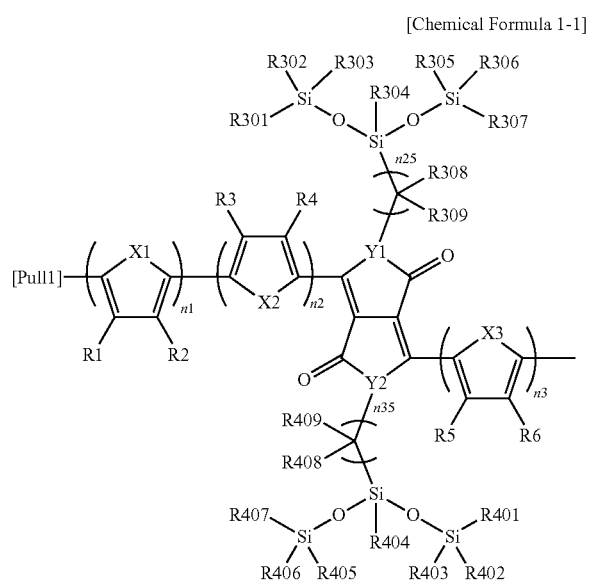

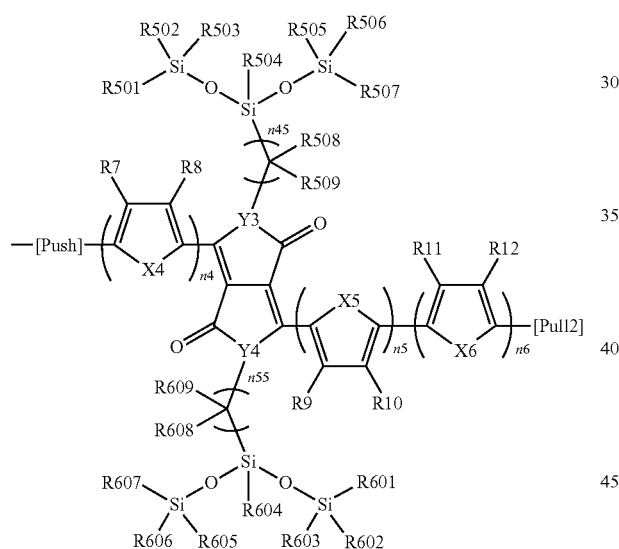

[Chemical Formula 1-2]

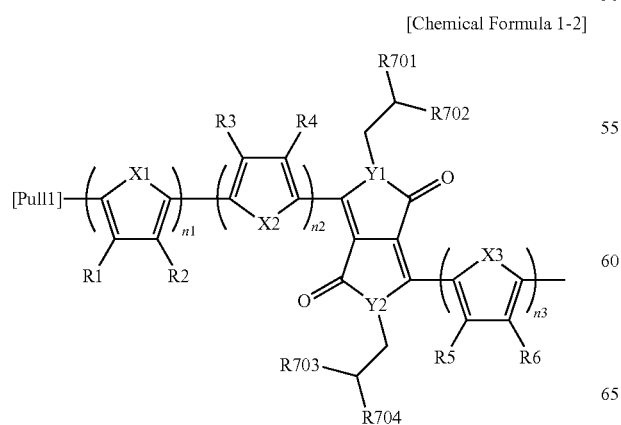

-continued

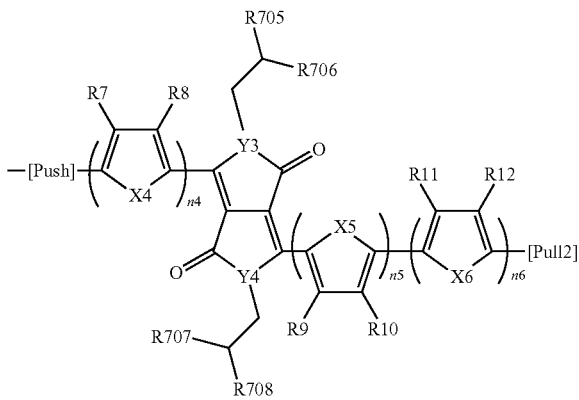

wherein:

n1 to n6 are each an integer from 1 to 3, when n1 is 2 or more, two or more

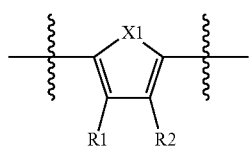

are the same as or different from each other, when n2 is 2 or more, two or more

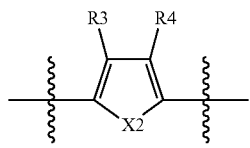

are the same as or different from each other, when n3 is 2 or more, two or more

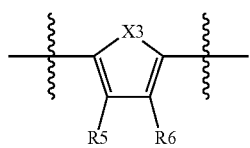

are the same as or different from each other, when n4 is 2 or more, two or more

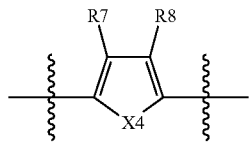

are the same as or different from each other, when n5 is 2 or more, two or more

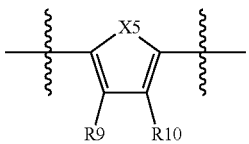

are the same as or different from each other, and
when n6 is 2 or more, two or more

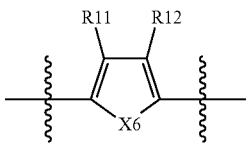

are the same as or different from each other;

X1 to X6 are the same as or different from each other, and are each independently CRR', NR, O, SiRR', PR, S, GeRR', Se, or Te;

Y1 to Y4 are the same as or different from each other, and are each independently CR", N, SiR", P, or GeR";

[Push] is any one of the following structures:

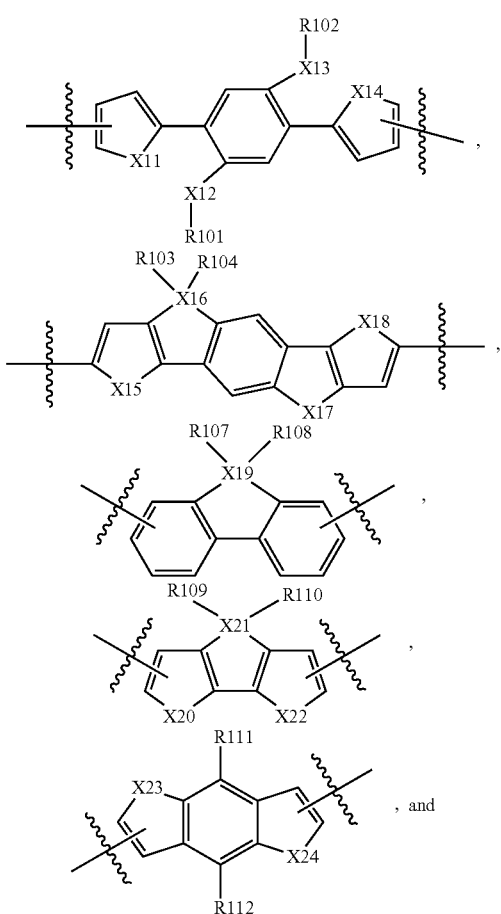

, and

-continued

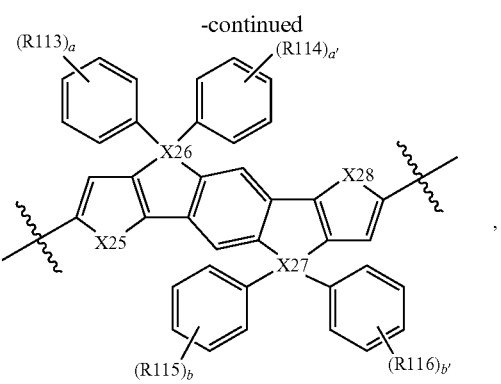

a, a', b, and b' are each an integer from 1 to 5,
when a is 2 or more, two or more R113 are the same as or different from each other,
when a' is 2 or more, two or more R114 are the same as or different from each other,
when b is 2 or more, two or more R115 are the same as or different from each other, and
when b' is 2 or more, two or more R116 are the same as or different from each other;

X11, X14, X15, X17, X20, X22, X23, X24, X25, and X28 are the same as or different from each other, and are each independently CRR', NR, O, SiRR', PR, S, GeRR', Se, or Te;

X12 and X13 are the same as or different from each other, and are each independently O, SiRR', or S;

X16, X19, X21, X26, and X27 are the same as or different from each other, and are each independently C, Si, or Ge;

X18 is S;

[Pull1] and [Pull2] are the same as or different from each other, and are each any one of the following structures:

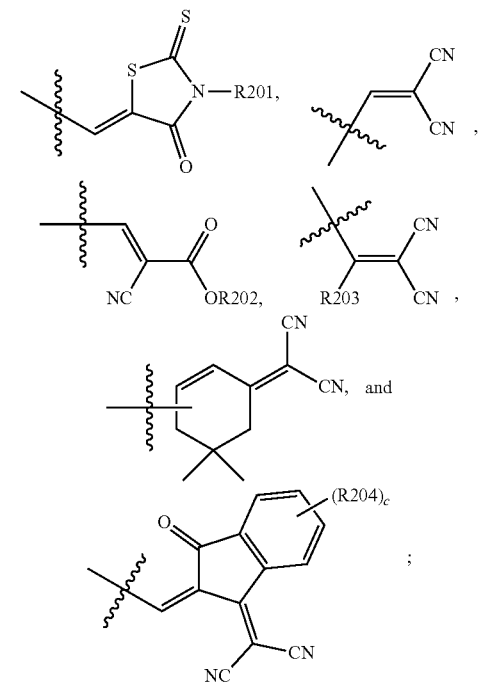

c is an integer from 1 to 4, and when c is 2 or more, two or more R204 are the same as or different from each other;

R, R', R", R1 to R12, R101 to R104, R107 to R116, and R201 to R204 are the same as or different from each other, and are each independently hydrogen, deuterium, a halogen group, a nitrile group, a nitro group, an imide group, an amide group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted siloxane group, a substituted or unsubstituted boron group, a substituted or unsubstituted amine group, a substituted or unsubstituted aryl group, or a substituted or unsubstituted heterocyclic group;

in the Chemical Formula 1-2, at least one of R101 to R104, R107 to R116 includes a substituted or unsubstituted silyl group or a substituted or unsubstituted siloxane group;

n25, n35, n45, and n55 are each an integer from 0 to 5, when n25 is 2 or more, two or more

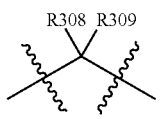

are the same as or different from each other, when n35 is 2 or more, two or more

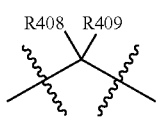

are the same as or different from each other, when n45 is 2 or more, two or more

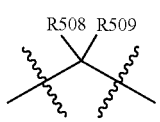

are the same as or different from each other, and when n55 is 2 or more, two or more

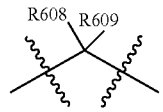

are the same as or different from each other; and

R301 to R309, R401 to R409, R501 to R509, R601 to R609, and R701 to R708 are the same as or different from each other, and are each independently hydrogen, deuterium, a halogen group, a nitrile group, a nitro group, an imide group, an amide group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted siloxane group, a substituted or unsubstituted boron group, a substituted or unsubstituted amine group, a substituted or unsubstituted aryl group, or a substituted or unsubstituted heterocyclic group.

2. The organic transistor of claim 1, wherein R1 to R12, R101 to R104, R107 to R116, and R201 to R204 are the same as or different from each other, and are each independently hydrogen, a halogen group, a substituted or unsubstituted alkyl group, a substituted or unsubstituted cycloalkyl group, a substituted or unsubstituted alkoxy group, a substituted or unsubstituted silyl group, a substituted or unsubstituted siloxane group, a substituted or unsubstituted amine group, a substituted or unsubstituted aryl group, or a substituted or unsubstituted heterocyclic group.

3. The organic transistor of claim 1, wherein R1 to R12, R101 to R104, R107 to R116, and R201 to R204 are the same as or different from each other, and are each independently hydrogen, a substituted or unsubstituted alkyl group, a substituted or unsubstituted silyl group, or a substituted or unsubstituted siloxane group.

4. The organic transistor of claim 1, wherein X1 to X6 are the same as or different from each other, and are each independently O, SiRR', or S.

5. The organic transistor of claim 1, wherein Y1 to Y4 are the same as or different from each other, and are each independently CR", N, or SiR".

6. The organic transistor of claim 1, wherein X11, X14, X15, X17, X20, X22, X23, X24, X25, and X28 are the same as or different from each other, and are each independently O, SiRR", or S.

7. An organic transistor comprising:

an organic semiconductor layer including any one of Chemical Formulae 1-3 to 1-8:

[Chemical Formula 1-3]
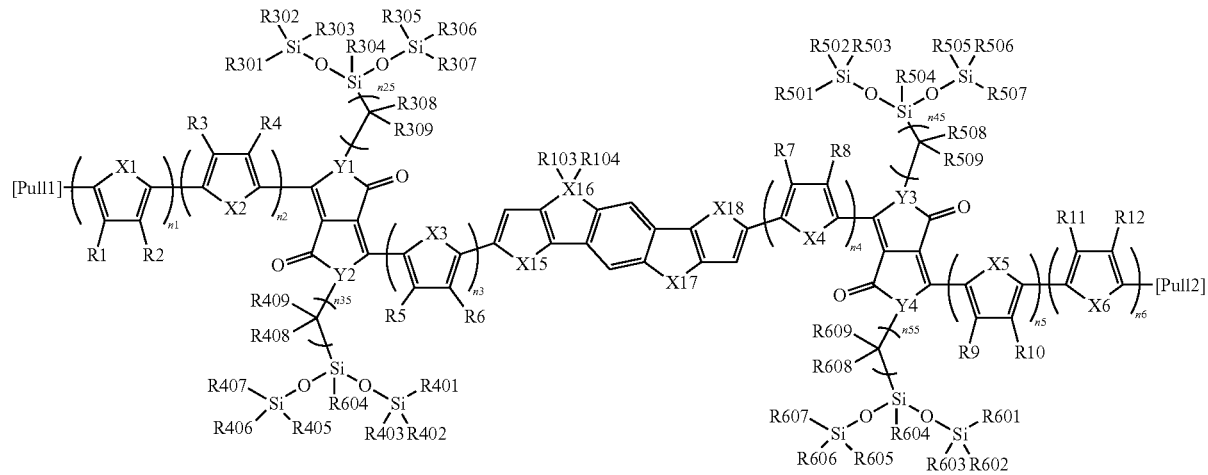
[Chemical Formula 1-4]
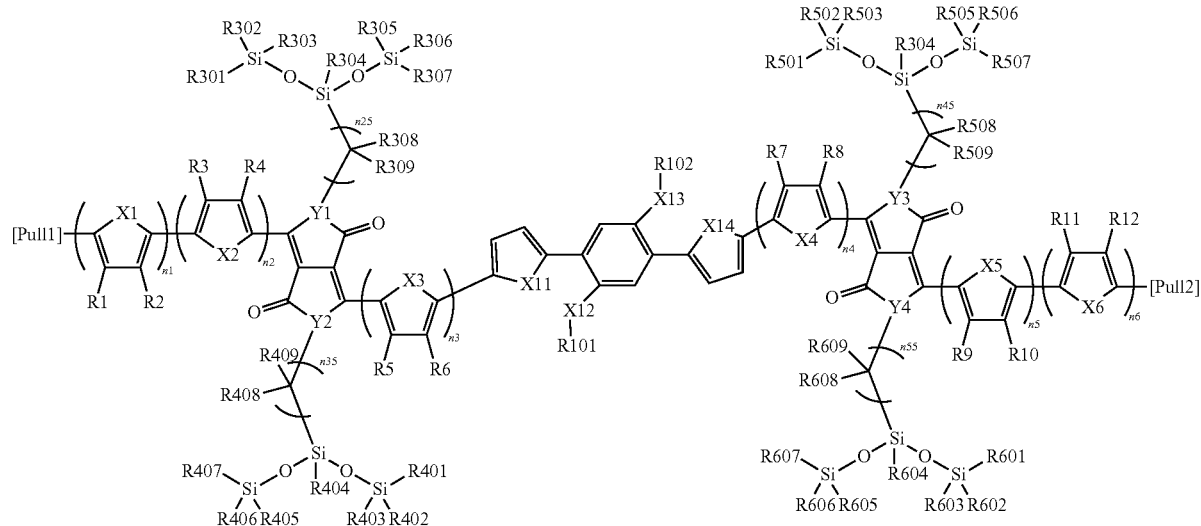
[Chemical Formula 1-5]
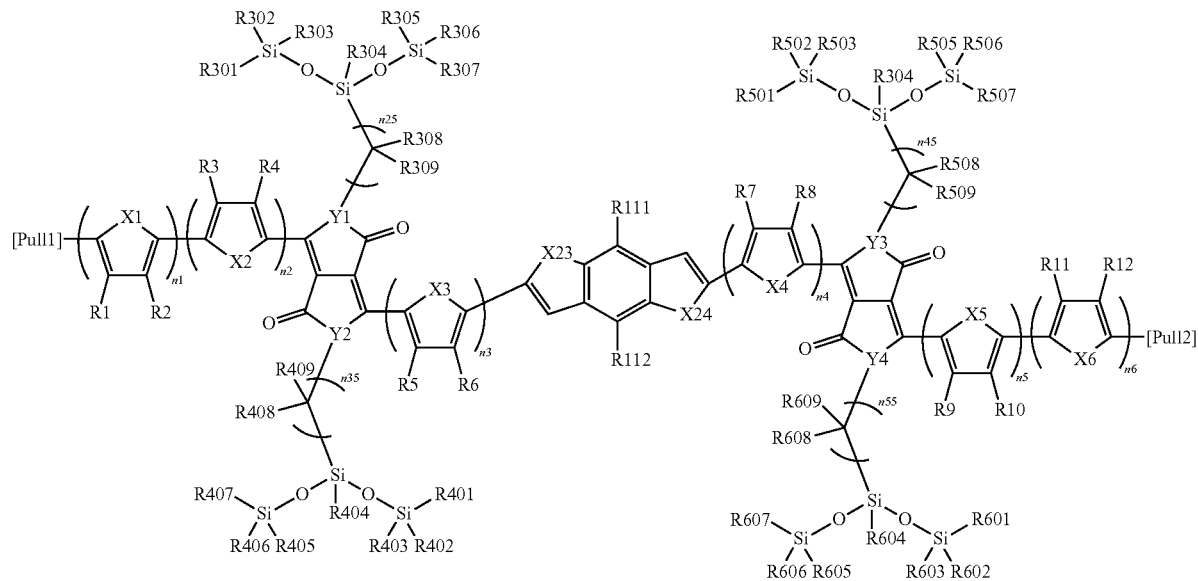

[Chemical Formula 1-6]
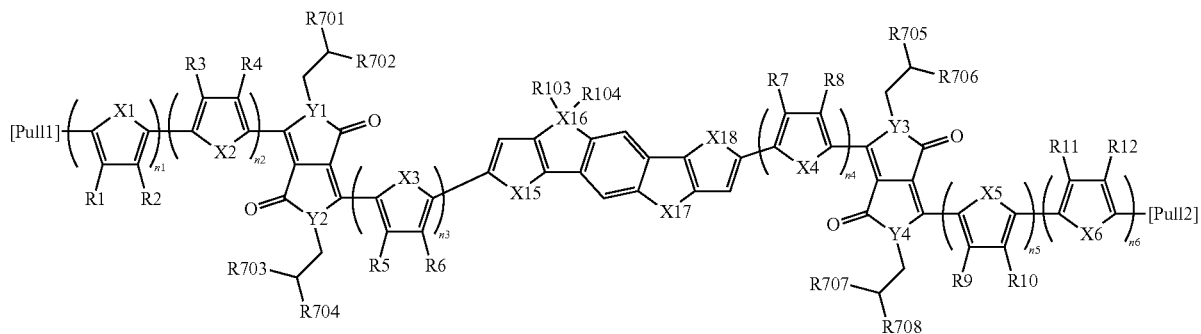
[Chemical Formula 1-7]
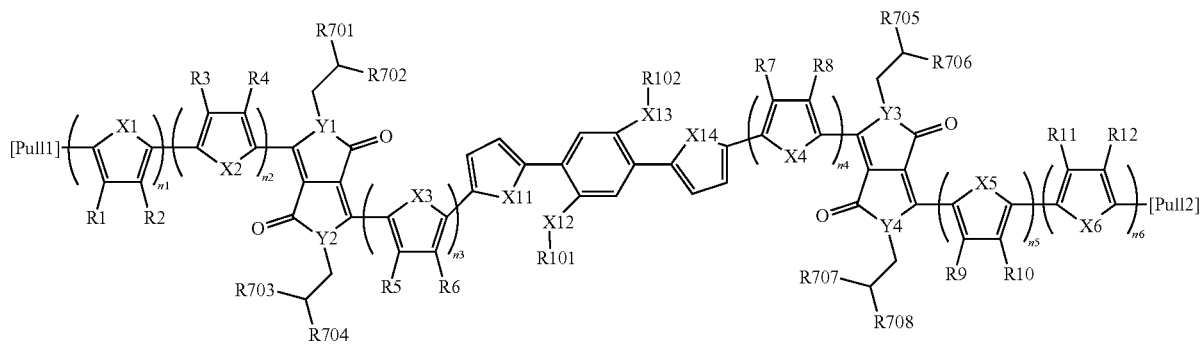
[Chemical Formula 1-8]
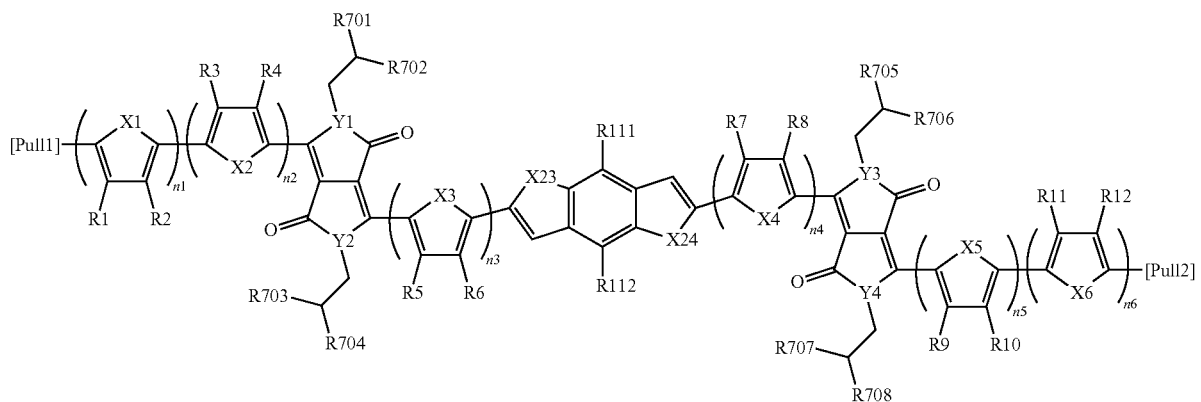
wherein:
n1 to n6 are each an integer from 1 to 3,
when n1 is 2 or more, two or more
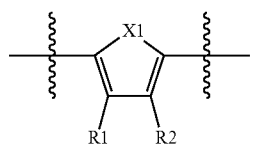
are the same as or different from each other,
when n2 is 2 or more, two or more
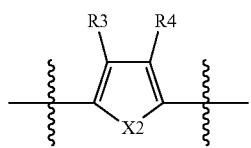
are the same as or different from each other, when n3 is 2 or more, two or more

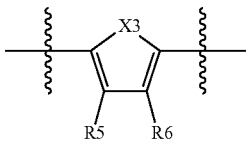

are the same as or different from each other,
when n4 is 2 or more, two or more

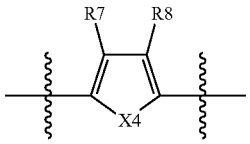

are the same as or different from each other,
when n5 is 2 or more, two or more

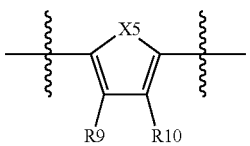

are the same as or different from each other, and
when n6 is 2 or more, two or more

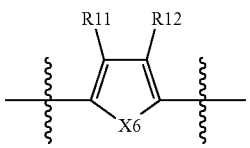

are the same as or different from each other;
X1 to X6 are the same as or different from each other, and are each independently CRR', NR, O, SiRR', PR, S, GeRR', Se, or Te;
Y1 to Y4 are the same as or different from each other, and are each independently CR", N, SiR", P, or GeR";
X11, X14, X15, X17, X23, and X24 are the same as or different from each other, and are each independently CRR', NR, O, SiRR', PR, S, GeRR', Se, or Te;
X12 and X13 are the same as or different from each other, and are each independently O, SiRR', or S;
X16 is C, Si, or Ge;
X18 is S;
[Pull1] and [Pull2] are the same as or different from each other, and are each any one of the following structures:

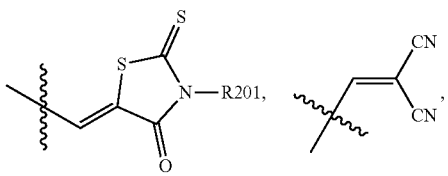

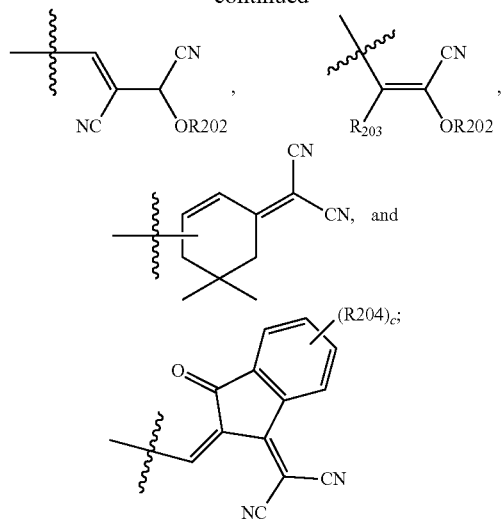

c is an integer from 1 to 4, and
when c is 2 or more, two or more R204 are the same as or different from each other;
R, R', R", R1 to R12, R101 to R104, R111, R112, and R201 to R204 are the same as or different from each other, and are each independently hydrogen, deuterium, a halogen group, a nitrile group, a nitro group, an imide group, an amide group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted siloxane group, a substituted or unsubstituted boron group, a substituted or unsubstituted amine group, a substituted or unsubstituted aryl group, or a substituted or unsubstituted heterocyclic group;
in the Chemical Formulae 1-6 to 1-8, at least one of R101 to R104, R111, and R112 includes a substituted or unsubstituted silyl group or a substituted or unsubstituted siloxane group;
n25, n35, n45, and n55 are each an integer from 0 to 5, when n25 is 2 or more, two or more

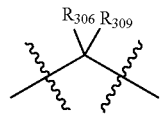

are the same as or different from each other,
when n35 is 2 or more, two or more

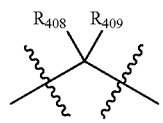

are the same as or different from each other, when n45 is 2 or more, two or more

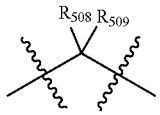

are the same as or different from each other, and when n55 is 2 or more, two or more

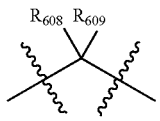

are the same as or different from each other; and
R301 to R309, R401 to R409, R501 to R509, R601 to R609, and R701 to R708 are the same as or different from each other, and are each independently hydrogen, deuterium, a halogen group, a nitrile group, a nitro group, an imide group, an amide group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted siloxane group, a substituted or unsubstituted boron group, a substituted or unsubstituted amine group, a substituted or unsubstituted aryl group, or a substituted or unsubstituted heterocyclic group.

8. The organic transistor of claim 7, wherein R1 to R12, R101 to R104, R111, R112, and R201 to R204 are the same as or different from each other, and are each independently hydrogen, a halogen group, a substituted or unsubstituted alkyl group, a substituted or unsubstituted cycloalkyl group, a substituted or unsubstituted alkoxy group, a substituted or unsubstituted silyl group, a substituted or unsubstituted siloxane group, a substituted or unsubstituted amine group, a substituted or unsubstituted aryl group, or a substituted or unsubstituted heterocyclic group.

9. The organic transistor of claim 7, wherein R1 to R12, R101 to R104, R111, R112, and R201 to R204 are the same as or different from each other, and are each independently hydrogen, a substituted or unsubstituted alkyl group, a substituted or unsubstituted silyl group, or a substituted or unsubstituted siloxane group.

10. The organic transistor of claim 7, wherein X1 to X6 are the same as or different from each other, and are each independently O, SiRR', or S.

11. The organic transistor of claim 7, wherein Y1 to Y4 are the same as or different from each other, and are each independently CR'', N, or SiR''.

12. The organic transistor of claim 7, wherein X11, X14, X15, X17, X23, and X24 are the same as or different from each other, and are each independently O, SiRR'', or S.

13. The organic transistor of claim 7, wherein the [Pull1] and the [Pull2] are each

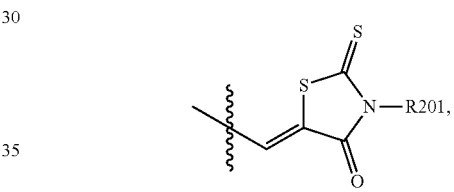

and
the definition of 8201 is the same as in Chemical Formulae 1-3 to 1-8.

14. The organic transistor of claim 7, wherein one of Chemical Formulae 1-3 to 1-8 is one of the following compound:

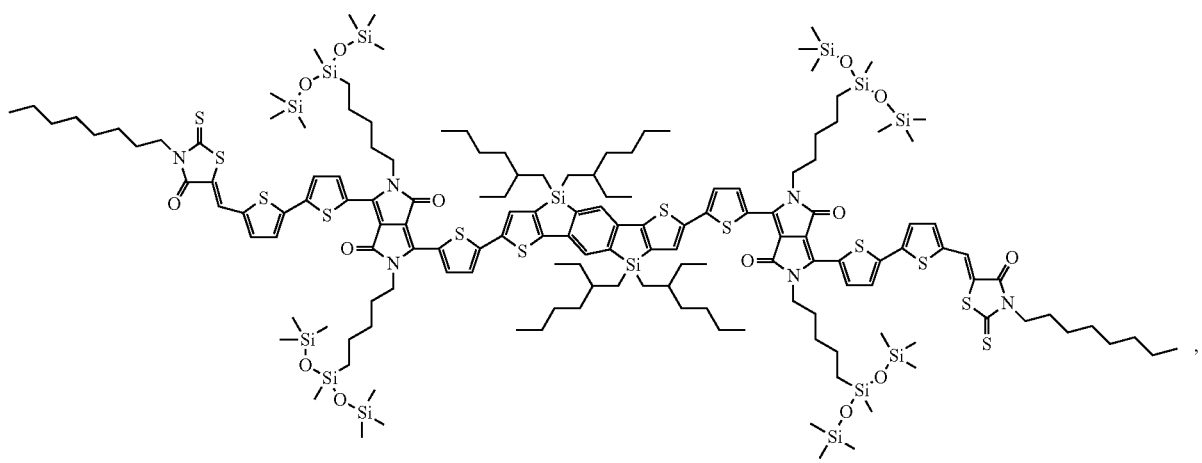

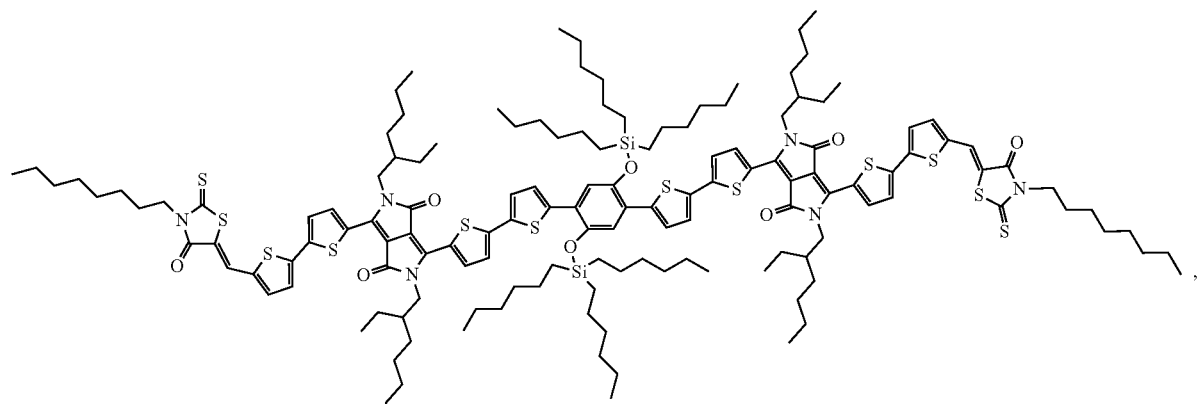
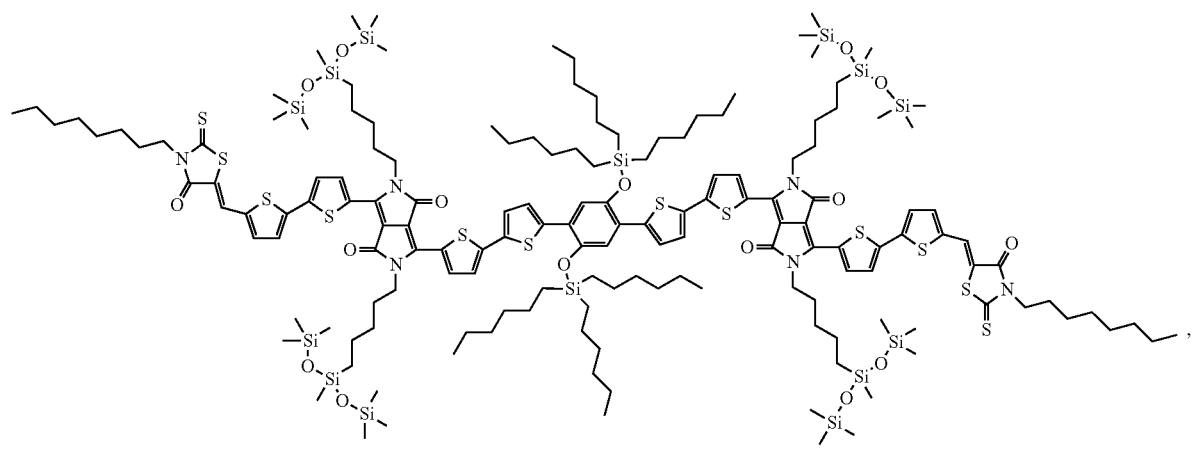
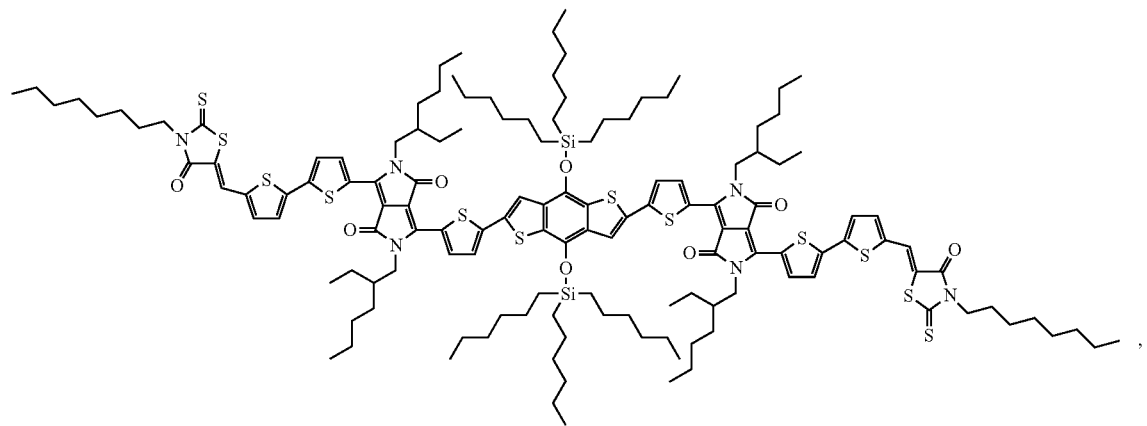

83
84
-continued
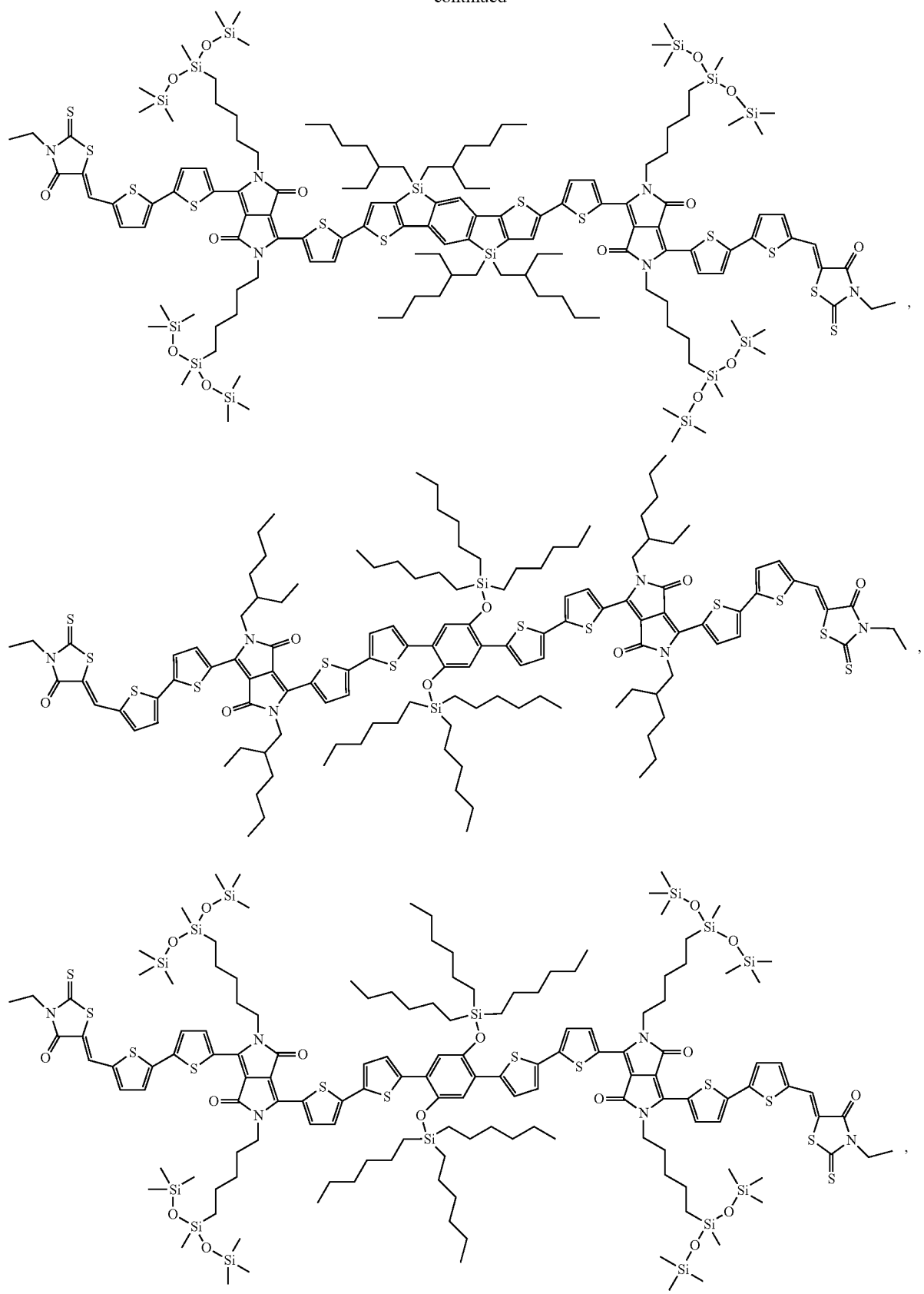
and

-continued

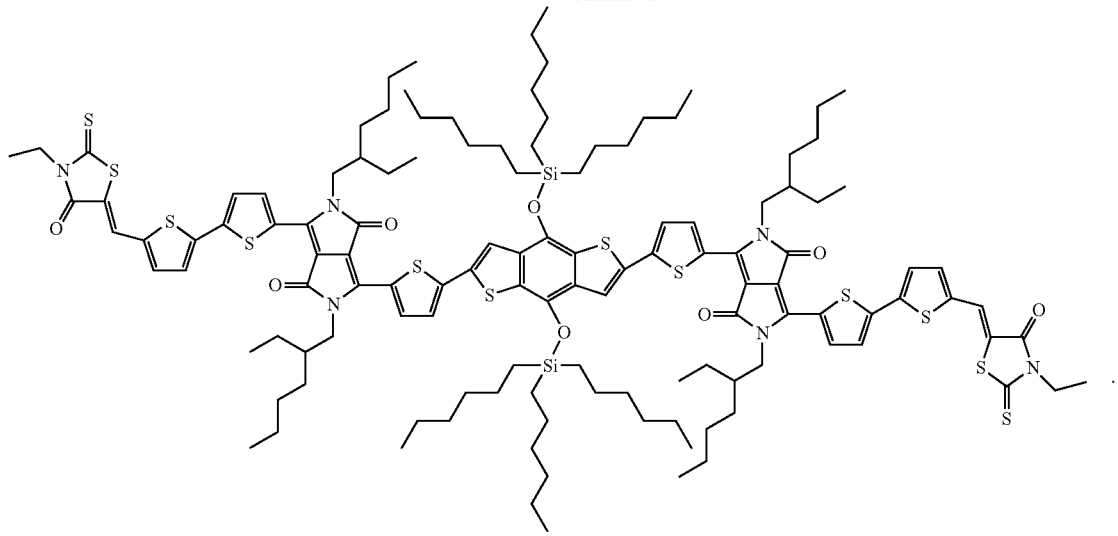 [SMILES: CCCCCC[Si](CCCCCC)(CCCCCC)Oc1c2cc(-c3ccc(C4=C5C(=O)N(CC(CC)CCCC)C(c6ccc(-c7ccc(/C=C8\SC(=S)N(CC)C8=O)s7)s6)=C5C(=O)N4CC(CC)CCCC)s3)sc2c(O[Si](CCCCCC)(CCCCCC)CCCCCC)c2cc(-c3ccc(C4=C5C(=O)N(CC(CC)CCCC)C(c6ccc(-c7ccc(/C=C8\SC(=S)N(CC)C8=O)s7)s6)=C5C(=O)N4CC(CC)CCCC)s3)sc12]

15. The organic transistor of claim 7, wherein the organic transistor further includes a gate electrode, a source electrode, a drain electrode, and an insulating layer, and
wherein the organic semiconductor layer contacts the insulating layer.

16. The organic transistor of claim 15, wherein the organic semiconductor layer contacts both the source electrode and the drain electrode.

17. A gas sensor comprising the organic transistor according to claim 7.

18. The gas sensor of claim 17, wherein the organic semiconductor layer further includes a carbon-based material.

19. The gas sensor of claim 17, wherein the gas sensor senses ammonia ($NH_3$), ethylene ($C_2H_4$), formaldehyde (HCHO), hydrofluoric acid (HF), nitrogen oxide, sulfur oxide or ethanol.

20. The gas sensor of claim 17, wherein the gas sensor is configured to detect sulfur oxide in air when a concentration of sulfur oxide is in a range of 0.1 ppm to 900,000 ppm.

* * * * *

UNITED STATES PATENT AND TRADEMARK OFFICE
CERTIFICATE OF CORRECTION

PATENT NO.        : 10,734,131 B2                                         Page 1 of 5
APPLICATION NO.   : 16/077146
DATED             : August 4, 2020
INVENTOR(S)       : Lim et al.

It is certified that error appears in the above-identified patent and that said Letters Patent is hereby corrected as shown below:

In the Claims

Column 72, Line 63, Claim 6:
Please correct "SiRR''" to read -- SiRR' --

Column 73, Bottom Left Segment of Chemical Formula 1-3, Claim 7:
Please delete:

"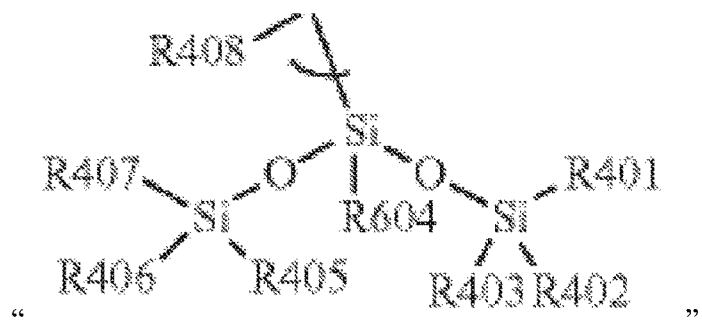"

And replace with:

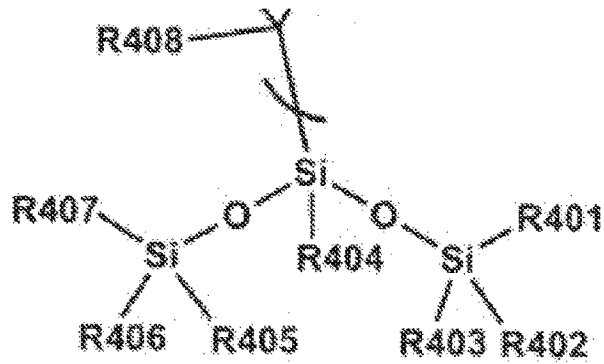

Signed and Sealed this
Sixth Day of April, 2021

Drew Hirshfeld
*Performing the Functions and Duties of the
Under Secretary of Commerce for Intellectual Property and
Director of the United States Patent and Trademark Office*

Column 74, Top Right Segment of Chemical Formula 1-4, Claim 7:
Please delete:
"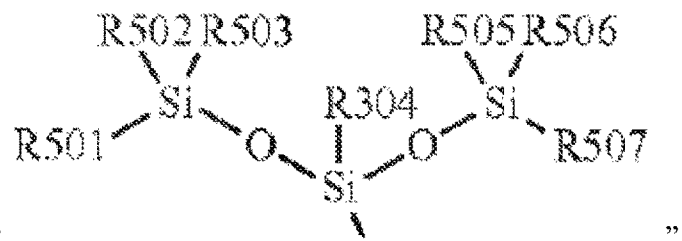"
And replace with:
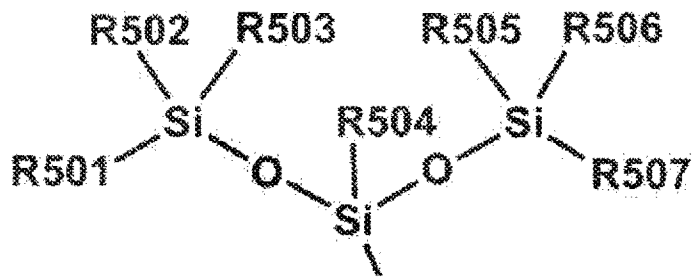
Column 74, Top Right Segment of Chemical Formula 1-5, Claim 7:
Please delete:
"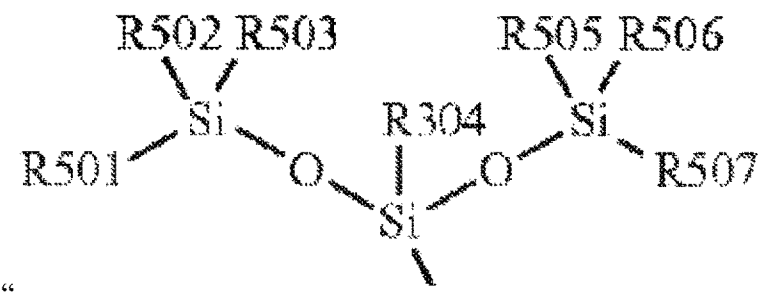"
And replace with:
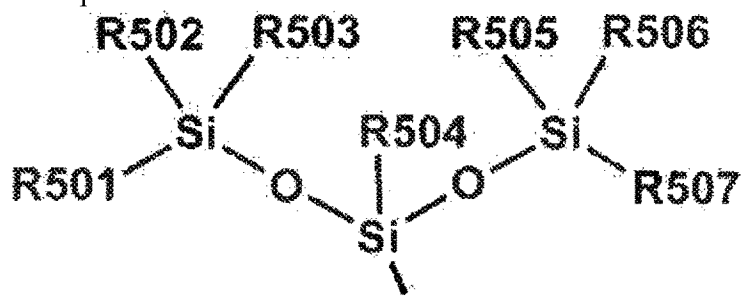

CERTIFICATE OF CORRECTION (continued)　　　　　　　　　　　　　　　　　Page 3 of 5
U.S. Pat. No. 10,734,131 B2

Column 78, Line 3, Claim 7:
Please delete:

"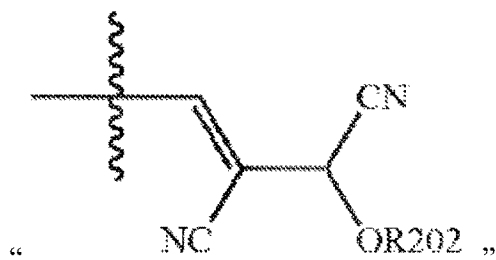"

And replace with:

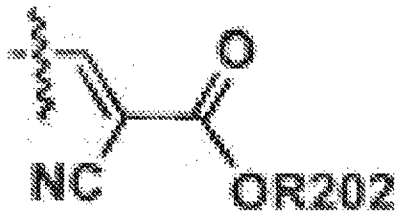

Column 78, Line 6, Claim 7:
Please delete:

"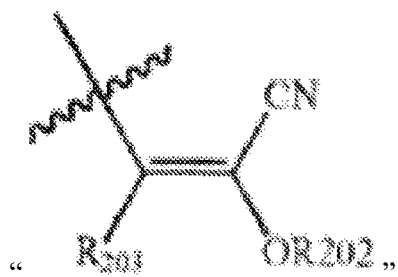"

And replace with:

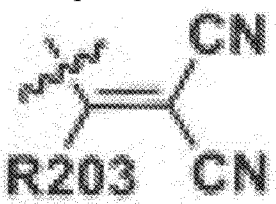

Column 78, Line 52, Claim 7:
Please delete:

"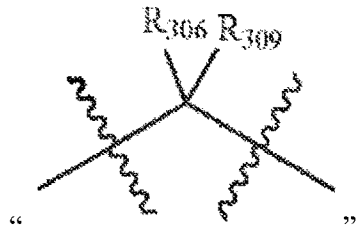"

And replace with:
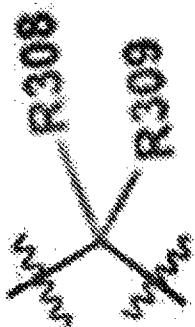
Column 78, Line 62, Claim 7:
Please delete:
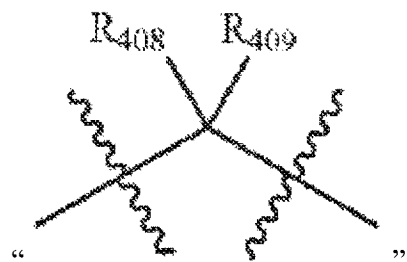
" "
And replace with:
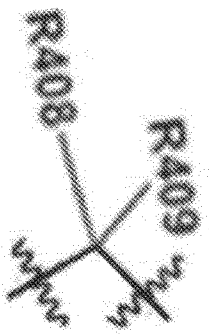
Column 79, Line 5, Claim 7:
Please delete:
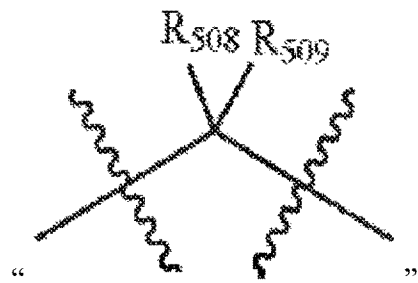
" "

And replace with:
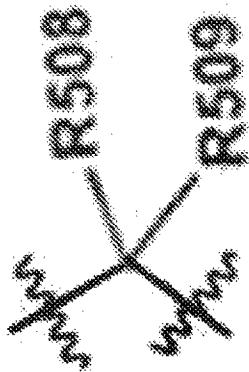
Column 79, Line 14, Claim 7:
Please delete:
"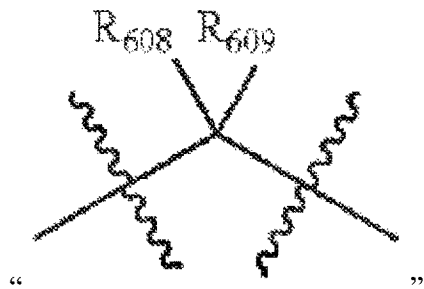"
And replace with:
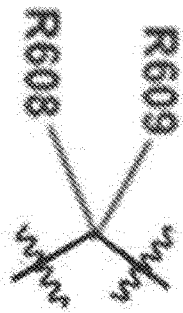
Column 80, Line 23, Claim 12:
Please correct "SiRR'"" to read -- SiRR' --
Column 80, Line 40, Claim 13:
Please correct "8201" to read -- R201 --